United States Patent
Timmer et al.

(10) Patent No.: US 10,308,720 B2
(45) Date of Patent: Jun. 4, 2019

(54) MULTIVALENT AND MULTISPECIFIC DR5-BINDING FUSION PROTEINS

(71) Applicant: Inhibrx, Inc., La Jolla, CA (US)

(72) Inventors: John C. Timmer, La Jolla, CA (US); Kyle S. Jones, La Jolla, CA (US); Amir S. Razai, La Jolla, CA (US); Abrahim Hussain, La Jolla, CA (US); Katelyn M. Willis, La Jolla, CA (US); Quinn Deveraux, La Jolla, CA (US); Brendan P. Eckelman, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 0 days.

(21) Appl. No.: 15/213,296

(22) Filed: Jul. 18, 2016

(65) Prior Publication Data
US 2017/0015753 A1 Jan. 19, 2017

Related U.S. Application Data

(60) Provisional application No. 62/193,309, filed on Jul. 16, 2015.

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/22* (2013.01); *C07K 2317/24* (2013.01); *C07K 2317/33* (2013.01); *C07K 2317/35* (2013.01); *C07K 2317/567* (2013.01); *C07K 2317/569* (2013.01); *C07K 2317/73* (2013.01); *C07K 2317/75* (2013.01)

(58) Field of Classification Search
None
See application file for complete search history.

(56) References Cited

U.S. PATENT DOCUMENTS

| | | |
|---|---|---|
| 5,955,358 A | 9/1999 | Huse |
| 8,124,076 B2 | 2/2012 | Solomon et al. |
| 8,575,070 B2 | 11/2013 | Watt et al. |
| 8,623,369 B2 | 1/2014 | Abulrob et al. |
| 8,962,807 B2 | 2/2015 | Verdonck et al. |
| 9,120,855 B2 * | 9/2015 | Cromie ............. C07K 16/2878 |

(Continued)

FOREIGN PATENT DOCUMENTS

| | | |
|---|---|---|
| JP | 2008133206 A | 6/2008 |
| WO | 2006073941 A2 | 7/2006 |

(Continued)

OTHER PUBLICATIONS

Vincke et al., General Strategy to Humanize a Camelid Single-domain Antibody and Identification of a Universal Humanized Nanobody Scaffold, J. Biol. Chem. 284:3273-3284, Jan. 30, 2009. (Year: 2009).*

(Continued)

*Primary Examiner* — Claire Kaufman
(74) *Attorney, Agent, or Firm* — McNeill Baur PLLC

(57) ABSTRACT

The disclosure relates generally to molecules that specifically engage death receptor 5 (DR5), a member of the TNF receptor superfamily (TNFRSF). More specifically the disclosure relates to multivalent and multispecific molecules that bind at least DR5.

24 Claims, 15 Drawing Sheets
Specification includes a Sequence Listing.

(56) References Cited

U.S. PATENT DOCUMENTS

| | | | |
|---|---|---|---|
| 9,771,416 | B2 | 9/2017 | Hussack et al. |
| 9,862,777 | B2 | 1/2018 | Robberecht et al. |
| 9,879,093 | B2 | 1/2018 | Seidah et al. |
| 2002/0147140 | A1 | 10/2002 | Rosen et al. |
| 2009/0191186 | A1 | 7/2009 | Bebbington et al. |
| 2011/0166076 | A1 | 7/2011 | Adams et al. |
| 2011/0182897 | A1 | 7/2011 | Hultberg et al. |
| 2012/0064106 | A1 | 3/2012 | Mizel et al. |
| 2013/0095109 | A1 | 4/2013 | Nadler et al. |
| 2013/0266575 | A1 | 10/2013 | Klade et al. |
| 2014/0161796 | A1 | 6/2014 | Loew et al. |
| 2014/0227259 | A1 | 8/2014 | Ashman et al. |
| 2015/0139997 | A1 | 5/2015 | Vermot-Desroches et al. |
| 2015/0284450 | A1 | 10/2015 | Digiandomenico et al. |
| 2016/0326256 | A1* | 11/2016 | Nishikawa ............. A61K 35/74 |

FOREIGN PATENT DOCUMENTS

| | | | |
|---|---|---|---|
| WO | 2006091734 | A2 | 8/2006 |
| WO | 2007066106 | A1 | 6/2007 |
| WO | 2010115141 | A2 | 10/2010 |
| WO | 2011098520 | A1 | 8/2011 |
| WO | 2012041800 | A1 | 4/2012 |
| WO | 2013070565 | A1 | 5/2013 |
| WO | 2013128031 | A1 | 9/2013 |
| WO | 2013024059 | A9 | 4/2014 |
| WO | 2014111550 | A1 | 7/2014 |

OTHER PUBLICATIONS

Hultberg et al., Llama-derived single-domain antibodies to build multivalent, superpotent and broadened neutralizing anti-viral molecules. PLoS One, 6(4):1-12, e17665-10.1371/journal.pone.0017665. (Year: 2011).*

De Miguel, D. et al., Liposome-bound TRAIL induces superior DR5 clustering and enhanced DISC recruitment in histiocyclic lymphoma U937 cells. Leuk Res. Epub Apr. 4, 2015, 39(6):657-666.

De Miguel, D. et al., "Onto Better TRAILS for Cancer Treatment," Cell Death and Differentiation (2016) 23, pp. 733-747.

Holland, Pamela, "Death Receptor Agonist Therapies for Cancer, Which is the Right TRAIL?," Cytokine & Growth Factor Reviews 25 (2014) pp. 185-191.

Huet, H. et al., "Multivalent Nanobodies Targeting Death Receptor 5 Elicit Superior Tumor Cell Killing through Efficient Caspase Induction," Novartis Institutes for Biomedical Research 6:6, (Nov./Dec. 2014) pp. 1560-1570.

International Search Report and Written Opinion for PCT/US2016/042862 dated Jan. 12, 2017, 7 pages.

Naoum, G. et al., "Journey of TRAIL from Bench to Bedside and its Potential Role in Immuno-oncology," Oncology Reviews 2017; vol. 11:332, pp. 26-42.

Papadopoulos, K. et al., "Unexpected Hepatotoxicity in a phase I study of TAS266, a Novel Tetravalent Agonistic Nanobody Targeting the DR5 Receptor," Cancer Chemother Pharmacol (2015) pp. 887-895.

Reddy, A, et al. "Gene Expression Ratios Lead to Accurate and Translatable Predictors of DR5 Agonism across Multiple Tumor Lineages," PLOS One, (Sep. 17, 2015), pp. 1-18.

Partial Supplementary European Search Report for European Application No. 16825315.1 dated Jan. 2, 2019; 15 pages.

Alegre et al. "Effect of a single amino acid mutation on the activating and immunosuppressive properties of a humanized' OKT3 monoclonal antibody", The Journal of Immunology, 1992, vol. 148, pp. 3461-3468.

Baldrick P. "Pharmaceutical Excipient Development: The Need for Preclinical Guidance" Regulatory Toxicology and Pharmacology, 2000, vol. 32, pp. 210-218.

Bowie et al. "A Method to Identify Protein Sequences That Fold into a Known Three-Dimensional Structure", 1991, Science, vol. 253, pp. 164-171.

Carter, "Bispecific human IgG by design", Journal of Immunological Methods, 2001, vol. 248, pp. 7-15.

Charman W. "Lipids, Lipophilic Drugs, and Oral Drug Delivery—Some Emerging Concepts" Journal of Pharmaceutical Sciences, 2000, vol. 89, No. 8, pp. 967-978.

Chothia & Lesk "Canonical Structures for the Hypervariable Regions of Immunoglobulins", J. Mol. Biol., 1987, vol. 196, pp. 901-917.

Chothia et al. "Conformations of immunoglobulin hypervariable regions", Nature, 1989, vol. 342, pp. 877-883.

Cordy, J.C., et al. "Specificity of Human Anti-Variable Heavy (Vh) Chain Autoantibodies and Impact on the Design and Clinical Testing of a Vh Domain Antibody Antagonist of Tumour Necrosis Factor-a Receptor 1," British Society for Immunology, Clinical and Experimental Immunology, 182, (2015) pp. 139-148.

Dall' Acqua et al. "Properties of Human IgG Is Engineered for Enhanced Binding to the Neonatal Fe Receptor (FcRn)", The Journal of Biological Chemistry, 2006, vol. 281, No. 32, pp. 23514-23524.

Davies et al. "Antibody-Antigen Complexes", Annual Rev Biochem, 1990, vol. 59, pp. 439-473.

Di Giandomenico, et al. "A multifunctional bispecific antibody protects against Pseudomonas aeruginosa", Science Translation Medicine, 2014, vol. 6, Issue 262, 262ra155, 13 pages.

Evans et al. "Design of Nonpeptidal Ligands for a Peptide Receptor: Cholecystokinin Antagonists", J. Med. Chem., 1987, vol. 30, pp. 1229-1239.

Fauchere, "Elements for the Rational Design of Peptide Drugs", Advances in Drug Research, 1986, vol. 15, pp. 29-69.

Holland, M.C. et al., "Autoantibodies to Variable Heavy (VH) Chain Ig Sequences in Humans Impact the Safety and Clinical Pharmacology of a VH Domain Antibody Antagonist of TNF-a Receptor 1," J. Clin Immunol (2013) 33:1192-1203.

Idusogie et al. "Engineered Antibodies with Increased Activity to Recruit Complement", The Journal ofImmunolo2:v, 2001, vol. 166, No. 4, pp. 2571-2575.

International Preliminary Report on Patentability issued in PCT/US2016/014296, dated Jun. 6, 2016, 6 pages.

International Search Report and Written Opinion for PCT/US2016/014296 dated Jul. 1, 2016, 5 pages.

Kaneko and Niwa, "Optimizing Therapeutic Antibody Function", Biodrugs, 2011, vol. 25, No. 1, pp. 1-11.

Lazar et al. "Engineered antibody Fe variants with enhanced effector function", PNAS, 2006, vol. 103. No. 11. pp. 4005-4010.

Malmqvist, M. "Biospecific interaction analysis using biosensor technology", Nature, 1993, vol. 361, pp. 186-187.

Moore et al., "Engineered Fe variant antibodies with enhanced ability to recruit complement and mediate effect or function". mAbs. 2010. vol. 2. No. 2. pp. 181-189.

Natsume et al. "Engineered Antibodies of IgG I/IgG3 Mixed Isotype with Enhanced Cytotoxic Activities", Cancer Research, 2008, Vol. 68, No. 10, pp. 3863-3872.

Powell et al. "Compendium of Excipients for Parenteral Formulations" PDA Journal of Pharmaceutical Science and Technolo2:v, 1998, vol. 52, pp. 238-311.

Rizo and Gierasch "Constrained Peptides: Models of Bioactive Peptides and Protein Substructures", Ann. Rev. Biochem 1992, vol. 61, pp. 387-418.

Saerens et al, "Single-domain antibodies as building blocks for novel therapeutics:" Current Opinion in Pharmacology 8:600- 608. (2008).

Shields et al. "High Resolution Mapping of the Binding Site on Human IgG 1 for FcyRl, FcyRll, FcyRIII, and FcRn and Design of IgG I Variants with Improved Binding to the FcyR", The Journal of Biological Chemistry, 2001, vol. 276, No. 9, pp. 6591-6604.

Stavenhagen et al. "Enhancing the potency of therapeutic monoclonal antibodies via Fc optimization", Advances in Enzyme Regulations, 2008, vol. 48, pp. 152-164.

Stavenhagen et al. "Fc Optimization of Therapeutic Antibodies Enhances Their Ability to Kill Tumor Cells in vitro and Controls Tumor Expansion in vivo via Low-Affinity Activating Fey Receptors", Cancer Research, 2007, vol. 67, No. 18, pp. 8882-8890.

Thornton et al. "Prediction of progress at last", Nature, 1991, vol. 354, pp. 105-106.

(56) References Cited

OTHER PUBLICATIONS

UniProt Accession MOJ6E7_9EURY (Oct. 1, 2014) Retrieved from the Internet May 30, 2016: J; amino acids 143-150, 100% identity); 1 page.

Vaneycken et al., "In Vitro Analysis and in Vivo Tumor Targeting of Humanized, Grafted Nanobody in Mice Using Pinhole SPECT/Micro-CT," The Journal of Nuclear Medicine, vol. 51, No. 7, Jul. 2010, 9 pages.

Veber and Freidinger The design of metabolically-stable peptide analogs, TINS, Sep. 1985, P. 392-396.

Wang W. "Lyophilization and development of solid protein pharmaceuticals." International Journal of Pharmaceutics, 2000, vol. 203, Nos. 1-2, pp. 1-60.

Yin et al., "Characterization of Asia 1 sdAb from Camels Bactrianus (C. bactrianus) and Conjugation with Quantum Dots for Imaging FMDV in BHK-21 Cells," PLOS One, vol. 8, Issue 5, May 2013, 10 pages.

Zalevsky et al. "Enhanced antibody half-life improves in vivo activity", Nature Biotechnology, 2010, vol. 28, No. 2, pp. 157-159.

\* cited by examiner

FIG 2
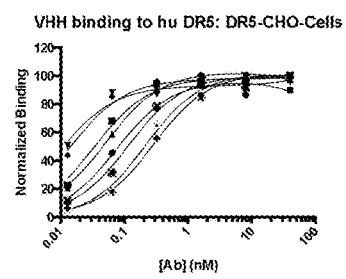
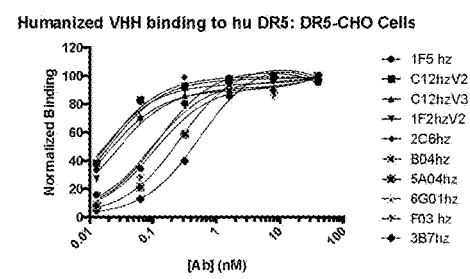
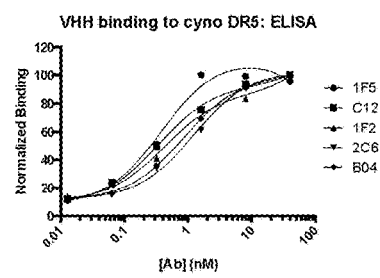
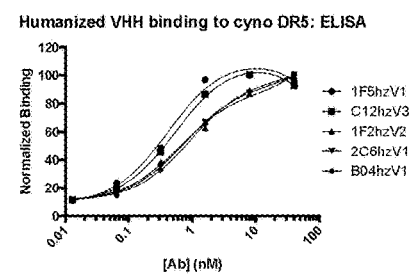

FIG 2
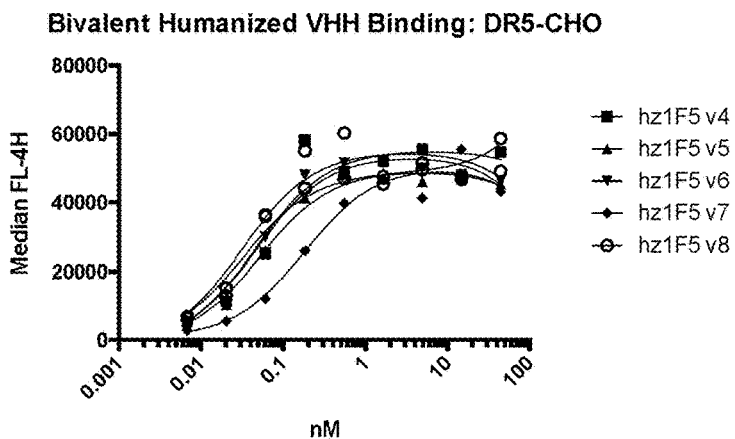
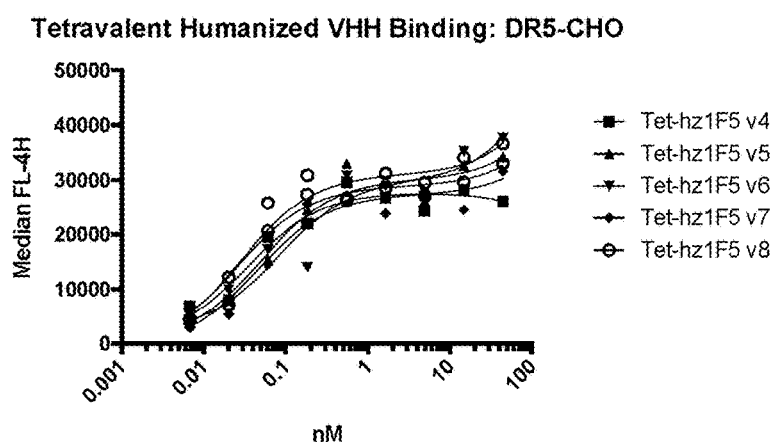
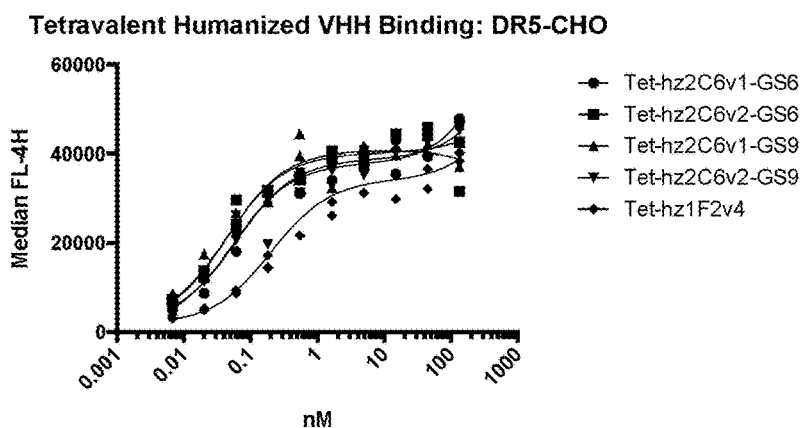

FIG 3
A.
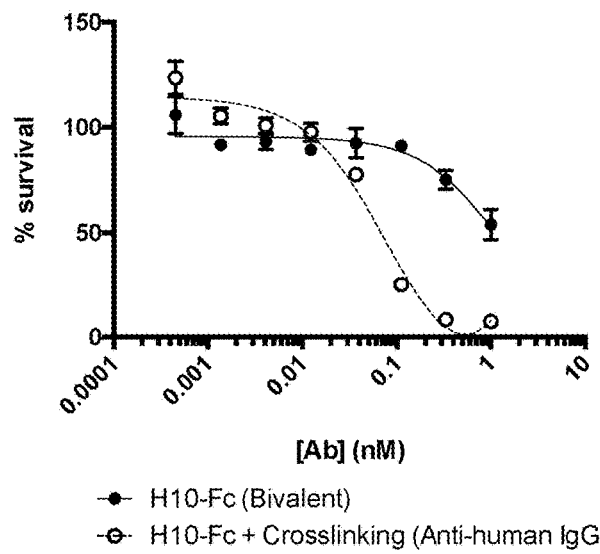
B.
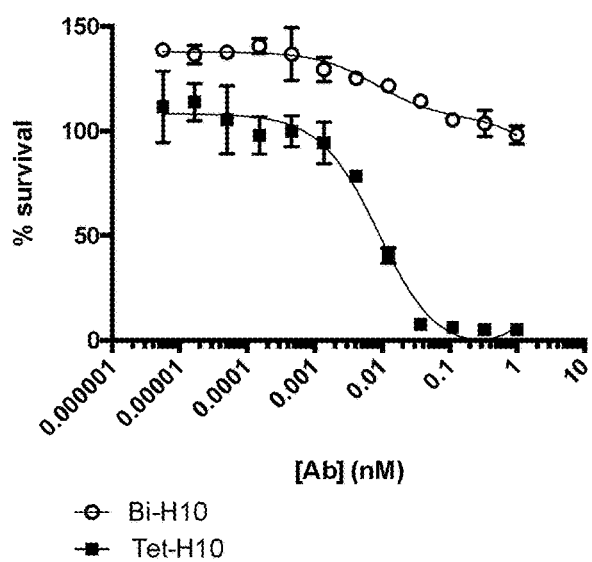

FIG 4
A.
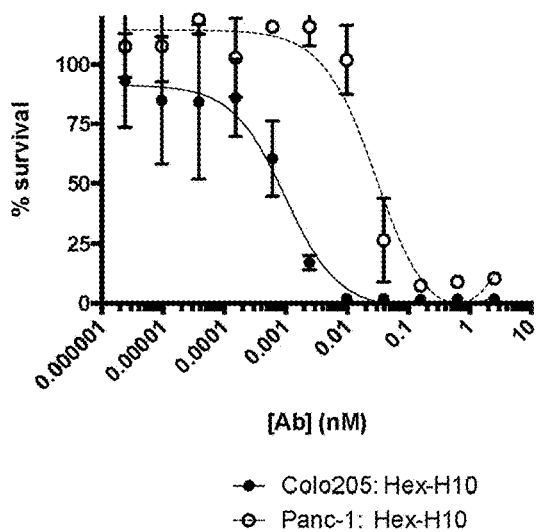
B.
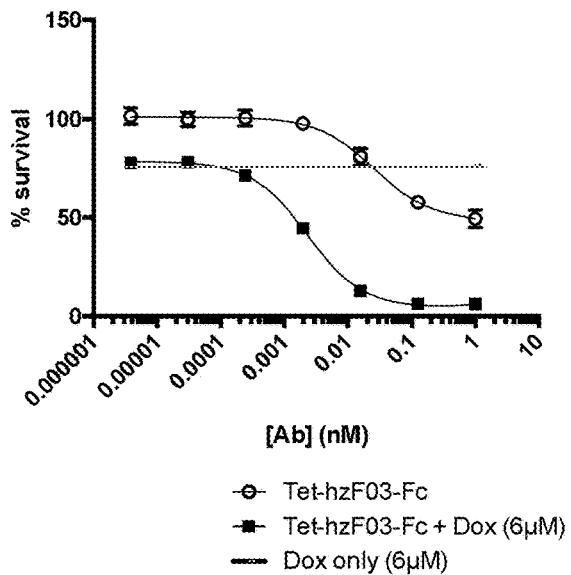

A.

FIG 6
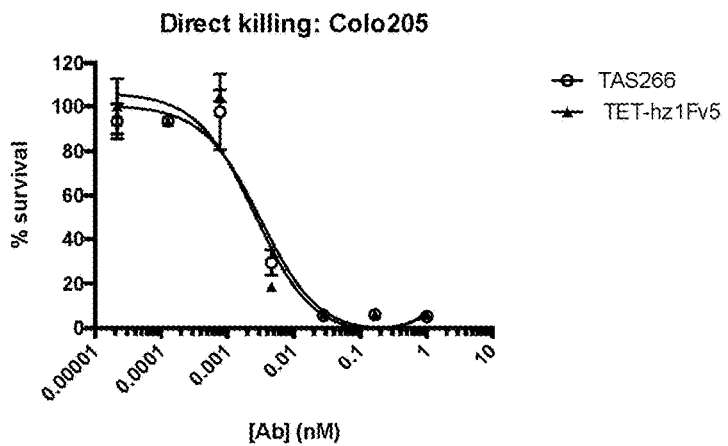
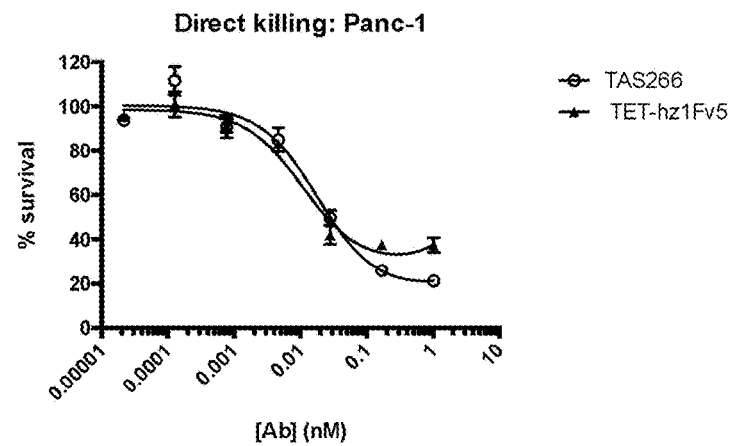
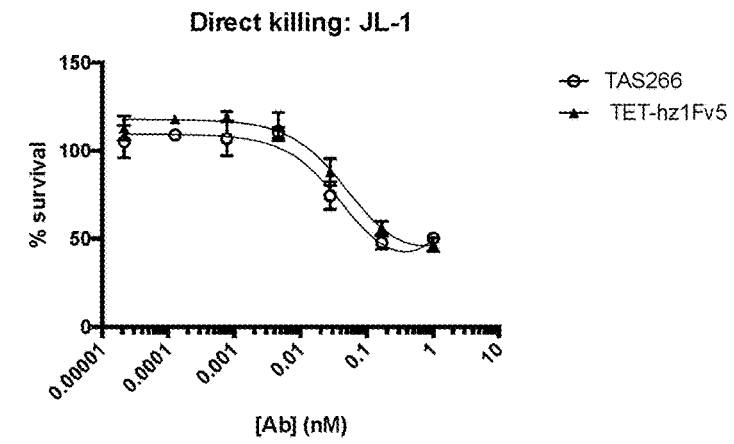

FIG 7
A.
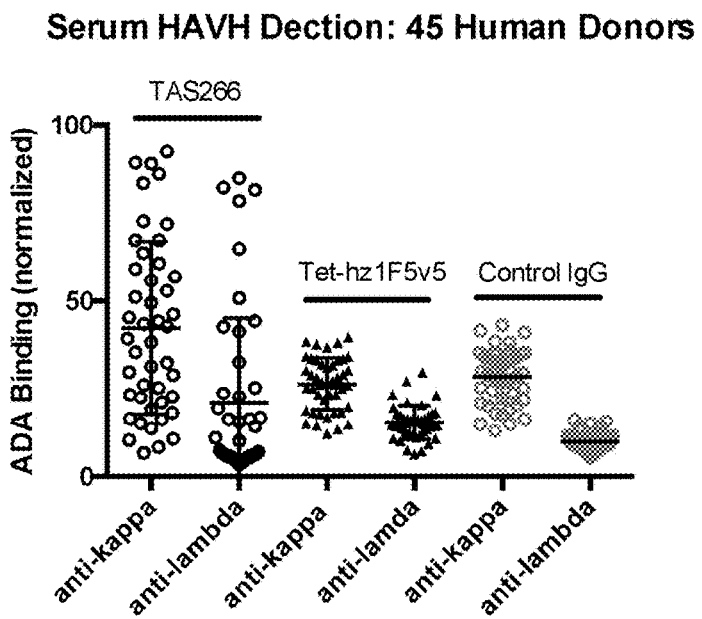
B.
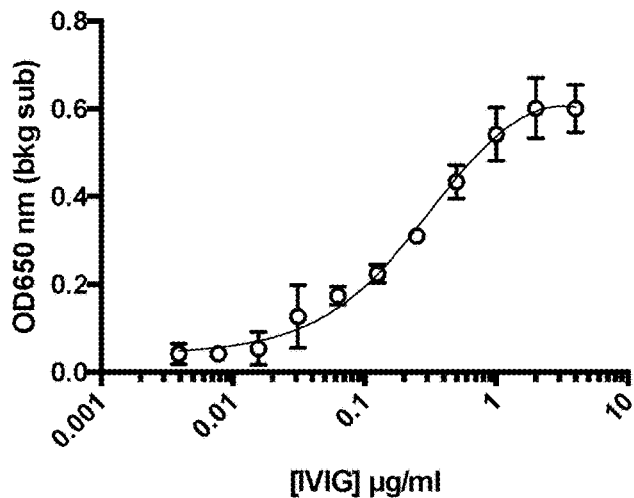

C.

FIG 8
A.
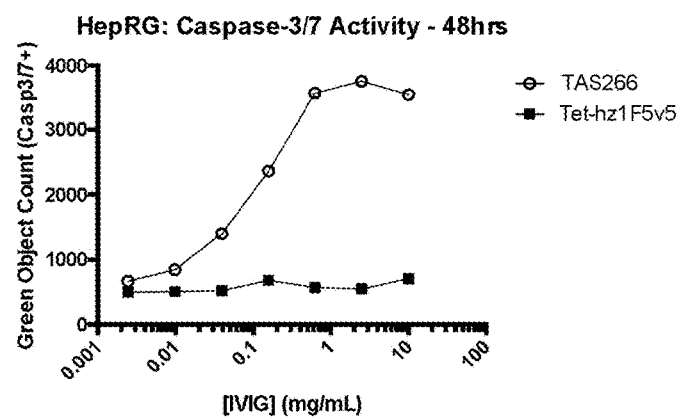
B.
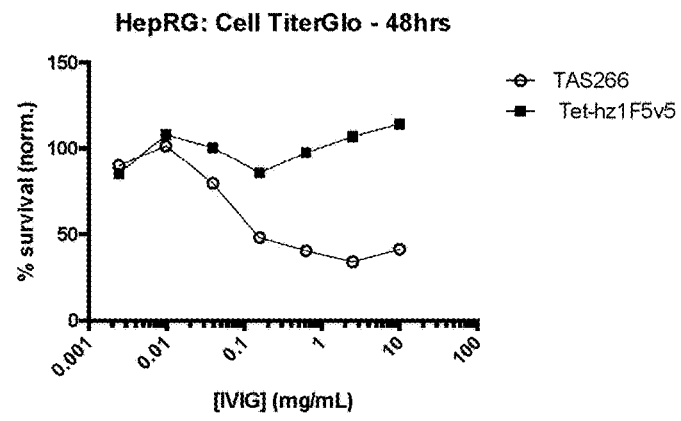

FIG 9
A.
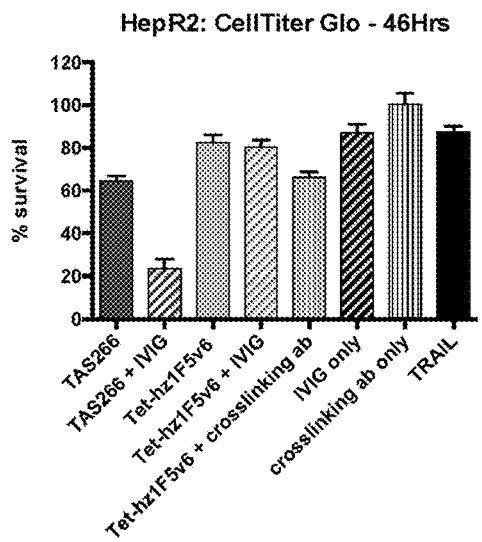
B.
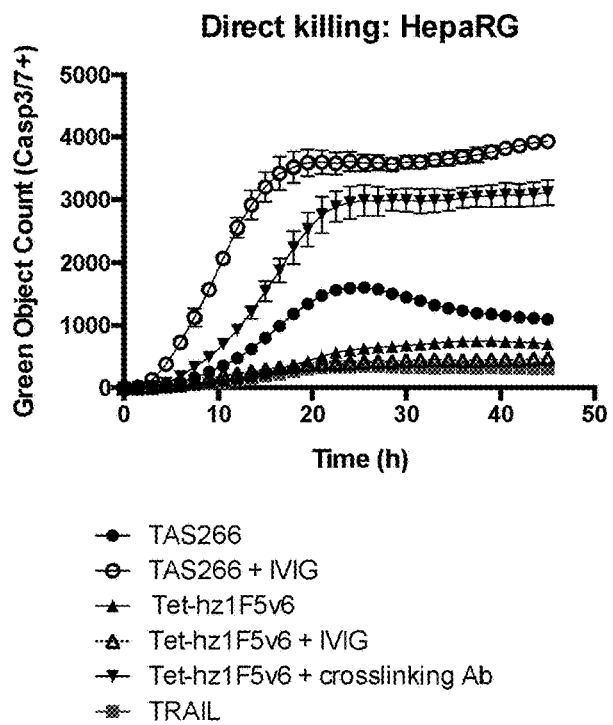

FIG 9
C.
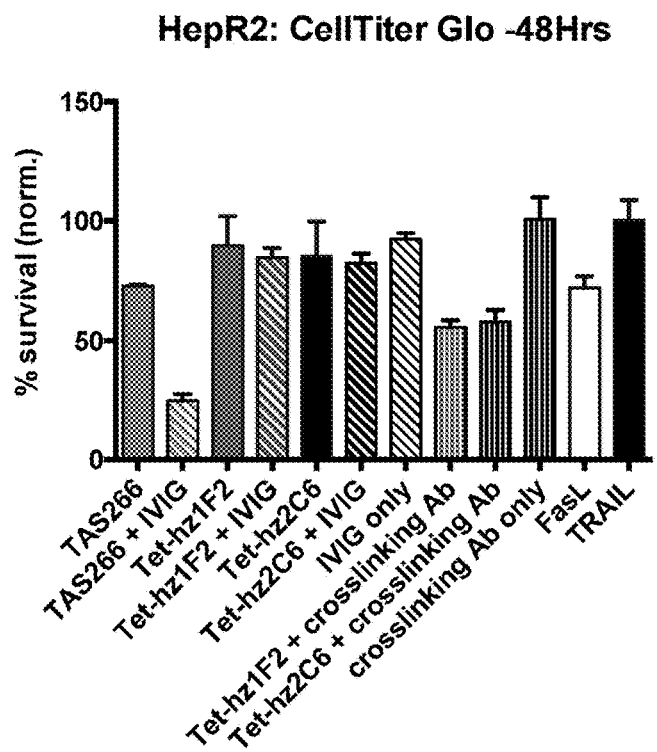
D.
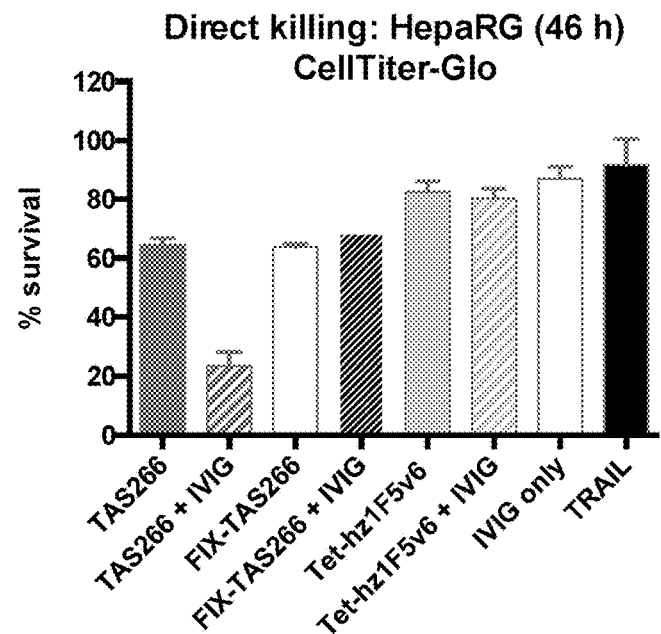

SEQUENCE LISTING

```
<160> NUMBER OF SEQ ID NOS: 190

<210> SEQ ID NO 1
<211> LENGTH: 218
<212> TYPE: PRT
<213> ORGANISM: Artificial Sequence
<220> FEATURE:
<223> OTHER INFORMATION: chemically synthesized

<400> SEQUENCE: 1

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30
```

```
Val Val Val Asp Val Ser His Glu Asp Pro Glu Val Lys Phe Asn Trp
         35                  40                  45

Tyr Val Asp Gly Val Glu Val His Asn Ala Lys Thr Lys Pro Arg Glu
 50                  55                  60

Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
             100                 105                 110

Gln Pro Arg Glu Pro Gln Val Tyr Thr Leu Pro Pro Ser Arg Asp Glu
         115                 120                 125

Leu Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                 165                 170                 175

Leu Tyr Ser Lys Leu Thr Val Asp Lys Ser Arg Trp Gln Gln Gly Asn
             180                 185                 190

Val Phe Ser Cys Ser Val Met His Glu Ala Leu His Asn His Tyr Thr
         195                 200                 205

Gln Lys Ser Leu Ser Leu Ser Pro Gly Lys
    210                 215

<210> SEQ ID NO 2
<211> LENGTH: 215
<212> TYPE: PRT
<213> ORGANISM: Artificial Sequence
<220> FEATURE:
<223> OTHER INFORMATION: chemically synthesized

<400> SEQUENCE: 2

Pro Ala Pro Gly Gly Pro Ser Val Phe Leu Phe Pro Pro Lys Pro Lys
1               5                  10                  15

Asp Thr Leu Met Ile Ser Arg Thr Pro Glu Val Thr Cys Val Val Val
             20                  25                  30

Asp Val Ser His Glu Asp Pro Glu Val Lys Phe Asn Trp Tyr Val Asp
         35                  40                  45

Gly Val Glu Val His Asn Ala Lys Thr Lys Pro Arg Glu Glu Gln Tyr
 50                  55                  60

Asn Ser Thr Tyr Arg Val Val Ser Val Leu Thr Val Leu His Gln Asp
 65                  70                  75                  80

Trp Leu Asn Gly Lys Glu Tyr Lys Cys Lys Val Ser Asn Lys Ala Leu
                 85                  90                  95

Pro Ala Pro Ile Glu Lys Thr Ile Ser Lys Ala Lys Gly Gln Pro Arg
             100                 105                 110

Glu Pro Gln Val Tyr Thr Leu Pro Pro Ser Arg Asp Glu Leu Thr Lys
         115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                 165                 170                 175
```

```
Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
            195                 200                 205

Leu Ser Leu Ser Pro Gly Lys
    210                 215

<210> SEQ ID NO 3
<211> LENGTH: 217
<212> TYPE: PRT
<213> ORGANISM: Artificial Sequence
<220> FEATURE:
<223> OTHER INFORMATION: chemically synthesized

<400> SEQUENCE: 3

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 4
<211> LENGTH: 218
<212> TYPE: PRT
<213> ORGANISM: Artificial Sequence
<220> FEATURE:
<223> OTHER INFORMATION: chemically synthesized

<400> SEQUENCE: 4

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45
```

Tyr Val Asp Gly Val Glu Val His Asn Ala Lys Thr Lys Pro Arg Glu
            50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 5
<211> LENGTH: 218
<212> TYPE: PRT
<213> ORGANISM: Artificial Sequence
<220> FEATURE:
<223> OTHER INFORMATION: chemically synthesized

<400> SEQUENCE: 5

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 6
<211> LENGTH: 14
<212> TYPE: PRT
<213> ORGANISM: Artificial Sequence
<220> FEATURE:
<223> OTHER INFORMATION: chemically synthesized

<400> SEQUENCE: 6

Glu Pro Lys Ser Ser Asp Lys Thr His Thr Cys Pro Pro Cys
1               5                   10

<210> SEQ ID NO 7
<211> LENGTH: 9
<212> TYPE: PRT
<213> ORGANISM: Artificial Sequence
<220> FEATURE:
<223> OTHER INFORMATION: chemically synthesized

<400> SEQUENCE: 7

Asp Lys Thr His Thr Cys Pro Pro Cys
1               5

<210> SEQ ID NO 8
<211> LENGTH: 11
<212> TYPE: PRT
<213> ORGANISM: Artificial Sequence
<220> FEATURE:
<223> OTHER INFORMATION: chemically synthesized

<400> SEQUENCE: 8

Glu Ser Lys Tyr Gly Pro Pro Cys Pro Pro Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: chemically synthesized

<400> SEQUENCE: 9

Gly Gln Gly Thr Leu Val Thr Val Lys Pro Gly Gly
1               5                   10

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Gly Gln Gly Thr Leu Val Thr Val Glu Pro Gly Gly
1               5                   10

<210> SEQ ID NO 11
<211> LENGTH: 6
<212> TYPE: PRT
<213> ORGANISM: Artificial Sequence
<220> FEATURE:
<223> OTHER INFORMATION: chemically synthesized

<400> SEQUENCE: 11

Gly Gly Ser Gly Gly Ser
1               5

<210> SEQ ID NO 12
<211> LENGTH: 9
<212> TYPE: PRT
<213> ORGANISM: Artificial Sequence
<220> FEATURE:
<223> OTHER INFORMATION: chemically synthesized

<400> SEQUENCE: 12

Gly Gly Ser Gly Gly Ser Gly Gly Ser
1               5

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Gly Gly Ser Gly Gly Ser Gly Gly Ser Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: chemically synthesized

<400> SEQUENCE: 14

Gly Gly Ser Gly Gly Ser Gly Gly Ser Gly Gly Ser Gly Gly Ser
1               5                   10                  15

<210> SEQ ID NO 15
<211> LENGTH: 123
<212> TYPE: PRT
<213> ORGANISM: Artificial Sequence
<220> FEATURE:
<223> OTHER INFORMATION: chemically synthesized

<400> SEQUENCE: 15

Gln Val Gln Leu Val Gln Ser Gly Gly Leu Val Gln Ala Gly Asp
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Glu Glu Arg Glu Phe Leu
        35                  40                  45

Ala Val Ile Tyr Trp Ser Gly Gly Thr Val Phe Tyr Ala Asp Ser Val
    50                  55                  60

Lys Gly Arg Phe Thr Ile Ser Arg Asp Ala Ala Lys Asn Met Val Tyr
65                  70                  75                  80

Leu Gln Met Asn Ser Leu Lys Ser Asp Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Arg Gly Thr Gln Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: chemically synthesized

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
        35                  40                  45

Ser Ala Ile Tyr Trp Ser Gly Gly Thr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Ser Ser
        115                 120
```

<210> SEQ ID NO 17
<211> LENGTH: 125
<212> TYPE: PRT
<213> ORGANISM: Artificial Sequence
<220> FEATURE:
<223> OTHER INFORMATION: chemically synthesized

<400> SEQUENCE: 17

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
        35                  40                  45

Ser Ala Ile Tyr Trp Ser Gly Thr Val Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro Gly Gly
        115                 120                 125
```

<210> SEQ ID NO 18
<211> LENGTH: 123
<212> TYPE: PRT
<213> ORGANISM: Artificial Sequence
<220> FEATURE:
<223> OTHER INFORMATION: chemically synthesized

<400> SEQUENCE: 18

```
Glu Val Gln Leu Leu Glu Ser Gly Gly Gly Glu Val Gln Pro Gly Gly
```

```
 1               5                  10                 15
Ser Leu Arg Leu Ser Cys Ala Ala Ser Gly Leu Thr Phe Pro Asn Tyr
            20                 25                 30

Gly Met Ser Trp Phe Arg Gln Ala Pro Gly Lys Gly Leu Glu Phe Val
        35                 40                 45

Ser Ala Ile Tyr Trp Ser Gly Thr Val Tyr Tyr Ala Glu Ser Val
    50                 55                 60

Lys Gly Arg Phe Thr Ile Ser Arg Asp Asn Ala Lys Asn Thr Leu Tyr
65                  70                 75                 80

Leu Gln Met Ser Ser Leu Arg Ala Glu Asp Thr Ala Val Tyr Tyr Cys
                85                 90                 95

Ala Val Thr Ile Arg Gly Ala Ala Thr Gln Thr Trp Lys Tyr Asp Tyr
                100                105                110

Trp Gly Gln Gly Thr Leu Val Thr Val Lys Pro
            115                120

<210> SEQ ID NO 19
<211> LENGTH: 123
<212> TYPE: PRT
<213> ORGANISM: Artificial Sequence
<220> FEATURE:
<223> OTHER INFORMATION: chemically synthesized

<400> SEQUENCE: 19

Glu Val Gln Leu Leu Glu Ser Gly Gly Gly Val Gln Pro Gly Gly
1               5                  10                 15

Ser Leu Arg Leu Ser Cys Ala Ala Ser Gly Leu Thr Phe Pro Asn Tyr
            20                 25                 30

Gly Met Ser Trp Phe Arg Gln Ala Pro Gly Lys Glu Arg Glu Phe Val
        35                 40                 45

Ser Ala Ile Tyr Trp Ser Gly Thr Val Tyr Tyr Ala Glu Ser Val
    50                 55                 60

Lys Gly Arg Phe Thr Ile Ser Arg Asp Asn Ala Lys Asn Thr Leu Tyr
65                  70                 75                 80

Leu Gln Met Ser Ser Leu Arg Ala Glu Asp Thr Ala Val Tyr Tyr Cys
                85                 90                 95

Ala Val Thr Ile Arg Gly Ala Ala Thr Gln Thr Trp Lys Tyr Asp Tyr
                100                105                110

Trp Gly Gln Gly Thr Gln Val Thr Val Lys Pro
            115                120

<210> SEQ ID NO 20
<211> LENGTH: 125
<212> TYPE: PRT
<213> ORGANISM: Artificial Sequence
<220> FEATURE:
<223> OTHER INFORMATION: chemically synthesized

<400> SEQUENCE: 20

Glu Val Gln Leu Leu Glu Ser Gly Gly Gly Val Gln Pro Gly Gly
1               5                  10                 15

Ser Leu Arg Leu Ser Cys Ala Ala Ser Gly Leu Thr Phe Pro Asn Tyr
            20                 25                 30

Gly Met Ser Trp Phe Arg Gln Ala Pro Gly Lys Gly Leu Glu Phe Val
        35                 40                 45

Cys Ala Ile Tyr Trp Ser Gly Thr Val Tyr Tyr Ala Glu Ser Val
    50                 55                 60
```

```
Lys Gly Arg Phe Thr Cys Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Val Thr Ile Arg Gly Ala Thr Gln Thr Trp Lys Tyr Asp Tyr
            100                 105                 110

Trp Gly Gln Gly Thr Leu Val Thr Val Lys Pro Gly Gly
            115                 120                 125

<210> SEQ ID NO 21
<211> LENGTH: 124
<212> TYPE: PRT
<213> ORGANISM: Artificial Sequence
<220> FEATURE:
<223> OTHER INFORMATION: chemically synthesized

<400> SEQUENCE: 21

Gln Val Gln Leu Val Gln Ser Gly Gly Leu Val Gln Ala Gly Gly
 1               5                  10                  15

Ser Leu Arg Leu Thr Cys Thr Ala Ser Gly Arg Thr Val Ser Asn Tyr
                20                  25                  30

Ala Met Gly Trp Phe Arg Gln Thr Pro Gly Lys Asp Arg Glu Phe Val
            35                  40                  45

Ala Ala Leu Asn Trp Ser Gly Asp Thr Thr Ser Tyr Ala Asp Ser Val
 50                 55                  60

Arg Gly Arg Phe Thr Ile Ser Arg Asp Asn Thr Arg Asn Thr Val Tyr
 65                 70                  75                  80

Leu Gln Met Asp Ser Leu Lys Arg Glu Asp Thr Ala Val Tyr Tyr Cys
                85                  90                  95

Ala Ala Ala Gln Ser Phe Arg Arg Gly Gly Ala Pro Tyr Gly Asp Asn
            100                 105                 110

Tyr Trp Gly Gln Gly Thr Gln Val Thr Val Ser Ser
            115                 120

<210> SEQ ID NO 22
<211> LENGTH: 125
<212> TYPE: PRT
<213> ORGANISM: Artificial Sequence
<220> FEATURE:
<223> OTHER INFORMATION: chemically synthesized

<400> SEQUENCE: 22

Glu Val Gln Leu Leu Glu Ser Gly Gly Leu Val Gln Pro Gly Gly
 1               5                  10                  15

Ser Leu Arg Leu Ser Cys Ala Ala Ser Gly Arg Thr Val Ser Asn Tyr
                20                  25                  30

Ala Met Ser Trp Phe Arg Gln Ala Pro Gly Lys Gly Leu Glu Phe Val
            35                  40                  45

Ser Ala Leu Asn Trp Gly Gly Asp Thr Thr Tyr Tyr Ala Asp Ser Val
 50                 55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Ala Ala Gln Ser Phe Arg Arg Gly Gly Ala Pro Tyr Gly Asp Asn
            100                 105                 110

Tyr Trp Trp Gly Gln Gly Thr Leu Val Thr Val Ser Ser
            115                 120                 125
```

<210> SEQ ID NO 23
<211> LENGTH: 126
<212> TYPE: PRT
<213> ORGANISM: Artificial Sequence
<220> FEATURE:
<223> OTHER INFORMATION: chemically synthesized

<400> SEQUENCE: 23

```
Glu Val Gln Leu Leu Glu Ser Gly Gly Glu Val Gln Pro Gly Gly
1               5                   10                  15

Ser Leu Arg Leu Ser Cys Ala Ala Ser Gly Arg Thr Val Ser Asn Tyr
            20                  25                  30

Ala Met Ser Trp Phe Arg Gln Ala Pro Gly Lys Gly Leu Glu Phe Val
        35                  40                  45

Ser Ala Leu Asn Trp Gly Gly Asp Thr Thr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Ala Gln Ser Phe Arg Arg Gly Gly Ala Pro Tyr Gly Asp Asn
            100                 105                 110

Tyr Trp Gly Gln Gly Thr Leu Val Thr Val Lys Pro Gly Gly
        115                 120                 125
```

<210> SEQ ID NO 24
<211> LENGTH: 124
<212> TYPE: PRT
<213> ORGANISM: Artificial Sequence
<220> FEATURE:
<223> OTHER INFORMATION: chemically synthesized

<400> SEQUENCE: 24

```
Glu Val Gln Leu Val Gln Ser Gly Gly Gly Leu Val Gln Ala Gly Asp
1               5                   10                  15

Ser Leu Arg Leu Ser Cys Ala Ala Ser Gly Arg Ala Leu Thr Gly Tyr
            20                  25                  30

His Met Ala Trp Phe Arg Gln Ala Pro Gly Lys Glu Arg Glu Phe Val
        35                  40                  45

Thr Tyr Gly Ile Trp Asp Arg Ala Gly Ala Ala Tyr Ala Asp Ser Val
    50                  55                  60

Lys Gly Arg Phe Thr Met Ser Arg Asp Asn Ala Lys Asn Thr Val Tyr
65                  70                  75                  80

Leu Gln Met Asn Asn Leu Lys Thr Glu Asp Thr Ala Val Tyr Tyr Cys
                85                  90                  95

Ala Ala Ser Met Ala Val Arg Thr Tyr Tyr Ser Pro Arg Ser Tyr Asp
            100                 105                 110

Ser Trp Gly Gln Gly Thr Gln Val Thr Val Ser Ser
        115                 120
```

<210> SEQ ID NO 25
<211> LENGTH: 124
<212> TYPE: PRT
<213> ORGANISM: Artificial Sequence
<220> FEATURE:
<223> OTHER INFORMATION: chemically synthesized

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Leu Thr Gly Tyr
            20                  25                  30

His Met Ser Trp Phe Arg Gln Ala Pro Gly Lys Gly Arg Glu Phe Val
        35                  40                  45

Ser Tyr Gly Ile Trp Asp Arg Ala Gly Ala Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Met Ala Val Arg Thr Tyr Tyr Ser Pro Arg Ser Tyr Asp
            100                 105                 110

Ser Trp Gly Gln Gly Thr Leu Val Thr Val Ser Ser
            115                 120

<210> SEQ ID NO 26
<211> LENGTH: 124
<212> TYPE: PRT
<213> ORGANISM: Artificial Sequence
<220> FEATURE:
<223> OTHER INFORMATION: chemically synthesized

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Leu Thr Gly Tyr
            20                  25                  30

His Met Ser Trp Phe Arg Gln Ala Pro Gly Lys Gly Leu Glu Phe Val
        35                  40                  45

Ser Tyr Gly Ile Trp Asp Arg Ala Gly Ala Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Met Ala Val Arg Thr Tyr Tyr Ser Pro Arg Ser Tyr Asp
            100                 105                 110

Ser Trp Gly Gln Gly Thr Leu Val Thr Val Ser Ser
            115                 120

<210> SEQ ID NO 27
<211> LENGTH: 128
<212> TYPE: PRT
<213> ORGANISM: Artificial Sequence
<220> FEATURE:
<223> OTHER INFORMATION: chemically synthesized

<400> SEQUENCE: 27

Glu Val Gln Leu Val Gln Ser Gly Gly Gly Leu Val Gln Ala Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Glu Arg Ala Phe Val
        35                  40                  45

Ala Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Glu Asn Thr Thr Tyr
65                  70                  75                  80

Leu Gln Met Asn Ser Leu Lys Pro Glu Asp Ser Ala Val Tyr Tyr Cys
                85                  90                  95

Ala Val Asp Ser Gln Pro Thr Tyr Ser Gly Gly Val Tyr Tyr Pro Arg
            100                 105                 110

Tyr Gly Met Asp Val Trp Gly Gln Gly Thr Gln Val Thr Val Ser Ser
        115                 120                 125

<210> SEQ ID NO 28
<211> LENGTH: 10
<212> TYPE: PRT
<213> ORGANISM: Artificial Sequence
<220> FEATURE:
<223> OTHER INFORMATION: chemically synthesized

<400> SEQUENCE: 28

Ala Ile Arg Trp Asn Glu Gly Asp Thr Tyr
1               5                   10

<210> SEQ ID NO 29
<211> LENGTH: 128
<212> TYPE: PRT
<213> ORGANISM: Artificial Sequence
<220> FEATURE:
<223> OTHER INFORMATION: chemically synthesized

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Asp Ser Gln Pro Thr Tyr Ser Gly Gly Val Tyr Tyr Pro Arg
            100                 105                 110

Tyr Gly Met Asp Val Trp Gly Gln Gly Thr Leu Val Thr Val Ser Ser
        115                 120                 125

<210> SEQ ID NO 30
<211> LENGTH: 128
<212> TYPE: PRT
<213> ORGANISM: Artificial Sequence
<220> FEATURE:
<223> OTHER INFORMATION: chemically synthesized

<400> SEQUENCE: 30

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

-continued

```
Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ser Gln Pro Thr Tyr Ser Gly Gly Val Tyr Tyr Pro Arg
                100                 105                 110

Tyr Gly Met Asp Val Trp Gly Gln Gly Thr Leu Val Thr Val Lys Pro
                115                 120                 125

<210> SEQ ID NO 31
<211> LENGTH: 12
<212> TYPE: PRT
<213> ORGANISM: Artificial Sequence
<220> FEATURE:
<223> OTHER INFORMATION: chemically synthesized

<400> SEQUENCE: 31

Ser Gly Ser Thr Phe Ser Ser Leu Asp Met Ser Trp
1               5                   10

<210> SEQ ID NO 32
<211> LENGTH: 128
<212> TYPE: PRT
<213> ORGANISM: Artificial Sequence
<220> FEATURE:
<223> OTHER INFORMATION: chemically synthesized

<400> SEQUENCE: 32

Glu Val Gln Leu Leu Glu Ser Gly Gly Gly Val Gln Pro Gly Gly
1               5                   10                  15

Ser Leu Arg Leu Ser Cys Ala Ala Ser Gly Ser Thr Phe Ser Ser Leu
                20                  25                  30

Asp Met Gly Trp Phe Arg Gln Ala Pro Gly Lys Gly Arg Glu Phe Val
                35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Thr Gln Pro Thr Tyr Ser Gly Gly Val Tyr Tyr Pro Arg
                100                 105                 110

Tyr Gly Met Asp Val Trp Gly Gln Gly Thr Leu Val Thr Val Lys Pro
                115                 120                 125

<210> SEQ ID NO 33
<211> LENGTH: 128
<212> TYPE: PRT
<213> ORGANISM: Artificial Sequence
<220> FEATURE:
<223> OTHER INFORMATION: chemically synthesized

<400> SEQUENCE: 33

Glu Val Gln Leu Leu Glu Ser Gly Gly Gly Val Gln Pro Gly Gly
1               5                   10                  15

Ser Leu Arg Leu Ser Cys Ala Ala Ser Gly Ser Thr Phe Ser Ser Leu
                20                  25                  30

Asp Met Gly Trp Phe Arg Gln Ala Pro Gly Lys Gly Arg Glu Phe Val
```

```
                    35                  40                  45
Ser Ala Ile Ser Arg Ser Gly Asp Asn Ile Tyr Tyr Ala Glu Ser Val
        50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Tyr Cys
                85                  90                  95
Ala Val Asp Ala Gln Pro Thr Tyr Ser Gly Gly Val Tyr Tyr Pro Arg
            100                 105                 110
Tyr Gly Met Asp Val Trp Gly Gln Gly Thr Leu Val Thr Val Lys Pro
        115                 120                 125
```

<210> SEQ ID NO 34
<211> LENGTH: 128
<212> TYPE: PRT
<213> ORGANISM: Artificial Sequence
<220> FEATURE:
<223> OTHER INFORMATION: chemically synthesized

<400> SEQUENCE: 34

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Thr Phe Ser Ser Leu
            20                  25                  30
Asp Met Gly Trp Phe Arg Gln Ala Pro Gly Lys Gly Arg Glu Phe Val
                35                  40                  45
Ser Ala Ile Ser Arg Ser Gly Asp Asn Ile Tyr Tyr Ala Glu Ser Val
        50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Tyr Cys
                85                  90                  95
Ala Val Glu Ser Gln Pro Thr Tyr Ser Gly Gly Val Tyr Tyr Pro Arg
            100                 105                 110
Tyr Gly Met Asp Val Trp Gly Gln Gly Thr Leu Val Thr Val Lys Pro
        115                 120                 125
```

<210> SEQ ID NO 35
<211> LENGTH: 130
<212> TYPE: PRT
<213> ORGANISM: Artificial Sequence
<220> FEATURE:
<223> OTHER INFORMATION: chemically synthesized

<400> SEQUENCE: 35

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Thr Phe Ser Ser Leu
            20                  25                  30
Asp Met Gly Trp Phe Arg Gln Ala Pro Gly Lys Gly Arg Glu Phe Val
                35                  40                  45
Ser Ala Ile Ser Arg Ser Gly Asp Asn Ile Tyr Tyr Ala Glu Ser Val
        50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Tyr Cys
                85                  90                  95
```

```
Ala Val Asp Ser Gln Pro Thr Tyr Ser Gly Gly Val Tyr Tyr Pro Arg
                100                 105                 110

Tyr Gly Tyr Asp Val Trp Gly Gln Gly Thr Leu Val Thr Val Lys Pro
        115                 120                 125

Gly Gly
    130

<210> SEQ ID NO 36
<211> LENGTH: 130
<212> TYPE: PRT
<213> ORGANISM: Artificial Sequence
<220> FEATURE:
<223> OTHER INFORMATION: chemically synthesized

<400> SEQUENCE: 36

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ser Gln Pro Thr Tyr Ser Gly Gly Val Tyr Tyr Pro Arg
                100                 105                 110

Tyr Gly Asp Asp Val Trp Gly Gln Gly Thr Leu Val Thr Val Lys Pro
        115                 120                 125

Gly Gly
    130

<210> SEQ ID NO 37
<211> LENGTH: 130
<212> TYPE: PRT
<213> ORGANISM: Artificial Sequence
<220> FEATURE:
<223> OTHER INFORMATION: chemically synthesized

<400> SEQUENCE: 37

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ser Gln Pro Thr Tyr Ser Gly Gly Val Tyr Tyr Pro Arg
                100                 105                 110

Tyr Gly Leu Asp Val Trp Gly Gln Gly Thr Leu Val Thr Val Lys Pro
        115                 120                 125
```

Gly Gly
    130

<210> SEQ ID NO 38
<211> LENGTH: 130
<212> TYPE: PRT
<213> ORGANISM: Artificial Sequence
<220> FEATURE:
<223> OTHER INFORMATION: chemically synthesized

<400> SEQUENCE: 38

Glu Val Gln Leu Leu Glu Ser Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Cys Ala Ile Ser Arg Ser Gly Asp Asn Ile Tyr Tyr Ala Glu Ser Val
    50                  55                  60

Lys Gly Arg Phe Thr Cys Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Glu Ser Gln Pro Thr Tyr Ser Gly Val Tyr Tyr Pro Arg
            100                 105                 110

Tyr Gly Met Asp Val Trp Gly Gln Gly Thr Leu Val Thr Val Lys Pro
        115                 120                 125

Gly Gly
    130

<210> SEQ ID NO 39
<211> LENGTH: 130
<212> TYPE: PRT
<213> ORGANISM: Artificial Sequence
<220> FEATURE:
<223> OTHER INFORMATION: chemically synthesized

<400> SEQUENCE: 39

Glu Val Gln Leu Leu Glu Ser Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Val Tyr Tyr Pro Arg
            100                 105                 110

Tyr Gly Ala Asp Val Trp Gly Gln Gly Thr Leu Val Thr Val Lys Pro
        115                 120                 125

Gly Gly
    130

-continued

<210> SEQ ID NO 40
<211> LENGTH: 130
<212> TYPE: PRT
<213> ORGANISM: Artificial Sequence
<220> FEATURE:
<223> OTHER INFORMATION: chemically synthesized

<400> SEQUENCE: 40

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Gly Val Tyr Tyr Pro Arg
            100                 105                 110

Tyr Gly Glu Asp Val Trp Gly Gln Gly Thr Leu Val Thr Val Lys Pro
        115                 120                 125

Gly Gly
    130

<210> SEQ ID NO 41
<211> LENGTH: 130
<212> TYPE: PRT
<213> ORGANISM: Artificial Sequence
<220> FEATURE:
<223> OTHER INFORMATION: chemically synthesized

<400> SEQUENCE: 41

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Gly Val Tyr Tyr Pro Arg
            100                 105                 110

Tyr Gly His Asp Val Trp Gly Gln Gly Thr Leu Val Thr Val Lys Pro
        115                 120                 125

Gly Gly
    130

<210> SEQ ID NO 42
<211> LENGTH: 130
<212> TYPE: PRT
<213> ORGANISM: Artificial Sequence
<220> FEATURE:

<223> OTHER INFORMATION: chemically synthesized

<400> SEQUENCE: 42

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Thr Phe Ser Ser Leu
            20                  25                  30
Asp Met Gly Trp Phe Arg Gln Ala Pro Gly Lys Gly Arg Glu Phe Val
        35                  40                  45
Ser Ala Ile Ser Arg Ser Gly Asp Asn Ile Tyr Tyr Ala Glu Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Tyr Cys
                85                  90                  95
Ala Val Asp Ala Gln Pro Thr Tyr Ser Gly Gly Val Tyr Tyr Pro Arg
            100                 105                 110
Tyr Gly Asn Asp Val Trp Gly Gln Gly Thr Leu Val Thr Val Lys Pro
        115                 120                 125
Gly Gly
    130
```

<210> SEQ ID NO 43
<211> LENGTH: 130
<212> TYPE: PRT
<213> ORGANISM: Artificial Sequence
<220> FEATURE:
<223> OTHER INFORMATION: chemically synthesized

<400> SEQUENCE: 43

```
Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Thr Phe Ser Ser Leu
            20                  25                  30
Asp Met Gly Trp Phe Arg Gln Ala Pro Gly Lys Gly Arg Glu Phe Val
        35                  40                  45
Ser Ala Ile Ser Arg Ser Gly Asp Asn Ile Tyr Tyr Ala Glu Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Arg Ala Glu Asp Thr Ala Val Tyr Tyr Cys
                85                  90                  95
Ala Val Asp Ala Gln Pro Thr Tyr Ser Gly Gly Val Tyr Tyr Pro Arg
            100                 105                 110
Tyr Gly Pro Asp Val Trp Gly Gln Gly Thr Leu Val Thr Val Lys Pro
        115                 120                 125
Gly Gly
    130
```

<210> SEQ ID NO 44
<211> LENGTH: 130
<212> TYPE: PRT
<213> ORGANISM: Artificial Sequence
<220> FEATURE:
<223> OTHER INFORMATION: chemically synthesized

<400> SEQUENCE: 44

```
Glu Val Gln Leu Leu Glu Ser Gly Gly Gly Glu Val Gln Pro Gly Gly
```

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
            35                  40                  45

Ser Ala Ile Ser Arg Ser Gly Asp Asn Ile Tyr Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Val Tyr Tyr Pro Arg
            100                 105                 110

Tyr Gly Gln Asp Val Trp Gly Gln Gly Thr Leu Val Thr Val Lys Pro
            115                 120                 125

Gly Gly
    130

<210> SEQ ID NO 45
<211> LENGTH: 130
<212> TYPE: PRT
<213> ORGANISM: Artificial Sequence
<220> FEATURE:
<223> OTHER INFORMATION: chemically synthesized

<400> SEQUENCE: 45

Glu Val Gln Leu Leu Glu Ser Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
            35                  40                  45

Ser Ala Ile Ser Arg Ser Gly Asp Asn Ile Tyr Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Val Tyr Tyr Pro Arg
            100                 105                 110

Tyr Gly Arg Asp Val Trp Gly Gln Gly Thr Leu Val Thr Val Lys Pro
            115                 120                 125

Gly Gly
    130

<210> SEQ ID NO 46
<211> LENGTH: 130
<212> TYPE: PRT
<213> ORGANISM: Artificial Sequence
<220> FEATURE:
<223> OTHER INFORMATION: chemically synthesized

<400> SEQUENCE: 46

Glu Val Gln Leu Leu Glu Ser Gly Gly Glu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
            35                  40                  45

Ser Ala Ile Ser Arg Ser Gly Asp Asn Ile Tyr Tyr Ala Glu Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Val Tyr Pro Arg
            100                 105                 110

Tyr Gly Ser Asp Val Trp Gly Gln Gly Thr Leu Val Thr Val Lys Pro
            115                 120                 125

Gly Gly
    130

<210> SEQ ID NO 47
<211> LENGTH: 130
<212> TYPE: PRT
<213> ORGANISM: Artificial Sequence
<220> FEATURE:
<223> OTHER INFORMATION: chemically synthesized

<400> SEQUENCE: 47

Glu Val Gln Leu Leu Glu Ser Gly Gly Gly Glu Val Gln Pro Gly Gly
 1               5                   10                  15

Ser Leu Arg Leu Ser Cys Ala Ala Ser Gly Ser Thr Phe Ser Ser Leu
                20                  25                  30

Asp Met Gly Trp Phe Arg Gln Ala Pro Gly Lys Gly Arg Glu Phe Val
            35                  40                  45

Ser Ala Ile Ser Arg Ser Gly Asp Asn Ile Tyr Tyr Ala Glu Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Val Tyr Pro Arg
            100                 105                 110

Tyr Gly Thr Asp Val Trp Gly Gln Gly Thr Leu Val Thr Val Lys Pro
            115                 120                 125

Gly Gly
    130

<210> SEQ ID NO 48
<211> LENGTH: 130
<212> TYPE: PRT
<213> ORGANISM: Artificial Sequence
<220> FEATURE:
<223> OTHER INFORMATION: chemically synthesized

<400> SEQUENCE: 48

Glu Val Gln Leu Leu Glu Ser Gly Gly Gly Glu Val Gln Pro Gly Gly
 1               5                   10                  15

Ser Leu Arg Leu Ser Cys Ala Ala Ser Gly Ser Thr Phe Ser Ser Leu
                20                  25                  30

Asp Met Gly Trp Phe Arg Gln Ala Pro Gly Lys Gly Arg Glu Phe Val
            35                  40                  45

Ser Ala Ile Ser Arg Ser Gly Asp Asn Ile Tyr Tyr Ala Glu Ser Val
 50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Asp Ala Gln Pro Thr Tyr Ser Gly Gly Val Tyr Tyr Pro Arg
            100                 105                 110

Tyr Gly Val Asp Val Trp Gly Gln Gly Thr Leu Val Thr Val Lys Pro
        115                 120                 125

Gly Gly
    130

<210> SEQ ID NO 49
<211> LENGTH: 124
<212> TYPE: PRT
<213> ORGANISM: Artificial Sequence
<220> FEATURE:
<223> OTHER INFORMATION: chemically synthesized

<400> SEQUENCE: 49

Glu Val Gln Leu Val Gln Ser Gly Gly Gly Leu Val Gln Ala Gly Gly
1               5                   10                  15

Ser Leu Arg Leu Ser Cys Ala Ala Ser Gly Arg Ala Phe Ser Asn Tyr
            20                  25                  30

Ala Leu Gly Trp Phe Arg Gln Ala Pro Gly Lys Glu Arg Glu Phe Ile
        35                  40                  45

Ala Ala Ile Asn Trp Asn Gly Glu Asn Arg Tyr Gly Val Asp Ser Val
    50                  55                  60

Lys Gly Arg Phe Thr Ile Ser Arg Asp Asn Ala Gln Asn Met Gly Tyr
65                  70                  75                  80

Leu Gln Met Asn Asn Leu Lys Pro Glu Asp Thr Ala Val Tyr Arg Cys
                85                  90                  95

Ala Ala Ala Leu Ser Phe Arg Leu Gly Gly Glu Pro Tyr Gly Asp Ala
            100                 105                 110

Tyr Trp Gly Gln Gly Thr Gln Val Thr Val Ser Ser
        115                 120

<210> SEQ ID NO 50
<211> LENGTH: 124
<212> TYPE: PRT
<213> ORGANISM: Artificial Sequence
<220> FEATURE:
<223> OTHER INFORMATION: chemically synthesized

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Phe Ser Asn Tyr
            20                  25                  30

Ala Met Ser Trp Phe Arg Gln Ala Pro Gly Lys Gly Leu Glu Phe Val
        35                  40                  45

Ser Ala Ile Asn Trp Asn Gly Glu Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Leu Ser Phe Arg Leu Gly Gly Glu Pro Tyr Gly Asp Ala

Tyr Trp Gly Gln Gly Thr Leu Val Thr Val Ser Ser
            115                 120

<210> SEQ ID NO 51
<211> LENGTH: 122
<212> TYPE: PRT
<213> ORGANISM: Artificial Sequence
<220> FEATURE:
<223> OTHER INFORMATION: chemically synthesized

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Ile Phe Thr Asn Asn
            20                  25                  30

Ala Met Gly Trp Tyr Arg Gln Ala Pro Gly Lys Gln Arg Asp Leu Val
        35                  40                  45

Ala Gln Ile Thr Met Gly Gly Ile Thr Asn Tyr Ala Pro Ser Met
    50                  55                  60

Glu Gly Arg Phe Ala Ile Ser Arg Asp Asn Ala Lys Ser Thr Val Tyr
65                  70                  75                  80

Leu Gln Met Asn Asn Leu Lys Pro Glu Asp Thr Ala Val Tyr Tyr Cys
                85                  90                  95

Asn Ala Glu Val Lys Ser Ala Asp Trp Gly Ala Tyr Ala Asn Tyr Trp
            100                 105                 110

Gly Gln Gly Thr Gln Val Thr Val Ser Ser
        115                 120

<210> SEQ ID NO 52
<211> LENGTH: 122
<212> TYPE: PRT
<213> ORGANISM: Artificial Sequence
<220> FEATURE:
<223> OTHER INFORMATION: chemically synthesized

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Phe Thr Asn Asn
            20                  25                  30

Ala Met Ser Trp Tyr Arg Gln Ala Pro Gly Lys Gly Leu Glu Leu Val
        35                  40                  45

Ser Ala Ile Thr Met Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Asn Ala Glu Val Lys Ser Ala Asp Trp Gly Ala Tyr Ala Asn Tyr Trp
            100                 105                 110

Gly Gln Gly Thr Leu Val Thr Val Ser Ser
        115                 120

<210> SEQ ID NO 53
<211> LENGTH: 122
<212> TYPE: PRT
<213> ORGANISM: Artificial Sequence
<220> FEATURE:

<223> OTHER INFORMATION: chemically synthesized

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Phe Thr Asn Asn
            20                  25                  30

Ala Met Ser Trp Tyr Arg Gln Ala Pro Gly Lys Gly Arg Glu Leu Val
        35                  40                  45

Ser Gln Ile Thr Met Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Asn Ala Glu Val Lys Ser Ala Asp Trp Gly Ala Tyr Ala Asn Tyr Trp
            100                 105                 110

Gly Gln Gly Thr Leu Val Thr Val Ser Ser
        115                 120

<210> SEQ ID NO 54
<211> LENGTH: 125
<212> TYPE: PRT
<213> ORGANISM: Artificial Sequence
<220> FEATURE:
<223> OTHER INFORMATION: chemically synthesized

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Leu
        35                  40                  45

Ala Ala Ser Val Trp Asn Asn Gly Gly Asn Tyr Tyr Ala Asp Ser Val
    50                  55                  60

Lys Gly Arg Phe Thr Ala Ser Arg Asp Asp Ala Lys Ser Thr Ala Tyr
65                  70                  75                  80

Leu Gln Met Ser Arg Leu Arg Pro Glu Asp Thr Gly Ile Tyr Tyr Cys
                85                  90                  95

Val Val Ala Arg Thr Pro Glu Thr Pro Ile Thr Ser Arg Gly Ala
            100                 105                 110

Asn Tyr Trp Gly Gln Gly Thr Gln Val Thr Val Ser Ser
        115                 120                 125

<210> SEQ ID NO 55
<211> LENGTH: 125
<212> TYPE: PRT
<213> ORGANISM: Artificial Sequence
<220> FEATURE:
<223> OTHER INFORMATION: chemically synthesized

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val

```
                    35                  40                  45

Ser Ala Ser Val Trp Asn Asn Gly Gly Asn Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
                100                 105                 110

Asn Tyr Trp Gly Gln Gly Thr Leu Val Thr Val Ser Ser
                115                 120                 125
```

<210> SEQ ID NO 56
<211> LENGTH: 127
<212> TYPE: PRT
<213> ORGANISM: Artificial Sequence
<220> FEATURE:
<223> OTHER INFORMATION: chemically synthesized

<400> SEQUENCE: 56

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ser Ile Ser Asn Tyr
                20                  25                  30

Ala Met Gly Trp Phe Arg Gln Ala Pro Gly Lys Glu Arg Glu Phe Val
                35                  40                  45

Ser Ala Ser Val Trp Asn Asn Gly Gly Asn Tyr Tyr Ala Glu Ser Val
                50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
                100                 105                 110

Asn Tyr Trp Gly Gln Gly Thr Leu Val Thr Val Lys Pro Gly Gly
                115                 120                 125
```

<210> SEQ ID NO 57
<211> LENGTH: 127
<212> TYPE: PRT
<213> ORGANISM: Artificial Sequence
<220> FEATURE:
<223> OTHER INFORMATION: chemically synthesized

<400> SEQUENCE: 57

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ser Ile Ser Asn Tyr
                20                  25                  30

Ala Met Gly Trp Phe Arg Gln Ala Pro Gly Lys Glu Arg Glu Phe Val
                35                  40                  45

Ser Ala Ser Val Trp Asn Asn Gly Gly Asn Tyr Tyr Ala Glu Ser Val
                50                  55                  60

Lys Gly Arg Phe Thr Ile Ser Arg Asp Asp Ala Lys Ser Thr Leu Tyr
65                  70                  75                  80

Leu Gln Met Ser Ser Leu Arg Ala Glu Asp Thr Ala Val Tyr Tyr Cys
                85                  90                  95
```

```
Val Val Ala Arg Thr Pro Glu Thr Pro Ile Thr Ser Ala Arg Gly Ala
            100                 105                 110

Asn Tyr Trp Gly Gln Gly Thr Leu Val Thr Val Lys Pro Gly Gly
        115                 120                 125
```

<210> SEQ ID NO 58
<211> LENGTH: 127
<212> TYPE: PRT
<213> ORGANISM: Artificial Sequence
<220> FEATURE:
<223> OTHER INFORMATION: chemically synthesized

<400> SEQUENCE: 58

```
Glu Val Gln Leu Leu Glu Ser Gly Gly Gly Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val
        35                  40                  45

Ser Ala Ser Val Trp Asn Gln Gly Gly Asn Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Lys Pro Gly Gly
        115                 120                 125
```

<210> SEQ ID NO 59
<211> LENGTH: 127
<212> TYPE: PRT
<213> ORGANISM: Artificial Sequence
<220> FEATURE:
<223> OTHER INFORMATION: chemically synthesized

<400> SEQUENCE: 59

```
Glu Val Gln Leu Leu Glu Ser Gly Gly Gly Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val
        35                  40                  45

Ser Ala Ser Val Trp Asn Asn Ala Gly Asn Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Lys Pro Gly Gly
        115                 120                 125
```

<210> SEQ ID NO 60
<211> LENGTH: 127
<212> TYPE: PRT
<213> ORGANISM: Artificial Sequence
<220> FEATURE:
<223> OTHER INFORMATION: chemically synthesized

<400> SEQUENCE: 60

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val
        35                  40                  45

Ser Ala Ser Val Trp Asn Gln Gly Asn Tyr Tyr Ala Glu Ser Val
    50                  55                  60

Lys Gly Arg Phe Thr Ile Ser Arg Asp Asp Ala Lys Ser Thr Leu Tyr
65                  70                  75                  80

Leu Gln Met Ser Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Lys Pro Gly Gly
        115                 120                 125

<210> SEQ ID NO 61
<211> LENGTH: 127
<212> TYPE: PRT
<213> ORGANISM: Artificial Sequence
<220> FEATURE:
<223> OTHER INFORMATION: chemically synthesized

<400> SEQUENCE: 61

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val
        35                  40                  45

Ser Ala Ser Val Trp Asn Asn Ala Gly Asn Tyr Tyr Ala Glu Ser Val
    50                  55                  60

Lys Gly Arg Phe Thr Ile Ser Arg Asp Asp Ala Lys Ser Thr Leu Tyr
65                  70                  75                  80

Leu Gln Met Ser Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Lys Pro Gly Gly
        115                 120                 125

<210> SEQ ID NO 62
<211> LENGTH: 127
<212> TYPE: PRT
<213> ORGANISM: Artificial Sequence
<220> FEATURE:
<223> OTHER INFORMATION: chemically synthesized

<400> SEQUENCE: 62

Gln Val Gln Leu Gln Glu Ser Gly Gly Gly Ser Val Gln Ala Gly Gly
1               5                   10                  15

Ser Leu Thr Leu Ser Cys Ala Ala Ser Gly Arg Ala Ala Ser Asp Tyr
            20                  25                  30

Ala Val Gly Trp Phe Arg Gln Ala Pro Gly Lys Glu Arg Glu Phe Val
            35                  40                  45

Ala Ala Cys Asn Trp Ser Gly Glu Asp Thr Val Tyr Ala Tyr Ile Val
 50                  55                  60

Lys Gly Arg Phe Thr Ile Ser Arg Asp Asn Ala Gly Asn Thr Val Ser
 65                  70                  75                  80

Leu Arg Met Ser Ser Leu Glu Pro Glu Asp Thr Ala Val Tyr Tyr Cys
                 85                  90                  95

Ala Ala Ala Pro Ser Phe Ser Arg Ser Val Leu Asp Gly Asn Leu Ser
            100                 105                 110

Gln Ile Asp Tyr Trp Gly Gln Gly Thr Gln Val Thr Val Ser Ser
            115                 120                 125

<210> SEQ ID NO 63
<211> LENGTH: 127
<212> TYPE: PRT
<213> ORGANISM: Artificial Sequence
<220> FEATURE:
<223> OTHER INFORMATION: chemically synthesized

<400> SEQUENCE: 63

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Arg Ala Ala Ser Asp Tyr
             20                  25                  30

Ala Met Ser Trp Phe Arg Gln Ala Pro Gly Lys Gly Leu Glu Phe Val
            35                  40                  45

Ser Ala Ile Asn Trp Gly Gly Glu Asp Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Ala Pro Ser Phe Ser Arg Ser Val Leu Asp Gly Asn Leu Ser
            100                 105                 110

Gln Ile Asp Tyr Trp Gly Gln Gly Thr Leu Val Thr Val Ser Ser
            115                 120                 125

<210> SEQ ID NO 64
<211> LENGTH: 124
<212> TYPE: PRT
<213> ORGANISM: Artificial Sequence
<220> FEATURE:
<223> OTHER INFORMATION: chemically synthesized

<400> SEQUENCE: 64

Gln Val Gln Leu Val Gln Ser Gly Gly Gly Leu Ala Gln Ala Gly Gly
 1               5                  10                  15

Ser Leu Arg Leu Ser Cys Val Ala Ser Gly Arg Thr Phe Thr Asn Tyr
             20                  25                  30

Ala Met Gly Trp Phe Arg Gln Ala Pro Gly Lys Glu Arg Glu Phe Val
            35                  40                  45

Ala Ala Ile Asn Trp Ser Gly Asp Ser Thr Tyr His Ala Asp Ser Val
 50                  55                  60

Lys Gly Arg Phe Thr Ile Ser Arg Asp Asn Ala Lys Asp Ser Val Tyr
 65                  70                  75                  80

Leu Gln Met Thr Lys Leu Lys Pro Glu Asp Thr Ala Asp Tyr Tyr Cys
                 85                  90                  95

Ala Ser Ala Glu Ser Phe Ser Arg Gly Gly Leu Pro Tyr Gly Met Asn
            100                 105                 110

Tyr Trp Gly Gln Gly Thr Gln Val Thr Val Ser Ser
        115                 120

<210> SEQ ID NO 65
<211> LENGTH: 124
<212> TYPE: PRT
<213> ORGANISM: Artificial Sequence
<220> FEATURE:
<223> OTHER INFORMATION: chemically synthesized

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Thr Asn Tyr
            20                  25                  30

Ala Met Ser Trp Phe Arg Gln Ala Pro Gly Lys Gly Leu Glu Phe Val
        35                  40                  45

Ser Ala Ile Asn Trp Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Ala Glu Ser Phe Ser Arg Gly Gly Leu Pro Tyr Gly Met Asn
            100                 105                 110

Tyr Trp Gly Gln Gly Thr Leu Val Thr Val Ser Ser
        115                 120

<210> SEQ ID NO 66
<211> LENGTH: 126
<212> TYPE: PRT
<213> ORGANISM: Artificial Sequence
<220> FEATURE:
<223> OTHER INFORMATION: chemically synthesized

<400> SEQUENCE: 66

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Thr Phe Thr Asn Tyr
            20                  25                  30

Ala Met Ser Trp Phe Arg Gln Ala Pro Gly Lys Gly Leu Glu Phe Val
        35                  40                  45

Ser Ala Ile Asn Trp Ser Gly Asp Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
            85                  90                  95

Ala Ser Ala Glu Ser Phe Ser Arg Gly Gly Leu Pro Tyr Gly Met Asn
            100                 105                 110

Tyr Trp Gly Gln Gly Thr Leu Val Thr Val Lys Pro Gly Gly
        115                 120                 125

<210> SEQ ID NO 67
<211> LENGTH: 126
<212> TYPE: PRT

```
<213> ORGANISM: Artificial Sequence
<220> FEATURE:
<223> OTHER INFORMATION: chemically synthesized

<400> SEQUENCE: 67

Gln Val Gln Leu Val Gln Ser Gly Gly Gly Leu Val Gln Ala Gly Gly
1               5                   10                  15

Ser Leu Thr Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Asp Gly Val Gly Ala Tyr Tyr Ala Asp Ser Val
    50                  55                  60

Arg Gly Arg Phe Lys Asn Ser Lys Asp Asn Ala Lys Arg Thr Ala Tyr
65                  70                  75                  80

Leu Gln Met Asn Arg Leu Lys Pro Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Gln Val Thr Val Ser Ser
        115                 120                 125

<210> SEQ ID NO 68
<211> LENGTH: 126
<212> TYPE: PRT
<213> ORGANISM: Artificial Sequence
<220> FEATURE:
<223> OTHER INFORMATION: chemically synthesized

<400> SEQUENCE: 68

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Glu Gly Val Gly Ala Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Leu Val Thr Val Lys Pro
        115                 120                 125

<210> SEQ ID NO 69
<211> LENGTH: 126
<212> TYPE: PRT
<213> ORGANISM: Artificial Sequence
<220> FEATURE:
<223> OTHER INFORMATION: chemically synthesized

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Val Ser Thr Phe Gly Thr Ser
            20                  25                  30
```

Pro Val Gly Trp Phe Arg Gln Ala Pro Gly Lys Glu Arg Glu Phe Val
            35                  40                  45

Ser Ala Ile Arg Trp Asp Gly Val Gly Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Leu Val Thr Val Ser Ser
            115                 120                 125

<210> SEQ ID NO 70
<211> LENGTH: 128
<212> TYPE: PRT
<213> ORGANISM: Artificial Sequence
<220> FEATURE:
<223> OTHER INFORMATION: chemically synthesized

<400> SEQUENCE: 70

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
            35                  40                  45

Ser Ala Ile Arg Trp Asp Gly Val Gly Ala Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Leu Val Thr Val Lys Pro Gly Gly
            115                 120                 125

<210> SEQ ID NO 71
<211> LENGTH: 128
<212> TYPE: PRT
<213> ORGANISM: Artificial Sequence
<220> FEATURE:
<223> OTHER INFORMATION: chemically synthesized

<400> SEQUENCE: 71

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
            35                  40                  45

Cys Ala Ile Arg Trp Glu Gly Val Gly Ala Tyr Tyr Ala Glu Ser Val
    50                  55                  60

Lys Gly Arg Phe Thr Cys Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys

```
                            85                  90                  95

Ala Leu Pro Arg Arg Gly Asp Ser Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

<210> SEQ ID NO 72
<211> LENGTH: 128
<212> TYPE: PRT
<213> ORGANISM: Artificial Sequence
<220> FEATURE:
<223> OTHER INFORMATION: chemically synthesized

<400> SEQUENCE: 72

Glu Val Gln Leu Leu Glu Ser Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
            35                  40                  45

Ser Ala Ile Arg Trp Asp Ala Val Gly Ala Tyr Tyr Ala Glu Ser Val
        50                  55                  60

Lys Gly Arg Phe Thr Ile Ser Lys Asp Asn Ala Lys Arg Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ser Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

<210> SEQ ID NO 73
<211> LENGTH: 128
<212> TYPE: PRT
<213> ORGANISM: Artificial Sequence
<220> FEATURE:
<223> OTHER INFORMATION: chemically synthesized

<400> SEQUENCE: 73

Glu Val Gln Leu Leu Glu Ser Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
            35                  40                  45

Ser Ala Ile Arg Trp Asp Gly Val Gly Ala Tyr Tyr Ala Glu Ser Val
        50                  55                  60

Lys Gly Arg Phe Thr Ile Ser Lys Asp Asn Ala Lys Arg Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Glu Ser Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

<210> SEQ ID NO 74
<211> LENGTH: 128
```

```
<212> TYPE: PRT
<213> ORGANISM: Artificial Sequence
<220> FEATURE:
<223> OTHER INFORMATION: chemically synthesized

<400> SEQUENCE: 74

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Asp Gly Val Gly Ala Tyr Tyr Ala Glu Ser Val
    50                  55                  60

Lys Gly Arg Phe Thr Ile Ser Lys Asp Asn Ala Lys Arg Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ala Glu Leu Pro Ser Thr Val Lys Glu
            100                 105                 110

Tyr Gly Tyr Trp Gly Gln Gly Thr Leu Val Thr Val Lys Pro Gly Gly
        115                 120                 125

<210> SEQ ID NO 75
<211> LENGTH: 128
<212> TYPE: PRT
<213> ORGANISM: Artificial Sequence
<220> FEATURE:
<223> OTHER INFORMATION: chemically synthesized

<400> SEQUENCE: 75

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Asp Gly Val Gly Ala Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Leu Val Thr Val Lys Pro Gly Gly
        115                 120                 125

<210> SEQ ID NO 76
<211> LENGTH: 128
<212> TYPE: PRT
<213> ORGANISM: Artificial Sequence
<220> FEATURE:
<223> OTHER INFORMATION: chemically synthesized

<400> SEQUENCE: 76

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
```

```
            20                  25                  30
Pro Val Gly Trp Phe Arg Gln Ala Pro Gly Lys Glu Arg Glu Phe Val
        35                  40                  45

Ser Ala Ile Arg Trp Glu Gly Val Gly Ala Tyr Tyr Ala Glu Ser Val
        50                  55                  60

Lys Gly Arg Phe Thr Ile Ser Lys Asp Asn Ala Lys Arg Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Glu Ser Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

<210> SEQ ID NO 77
<211> LENGTH: 128
<212> TYPE: PRT
<213> ORGANISM: Artificial Sequence
<220> FEATURE:
<223> OTHER INFORMATION: chemically synthesized

<400> SEQUENCE: 77

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Glu Gly Val Gly Ala Tyr Tyr Ala Glu Ser Val
        50                  55                  60

Lys Gly Arg Phe Thr Ile Ser Lys Asp Asn Ala Lys Arg Thr Leu Tyr
65                  70                  75                  80

Leu Gln Met Ser Ser Leu Arg Ala Glu Asp Thr Ala Val Tyr Tyr Cys
                85                  90                  95

Ala Leu Pro Arg Arg Gly Asp Ala Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

<210> SEQ ID NO 78
<211> LENGTH: 128
<212> TYPE: PRT
<213> ORGANISM: Artificial Sequence
<220> FEATURE:
<223> OTHER INFORMATION: chemically synthesized

<400> SEQUENCE: 78

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Asp Ala Val Gly Ala Tyr Tyr Ala Glu Ser Val
        50                  55                  60

Lys Gly Arg Phe Thr Ile Ser Lys Asp Asn Ala Lys Arg Thr Leu Tyr
65                  70                  75                  80
```

```
Leu Gln Met Ser Ser Leu Arg Ala Glu Asp Thr Ala Val Tyr Tyr Cys
                85                  90                  95

Ala Leu Pro Arg Arg Gly Glu Ser Glu Leu Pro Ser Thr Val Lys Glu
            100                 105                 110

Tyr Gly Tyr Trp Gly Gln Gly Thr Leu Val Thr Val Lys Pro Gly Gly
        115                 120                 125
```

<210> SEQ ID NO 79
<211> LENGTH: 121
<212> TYPE: PRT
<213> ORGANISM: Artificial Sequence
<220> FEATURE:
<223> OTHER INFORMATION: chemically synthesized

<400> SEQUENCE: 79

```
Gln Leu Gln Leu Gln Glu Ser Gly Gly Gly Leu Val Gln Ala Gly Asp
1               5                   10                  15

Ser Leu Arg Leu Ser Cys Gln Val Ser Gly Arg Thr Leu Ser Ala Tyr
            20                  25                  30

Leu Met Ala Trp Phe Arg Gln Ala Pro Asn Lys Val Arg Glu Tyr Leu
        35                  40                  45

Gly Arg Ile Arg Trp Asn Glu Gly Asp Thr Tyr Tyr Pro Asp Ser Val
    50                  55                  60

Lys Gly Arg Phe Thr Ile Ser Lys Asp Ala Lys Asn Thr Val Tyr
65                  70                  75                  80

Leu Arg Met Asn Ser Leu Lys Pro Glu Asp Thr Ala Val Tyr Tyr Cys
                85                  90                  95

Ala Ala Arg Ser Ile Phe Asn Pro Ser Asp Gln Tyr Val Tyr Trp Gly
            100                 105                 110

Gln Gly Thr Gln Val Thr Val Ser Ser
        115                 120
```

<210> SEQ ID NO 80
<211> LENGTH: 121
<212> TYPE: PRT
<213> ORGANISM: Artificial Sequence
<220> FEATURE:
<223> OTHER INFORMATION: chemically synthesized

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Leu Ser Ala Tyr
            20                  25                  30

Leu Met Ser Trp Phe Arg Gln Ala Pro Gly Lys Gly Leu Glu Tyr Val
        35                  40                  45

Ser Ala Ile Arg Trp Asn Glu Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Ser Ile Phe Asn Pro Ser Asp Gln Tyr Val Tyr Trp Gly
            100                 105                 110

Gln Gly Thr Leu Val Thr Val Ser Ser
        115                 120
```

<210> SEQ ID NO 81

<211> LENGTH: 121
<212> TYPE: PRT
<213> ORGANISM: Artificial Sequence
<220> FEATURE:
<223> OTHER INFORMATION: chemically synthesized

<400> SEQUENCE: 81

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Val | Ser | Gly | Arg | Thr | Leu | Ser | Ala | Tyr |
| | | | 20 | | | | | 25 | | | | | 30 | | |

| Leu | Met | Ser | Trp | Phe | Arg | Gln | Ala | Pro | Gly | Lys | Gly | Arg | Glu | Tyr | Val |
| | | 35 | | | | | 40 | | | | | 45 | | | |

| Ser | Arg | Ile | Arg | Trp | Asn | Glu | Gly | Asp | Thr | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Lys | Ala | Glu | Asp | Thr | Ala | Val | Tyr | Tyr | Cys |
| | | | | 85 | | | | | 90 | | | | | 95 | |

| Ala | Ala | Arg | Ser | Ile | Phe | Asn | Pro | Ser | Asp | Gln | Tyr | Val | Tyr | Trp | Gly |
| | | | 100 | | | | | 105 | | | | | 110 | | |

| Gln | Gly | Thr | Leu | Val | Thr | Val | Ser | Ser |
|---|---|---|---|---|---|---|---|---|
| | | | 115 | | | | 120 | |

<210> SEQ ID NO 82
<211> LENGTH: 128
<212> TYPE: PRT
<213> ORGANISM: Artificial Sequence
<220> FEATURE:
<223> OTHER INFORMATION: chemically synthesized

<400> SEQUENCE: 82

| Glu | Val | Gln | Leu | Val | Gln | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Ser | Thr | Phe | Ser | Ser | Leu |
| | | | 20 | | | | | 25 | | | | | 30 | | |

| Asp | Met | Gly | Trp | Phe | Arg | Gln | Ala | Pro | Gly | Lys | Glu | Arg | Ala | Phe | Val |
| | | 35 | | | | | 40 | | | | | 45 | | | |

| Ala | Ala | Ile | Ser | Arg | Ser | Gly | Asp | Asn | Ile | Tyr | Tyr | Ala | Glu | Ser | Val |
| | 50 | | | | | 55 | | | | | 60 | | | | |

| Lys | Gly | Arg | Phe | Thr | Ile | Ser | Arg | Asp | Asn | Ala | Glu | Asn | Thr | Met | Tyr |
| 65 | | | | | 70 | | | | | 75 | | | | | 80 |

| Leu | Gln | Met | Asn | Ser | Leu | Lys | Pro | Glu | Asp | Ser | Ala | Val | Tyr | Tyr | Cys |
| | | | | 85 | | | | | 90 | | | | | 95 | |

| Ala | Val | Glu | Ser | Gln | Pro | Thr | Tyr | Ser | Gly | Val | Tyr | Tyr | Pro | Arg |
| | | | 100 | | | | | 105 | | | | | 110 | |

| Tyr | Gly | Met | Asp | Val | Trp | Gly | Gln | Gly | Thr | Gln | Val | Thr | Val | Ser | Ser |
| | | 115 | | | | | 120 | | | | | 125 | | | |

<210> SEQ ID NO 83
<211> LENGTH: 128
<212> TYPE: PRT
<213> ORGANISM: Artificial Sequence
<220> FEATURE:
<223> OTHER INFORMATION: chemically synthesized

<400> SEQUENCE: 83

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

```
Ser Leu Arg Leu Ser Cys Ala Ala Ser Gly Ser Thr Phe Ser Ser Leu
            20                  25                  30

Asp Met Ser Trp Phe Arg Gln Ala Pro Gly Lys Gly Leu Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Val Glu Ser Gln Pro Thr Tyr Ser Gly Gly Val Tyr Tyr Pro Arg
        100                 105                 110

Tyr Gly Met Asp Val Trp Gly Gln Gly Thr Leu Val Thr Val Ser Ser
        115                 120                 125

<210> SEQ ID NO 84
<211> LENGTH: 128
<212> TYPE: PRT
<213> ORGANISM: Artificial Sequence
<220> FEATURE:
<223> OTHER INFORMATION: chemically synthesized

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Val Glu Ser Gln Pro Thr Tyr Ser Gly Gly Val Tyr Tyr Pro Arg
        100                 105                 110

Tyr Gly Met Asp Val Trp Gly Gln Gly Thr Leu Val Thr Val Ser Ser
        115                 120                 125

<210> SEQ ID NO 85
<211> LENGTH: 123
<212> TYPE: PRT
<213> ORGANISM: Artificial Sequence
<220> FEATURE:
<223> OTHER INFORMATION: chemically synthesized

<400> SEQUENCE: 85

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Val
        35                  40                  45

Ser Ala Ile Tyr Trp Ser Gly Gly Thr Val Phe Tyr Ala Glu Ser Val
    50                  55                  60

Lys Gly Arg Phe Thr Ile Ser Arg Asp Asn Ala Lys Asn Thr Val Tyr
65                  70                  75                  80
```

```
Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
        115                 120
```

<210> SEQ ID NO 86
<211> LENGTH: 123
<212> TYPE: PRT
<213> ORGANISM: Artificial Sequence
<220> FEATURE:
<223> OTHER INFORMATION: chemically synthesized

<400> SEQUENCE: 86

```
Glu Val Gln Leu Leu Glu Ser Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Leu
        35                  40                  45

Ala Val Ile Tyr Trp Ser Gly Thr Val Phe Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
        115                 120
```

<210> SEQ ID NO 87
<211> LENGTH: 123
<212> TYPE: PRT
<213> ORGANISM: Artificial Sequence
<220> FEATURE:
<223> OTHER INFORMATION: chemically synthesized

<400> SEQUENCE: 87

```
Glu Val Gln Leu Leu Glu Ser Gly Gly Gly Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Val
        35                  40                  45

Ser Ala Ile Tyr Trp Ser Gly Thr Val Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
        115                 120
```

```
<210> SEQ ID NO 88
<211> LENGTH: 123
<212> TYPE: PRT
<213> ORGANISM: Artificial Sequence
<220> FEATURE:
<223> OTHER INFORMATION: chemically synthesized

<400> SEQUENCE: 88
```

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Leu
        35                  40                  45

Ala Val Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
        115                 120

```
<210> SEQ ID NO 89
<211> LENGTH: 123
<212> TYPE: PRT
<213> ORGANISM: Artificial Sequence
<220> FEATURE:
<223> OTHER INFORMATION: chemically synthesized

<400> SEQUENCE: 89
```

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Val
        35                  40                  45

Ser Ala Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
        115                 120

```
<210> SEQ ID NO 90
<211> LENGTH: 123
<212> TYPE: PRT
<213> ORGANISM: Artificial Sequence
<220> FEATURE:
<223> OTHER INFORMATION: chemically synthesized

<400> SEQUENCE: 90
```

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Leu
            35                  40                  45

Ala Val Ile Tyr Trp Ser Gly Gly Thr Val Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro
            115                 120

<210> SEQ ID NO 91
<211> LENGTH: 124
<212> TYPE: PRT
<213> ORGANISM: Artificial Sequence
<220> FEATURE:
<223> OTHER INFORMATION: chemically synthesized

<400> SEQUENCE: 91

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Thr Val Ser Asn Tyr
            20                  25                  30

Ala Met Gly Trp Phe Arg Gln Ala Pro Gly Lys Asp Arg Glu Phe Val
            35                  40                  45

Ser Ala Leu Asn Trp Gly Gly Asp Thr Thr Tyr Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Ala Gln Ser Phe Arg Arg Gly Gly Ala Pro Tyr Gly Asp Asn
            100                 105                 110

Tyr Trp Gly Gln Gly Thr Leu Val Thr Val Lys Pro
            115                 120

<210> SEQ ID NO 92
<211> LENGTH: 256
<212> TYPE: PRT
<213> ORGANISM: Artificial Sequence
<220> FEATURE:
<223> OTHER INFORMATION: chemically synthesized

<400> SEQUENCE: 92

Glu Val Gln Leu Leu Glu Ser Gly Gly Gly Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
            35                  40                  45

Cys Ala Ile Tyr Trp Ser Gly Gly Thr Val Tyr Ala Glu Ser Val
        50                  55                  60

Lys Gly Arg Phe Thr Cys Ser Arg Asp Asn Ala Lys Asn Thr Leu Tyr

```
                65                  70                  75                  80
Leu Gln Met Ser Ser Leu Arg Ala Glu Asp Thr Ala Val Tyr Tyr Cys
                    85                  90                  95

Ala Val Thr Ile Arg Gly Ala Ala Thr Gln Thr Trp Lys Tyr Asp Tyr
                100                 105                 110

Trp Gly Gln Gly Thr Leu Val Thr Val Lys Pro Gly Gly Ser Gly Gly
            115                 120                 125

Ser Glu Val Gln Leu Leu Glu Ser Gly Gly Glu Val Gln Pro Gly
    130                 135                 140

Gly Ser Leu Arg Leu Ser Cys Ala Ala Ser Gly Leu Thr Phe Pro Asn
145                 150                 155                 160

Tyr Gly Met Ser Trp Phe Arg Gln Ala Pro Gly Lys Gly Leu Glu Phe
                165                 170                 175

Val Cys Ala Ile Tyr Trp Ser Gly Gly Thr Val Tyr Tyr Ala Glu Ser
                180                 185                 190

Val Lys Gly Arg Phe Thr Cys Ser Arg Asp Asn Ala Lys Asn Thr Leu
            195                 200                 205

Tyr Leu Gln Met Ser Ser Leu Arg Ala Glu Asp Thr Ala Val Tyr Tyr
    210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

<210> SEQ ID NO 93
<211> LENGTH: 256
<212> TYPE: PRT
<213> ORGANISM: Artificial Sequence
<220> FEATURE:
<223> OTHER INFORMATION: chemically synthesized

<400> SEQUENCE: 93

Glu Val Gln Leu Leu Glu Ser Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
        35                  40                  45

Ser Ala Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
                100                 105                 110

Trp Gly Gln Gly Thr Leu Val Thr Val Lys Pro Gly Gly Ser Gly Gly
            115                 120                 125

Ser Glu Val Gln Leu Leu Glu Ser Gly Gly Glu Val Gln Pro Gly
    130                 135                 140

Gly Ser Leu Arg Leu Ser Cys Ala Ala Ser Gly Leu Thr Phe Pro Asn
145                 150                 155                 160

Tyr Gly Met Ser Trp Phe Arg Gln Ala Pro Gly Lys Gly Leu Glu Phe
                165                 170                 175

Val Ser Ala Ile Tyr Trp Ser Gly Gly Thr Val Tyr Tyr Ala Glu Ser
```

```
                180                 185                 190
Val Lys Gly Arg Phe Thr Ile Ser Arg Asp Asn Ala Lys Asn Thr Leu
            195                 200                 205

Tyr Leu Gln Met Ser Ser Leu Arg Ala Glu Asp Thr Ala Val Tyr Tyr
        210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

<210> SEQ ID NO 94
<211> LENGTH: 267
<212> TYPE: PRT
<213> ORGANISM: Artificial Sequence
<220> FEATURE:
<223> OTHER INFORMATION: chemically synthesized

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Asp Ser Gln Pro Thr Tyr Ser Gly Val Tyr Tyr Pro Arg
            100                 105                 110

Tyr Gly Met Asp Val Trp Gly Gln Gly Thr Leu Val Thr Val Ser Gly
        115                 120                 125

Ser Gly Gly Gly Gly Ser Glu Val Gln Leu Leu Glu Ser Gly Gly Gly
    130                 135                 140

Leu Val Gln Pro Gly Gly Ser Leu Arg Leu Ser Cys Ala Ala Ser Gly
145                 150                 155                 160

Ser Thr Phe Ser Ser Leu Asp Met Gly Trp Phe Arg Gln Ala Pro Gly
                165                 170                 175

Lys Gly Arg Glu Phe Val Ser Ala Ile Ser Arg Ser Gly Asp Asn Ile
            180                 185                 190

Tyr Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Ala Val Asp Ser Gln Pro Thr Tyr Ser Gly
225                 230                 235                 240

Gly Val Tyr Tyr Pro Arg Tyr Gly Met Asp Val Trp Gly Gln Gly Thr
                245                 250                 255

Leu Val Thr Val Ser Ser Ala Gly Gly Gly
            260                 265

<210> SEQ ID NO 95
<211> LENGTH: 263
<212> TYPE: PRT
```

```
<213> ORGANISM: Artificial Sequence
<220> FEATURE:
<223> OTHER INFORMATION: chemically synthesized

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
        35                  40                  45

Ser Ala Ile Tyr Trp Ser Gly Gly Thr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Ser Ser Gly Gly Gly Ser Gly
        115                 120                 125

Gly Ser Gly Gly Gly Gly Ser Glu Val Gln Leu Leu Glu Ser Gly Gly
    130                 135                 140

Gly Leu Val Gln Pro Gly Gly Ser Leu Arg Leu Ser Cys Ala Ala Ser
145                 150                 155                 160

Gly Leu Thr Phe Pro Asn Tyr Gly Met Ser Trp Phe Arg Gln Ala Pro
                165                 170                 175

Gly Lys Gly Leu Glu Phe Val Ser Ala Ile Tyr Trp Ser Gly Gly Thr
            180                 185                 190

Val Tyr Tyr Ala Asp Ser Val Lys Gly Arg Phe Thr Ile Ser Arg Asp
        195                 200                 205

Asn Ser Lys Asn Thr Leu Tyr Leu Gln Met Asn Ser Leu Arg Ala Glu
    210                 215                 220

Asp Thr Ala Val Tyr Tyr Cys Ala Val Thr Ile Arg Gly Ala Ala Thr
225                 230                 235                 240

Gln Thr Trp Lys Tyr Asp Tyr Trp Gly Gln Gly Thr Leu Val Thr Val
                245                 250                 255

Ser Ser Ala Gly Gly Gly Gly
            260

<210> SEQ ID NO 96
<211> LENGTH: 266
<212> TYPE: PRT
<213> ORGANISM: Artificial Sequence
<220> FEATURE:
<223> OTHER INFORMATION: chemically synthesized

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Ser Trp Phe Arg Gln Ala Pro Gly Lys Gly Leu Glu Phe Val
        35                  40                  45

Ser Ala Ile Tyr Trp Ser Gly Gly Thr Val Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Val Gln Leu Leu Glu
        130                 135                 140

Ser Gly Gly Gly Leu Val Gln Pro Gly Gly Ser Leu Arg Leu Ser Cys
145                 150                 155                 160

Ala Ala Ser Gly Leu Thr Phe Pro Asn Tyr Gly Met Ser Trp Phe Arg
            165                 170                 175

Gln Ala Pro Gly Lys Gly Leu Glu Phe Val Ser Ala Ile Tyr Trp Ser
            180                 185                 190

Gly Gly Thr Val Tyr Tyr Ala Asp Ser Val Lys Gly Arg Phe Thr Ile
            195                 200                 205

Ser Arg Asp Asn Ser Lys Asn Thr Leu Tyr Leu Gln Met Asn Ser Leu
210                 215                 220

Arg Ala Glu Asp Thr Ala Val Tyr Tyr Cys Ala Val Thr Ile Arg Gly
225                 230                 235                 240

Ala Ala Thr Gln Thr Trp Lys Tyr Asp Tyr Trp Gly Gln Gly Thr Leu
            245                 250                 255

Val Thr Val Ser Ser Ala Gly Gly Gly
            260                 265

<210> SEQ ID NO 97
<211> LENGTH: 267
<212> TYPE: PRT
<213> ORGANISM: Artificial Sequence
<220> FEATURE:
<223> OTHER INFORMATION: chemically synthesized

<400> SEQUENCE: 97

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Ser Thr Phe Ser Ser Leu
             20                  25                  30

Asp Met Gly Trp Phe Arg Gln Ala Pro Gly Lys Gly Arg Glu Phe Val
             35                  40                  45

Ser Ala Ile Ser Arg Ser Gly Asp Asn Ile Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Asp Ser Gln Pro Thr Tyr Ser Gly Val Tyr Tyr Pro Arg
            100                 105                 110

Tyr Gly Met Asp Val Trp Gly Gln Gly Thr Leu Val Thr Val Ser Gly
            115                 120                 125

Ser Gly Gly Gly Gly Ser Glu Val Gln Leu Leu Glu Ser Gly Gly Gly
        130                 135                 140

Leu Val Gln Pro Gly Gly Ser Leu Arg Leu Ser Cys Ala Ala Ser Gly
145                 150                 155                 160
```

Ser Thr Phe Ser Ser Leu Asp Met Gly Trp Phe Arg Gln Ala Pro Gly
            165                 170                 175

Lys Gly Arg Glu Phe Val Ser Ala Ile Ser Arg Ser Gly Asp Asn Ile
        180                 185                 190

Tyr Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Ala Val Asp Ser Gln Pro Thr Tyr Ser Gly
225                 230                 235                 240

Gly Val Tyr Tyr Pro Arg Tyr Gly Met Asp Val Trp Gly Gln Gly Thr
                245                 250                 255

Leu Val Thr Val Ser Ser Ala Gly Gly Gly
            260                 265

<210> SEQ ID NO 98
<211> LENGTH: 270
<212> TYPE: PRT
<213> ORGANISM: Artificial Sequence
<220> FEATURE:
<223> OTHER INFORMATION: chemically synthesized

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Asp Ser Gln Pro Thr Tyr Ser Gly Gly Val Tyr Tyr Pro Arg
            100                 105                 110

Tyr Gly Met Asp Val Trp Gly Gln Gly Thr Leu Val Thr Val Ser Ser
        115                 120                 125

Gly Gly Gly Ser Gly Gly Gly Ser Glu Val Gln Leu Leu Glu Ser
    130                 135                 140

Gly Gly Gly Leu Val Gln Pro Gly Gly Ser Leu Arg Leu Ser Cys Ala
145                 150                 155                 160

Ala Ser Gly Ser Thr Phe Ser Ser Leu Asp Met Gly Trp Phe Arg Gln
                165                 170                 175

Ala Pro Gly Lys Gly Arg Glu Phe Val Ser Ala Ile Ser Arg Ser Gly
            180                 185                 190

Asp Asn Ile Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr Tyr Cys Ala Val Asp Ser Gln Pro Thr
225                 230                 235                 240

Tyr Ser Gly Gly Val Tyr Tyr Pro Arg Tyr Gly Met Asp Val Trp Gly
                245                 250                 255

```
Gln Gly Thr Leu Val Thr Val Ser Ser Ala Gly Gly Gly
            260                 265                 270
```

<210> SEQ ID NO 99
<211> LENGTH: 273
<212> TYPE: PRT
<213> ORGANISM: Artificial Sequence
<220> FEATURE:
<223> OTHER INFORMATION: chemically synthesized

<400> SEQUENCE: 99

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Leu
            20                  25                  30

Asp Met Gly Trp Phe Arg Gln Ala Pro Gly Lys Gly Arg Glu Phe Val
        35                  40                  45

Ser Ala Ile Ser Arg Ser Gly Asp Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Asp Ser Gln Pro Thr Tyr Ser Gly Val Tyr Tyr Pro Arg
            100                 105                 110

Tyr Gly Met Asp Val Trp Gly Gln Gly Thr Leu Val Thr Val Ser Ser
        115                 120                 125

Gly Gly Gly Ser Gly Gly Ser Gly Gly Gly Ser Glu Val Gln Leu
    130                 135                 140

Leu Glu Ser Gly Gly Gly Leu Val Gln Pro Gly Gly Ser Leu Arg Leu
145                 150                 155                 160

Ser Cys Ala Ala Ser Gly Ser Thr Phe Ser Ser Leu Asp Met Gly Trp
                165                 170                 175

Phe Arg Gln Ala Pro Gly Lys Gly Arg Glu Phe Val Ser Ala Ile Ser
            180                 185                 190

Arg Ser Gly Asp Asn Ile Tyr Tyr Ala Asp Ser Val Lys Gly Arg Phe
        195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Ala Val Asp Ser
225                 230                 235                 240

Gln Pro Thr Tyr Ser Gly Val Tyr Tyr Pro Arg Tyr Gly Met Asp
                245                 250                 255

Val Trp Gly Gln Gly Thr Leu Val Thr Val Ser Ser Ala Gly Gly Gly
            260                 265                 270

Gly
```

<210> SEQ ID NO 100
<211> LENGTH: 276
<212> TYPE: PRT
<213> ORGANISM: Artificial Sequence
<220> FEATURE:
<223> OTHER INFORMATION: chemically synthesized

<400> SEQUENCE: 100

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Ser Thr Phe Ser Ser Leu
            20                  25                  30

Asp Met Ser Trp Phe Arg Gln Ala Pro Gly Lys Gly Leu Glu Phe Val
        35                  40                  45

Ser Ala Ile Ser Arg Ser Gly Asp Asn Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Val Asp Ser Gln Pro Thr Tyr Ser Gly Val Tyr Tyr Pro Arg
            100                 105                 110

Tyr Gly Met Asp Val Trp Gly Gln Gly Thr Leu Val Thr Val Ser Ser
        115                 120                 125

Gly Gly Gly Gly Ser Gly Gly Gly Ser Gly Gly Gly Gly Ser Glu
            130                 135                 140

Val Gln Leu Leu Glu Ser Gly Gly Leu Val Gln Pro Gly Gly Ser
145                 150                 155                 160

Leu Arg Leu Ser Cys Ala Ala Ser Gly Ser Thr Phe Ser Ser Leu Asp
            165                 170                 175

Met Ser Trp Phe Arg Gln Ala Pro Gly Lys Gly Leu Glu Phe Val Ser
        180                 185                 190

Ala Ile Ser Arg Ser Gly Asp Asn Ile Tyr Tyr Ala Asp Ser Val Lys
            195                 200                 205

Gly Arg Phe Thr Ile Ser Arg Asp Asn Ser Lys Asn Thr Leu Tyr Leu
        210                 215                 220

Gln Met Asn Ser Leu Arg Ala Glu Asp Thr Ala Val Tyr Tyr Cys Ala
225                 230                 235                 240

Val Asp Ser Gln Pro Thr Tyr Ser Gly Val Tyr Tyr Pro Arg Tyr
            245                 250                 255

Gly Met Asp Val Trp Gly Gln Gly Thr Leu Val Thr Val Ser Ser Ala
            260                 265                 270

Gly Gly Gly Gly
        275

<210> SEQ ID NO 101
<211> LENGTH: 259
<212> TYPE: PRT
<213> ORGANISM: Artificial Sequence
<220> FEATURE:
<223> OTHER INFORMATION: chemically synthesized

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Phe Ser Asn Tyr
            20                  25                  30

Ala Met Ser Trp Phe Arg Gln Ala Pro Gly Lys Gly Leu Glu Phe Val
        35                  40                  45

Ser Ala Ile Asn Trp Asn Gly Glu Asn Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

```
Ala Ala Ala Leu Ser Phe Arg Leu Gly Gly Glu Pro Tyr Gly Asp Ala
            100                 105                 110

Tyr Trp Gly Gln Gly Thr Leu Val Thr Val Ser Gly Ser Gly Gly
        115                 120                 125

Gly Ser Glu Val Gln Leu Leu Glu Ser Gly Gly Leu Val Gln Pro
    130                 135                 140

Gly Gly Ser Leu Arg Leu Ser Cys Ala Ala Ser Gly Arg Ala Phe Ser
145                 150                 155                 160

Asn Tyr Ala Met Ser Trp Phe Arg Gln Ala Pro Gly Lys Gly Leu Glu
                165                 170                 175

Phe Val Ser Ala Ile Asn Trp Asn Gly Glu Asn Arg Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Ala Leu Ser Phe Arg Leu Gly Gly Glu Pro Tyr Gly
225                 230                 235                 240

Asp Ala Tyr Trp Gly Gln Gly Thr Leu Val Thr Val Ser Ser Ala Gly
                245                 250                 255

Gly Gly Gly

<210> SEQ ID NO 102
<211> LENGTH: 265
<212> TYPE: PRT
<213> ORGANISM: Artificial Sequence
<220> FEATURE:
<223> OTHER INFORMATION: chemically synthesized

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Phe Ser Asn Tyr
            20                  25                  30

Ala Met Ser Trp Phe Arg Gln Ala Pro Gly Lys Gly Leu Glu Phe Val
        35                  40                  45

Ser Ala Ile Asn Trp Asn Gly Glu Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Leu Ser Phe Arg Leu Gly Gly Glu Pro Tyr Gly Asp Ala
            100                 105                 110

Tyr Trp Gly Gln Gly Thr Leu Val Thr Val Ser Ser Gly Gly Gly Ser
        115                 120                 125

Gly Gly Ser Gly Gly Gly Ser Glu Val Gln Leu Leu Glu Ser Gly
    130                 135                 140

Gly Gly Leu Val Gln Pro Gly Gly Ser Leu Arg Leu Ser Cys Ala Ala
145                 150                 155                 160

Ser Gly Arg Ala Phe Ser Asn Tyr Ala Met Ser Trp Phe Arg Gln Ala
                165                 170                 175

Pro Gly Lys Gly Leu Glu Phe Val Ser Ala Ile Asn Trp Asn Gly Glu
            180                 185                 190

Asn Arg Tyr Tyr Ala Asp Ser Val Lys Gly Arg Phe Thr Ile Ser Arg
```

```
                195                 200                 205
Asp Asn Ser Lys Asn Thr Leu Tyr Leu Gln Met Asn Ser Leu Arg Ala
        210                 215                 220

Glu Asp Thr Ala Val Tyr Tyr Cys Ala Ala Ala Leu Ser Phe Arg Leu
225                 230                 235                 240

Gly Gly Glu Pro Tyr Gly Asp Ala Tyr Trp Gly Gln Gly Thr Leu Val
                245                 250                 255

Thr Val Ser Ser Ala Gly Gly Gly Gly
        260                 265

<210> SEQ ID NO 103
<211> LENGTH: 268
<212> TYPE: PRT
<213> ORGANISM: Artificial Sequence
<220> FEATURE:
<223> OTHER INFORMATION: chemically synthesized

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Phe Ser Asn Tyr
            20                  25                  30

Ala Met Ser Trp Phe Arg Gln Ala Pro Gly Lys Gly Leu Glu Phe Val
        35                  40                  45

Ser Ala Ile Asn Trp Asn Gly Glu Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Leu Ser Phe Arg Leu Gly Gly Glu Pro Tyr Gly Asp Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Glu Val Gln Leu Leu
130                 135                 140

Glu Ser Gly Gly Gly Leu Val Gln Pro Gly Gly Ser Leu Arg Leu Ser
145                 150                 155                 160

Cys Ala Ala Ser Gly Arg Ala Phe Ser Asn Tyr Ala Met Ser Trp Phe
                165                 170                 175

Arg Gln Ala Pro Gly Lys Gly Leu Glu Phe Val Ser Ala Ile Asn Trp
            180                 185                 190

Asn Gly Glu Asn Arg Tyr Tyr Ala Asp Ser Val Lys Gly Arg Phe Thr
        195                 200                 205

Ile Ser Arg Asp Asn Ser Lys Asn Thr Leu Tyr Leu Gln Met Asn Ser
    210                 215                 220

Leu Arg Ala Glu Asp Thr Ala Val Tyr Tyr Cys Ala Ala Ala Leu Ser
225                 230                 235                 240

Phe Arg Leu Gly Gly Glu Pro Tyr Gly Asp Ala Tyr Trp Gly Gln Gly
                245                 250                 255

Thr Leu Val Thr Val Ser Ser Ala Gly Gly Gly Gly
            260                 265

<210> SEQ ID NO 104
<211> LENGTH: 261
<212> TYPE: PRT
```

<213> ORGANISM: Artificial Sequence
<220> FEATURE:
<223> OTHER INFORMATION: chemically synthesized

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Gly Trp Phe Arg Gln Ala Pro Gly Lys Glu Arg Glu Phe Val
        35                  40                  45

Ser Ala Ser Val Trp Asn Asn Gly Gly Asn Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Ser Gly Ser Gly Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Arg Ser Ile
145                 150                 155                 160

Ser Asn Tyr Ala Met Gly Trp Phe Arg Gln Ala Pro Gly Lys Glu Arg
                165                 170                 175

Glu Phe Val Ser Ala Ser Val Trp Asn Asn Gly Gly Asn Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Val Val Ala Arg Thr Pro Glu Thr Pro Ile Thr Ser Ala
225                 230                 235                 240

Arg Gly Ala Asn Tyr Trp Gly Gln Gly Thr Leu Val Thr Val Ser Ser
                245                 250                 255

Ala Gly Gly Gly Gly
            260

<210> SEQ ID NO 105
<211> LENGTH: 261
<212> TYPE: PRT
<213> ORGANISM: Artificial Sequence
<220> FEATURE:
<223> OTHER INFORMATION: chemically synthesized

<400> SEQUENCE: 105

Glu Val Gln Leu Leu Glu Ser Gly Gly Gly Lys Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Ser Trp Phe Arg Gln Ala Pro Gly Lys Gly Leu Glu Phe Val
        35                  40                  45

Ser Ala Ser Val Trp Asn Asn Gly Gly Asn Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Ser Ser Gly Gly Gly
            115                 120                 125

Gly Gly Ser Glu Val Gln Leu Leu Glu Ser Gly Gly Gly Leu Val Gln
        130                 135                 140

Pro Gly Gly Ser Leu Arg Leu Ser Cys Ala Ala Ser Gly Arg Ser Ile
145                 150                 155                 160

Ser Asn Tyr Ala Met Ser Trp Phe Arg Gln Ala Pro Gly Lys Gly Leu
                165                 170                 175

Glu Phe Val Ser Ala Ser Val Trp Asn Asn Gly Gly Asn Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
210                 215                 220

Tyr Tyr Cys Val Val Ala Arg Thr Pro Glu Thr Pro Ile Thr Ser Ala
225                 230                 235                 240

Arg Gly Ala Asn Tyr Trp Gly Gln Gly Thr Leu Val Thr Val Ser Ser
                245                 250                 255

Ala Gly Gly Gly Gly
            260

<210> SEQ ID NO 106
<211> LENGTH: 264
<212> TYPE: PRT
<213> ORGANISM: Artificial Sequence
<220> FEATURE:
<223> OTHER INFORMATION: chemically synthesized

<400> SEQUENCE: 106

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Arg Ser Ile Ser Asn Tyr
             20                  25                  30

Ala Met Ser Trp Phe Arg Gln Ala Pro Gly Lys Gly Leu Glu Phe Val
         35                  40                  45

Ser Ala Ser Val Trp Asn Asn Gly Gly Asn Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Ser Ser Gly Gly Gly
            115                 120                 125

Ser Gly Gly Gly Gly Ser Glu Val Gln Leu Leu Glu Ser Gly Gly Gly
        130                 135                 140

Leu Val Gln Pro Gly Gly Ser Leu Arg Leu Ser Cys Ala Ala Ser Gly
145                 150                 155                 160
```

Arg Ser Ile Ser Asn Tyr Ala Met Ser Trp Phe Arg Gln Ala Pro Gly
            165                 170                 175

Lys Gly Leu Glu Phe Val Ser Ala Ser Val Trp Asn Asn Gly Gly Asn
        180                 185                 190

Tyr Tyr Ala Asp Ser Val Lys Gly Arg Phe Thr Ile Ser Arg Asp Asn
            195                 200                 205

Ser Lys Asn Thr Leu Tyr Leu Gln Met Asn Ser Leu Arg Ala Glu Asp
    210                 215                 220

Thr Ala Val Tyr Tyr Cys Val Val Ala Arg Thr Pro Glu Thr Pro Ile
225                 230                 235                 240

Thr Ser Ala Arg Gly Ala Asn Tyr Trp Gly Gln Gly Thr Leu Val Thr
            245                 250                 255

Val Ser Ser Ala Gly Gly Gly Gly
            260

<210> SEQ ID NO 107
<211> LENGTH: 267
<212> TYPE: PRT
<213> ORGANISM: Artificial Sequence
<220> FEATURE:
<223> OTHER INFORMATION: chemically synthesized

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Ser Trp Phe Arg Gln Ala Pro Gly Lys Gly Leu Glu Phe Val
            35                  40                  45

Ser Ala Ser Val Trp Asn Asn Gly Gly Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Ser Ser Gly Gly Gly
        115                 120                 125

Ser Gly Gly Ser Gly Gly Gly Ser Glu Val Gln Leu Leu Glu Ser
    130                 135                 140

Gly Gly Gly Leu Val Gln Pro Gly Gly Ser Leu Arg Leu Ser Cys Ala
145                 150                 155                 160

Ala Ser Gly Arg Ser Ile Ser Asn Tyr Ala Met Ser Trp Phe Arg Gln
            165                 170                 175

Ala Pro Gly Lys Gly Leu Glu Phe Val Ser Ala Ser Val Trp Asn Asn
            180                 185                 190

Gly Gly Asn Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr Tyr Cys Val Val Ala Arg Thr Pro Glu
225                 230                 235                 240

Thr Pro Ile Thr Ser Ala Arg Gly Ala Asn Tyr Trp Gly Gln Gly Thr
            245                 250                 255

```
Leu Val Thr Val Ser Ser Ala Gly Gly Gly
        260             265
```

<210> SEQ ID NO 108
<211> LENGTH: 261
<212> TYPE: PRT
<213> ORGANISM: Artificial Sequence
<220> FEATURE:
<223> OTHER INFORMATION: chemically synthesized

<400> SEQUENCE: 108

```
Glu Val Gln Leu Leu Glu Ser Gly Gly Gly Lys Val Gln Pro Gly Gly
1               5                   10                  15

Ser Leu Arg Leu Ser Cys Ala Ala Ser Gly Arg Ser Ile Ser Asn Tyr
            20                  25                  30

Ala Met Ser Trp Phe Arg Gln Ala Pro Gly Lys Gly Leu Glu Phe Val
        35                  40                  45

Ser Ala Ser Val Trp Asn Asn Gly Gly Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Val Ala Arg Thr Pro Glu Thr Pro Ile Thr Ser Ala Arg Gly Ala
            100                 105                 110

Asn Tyr Trp Gly Gln Gly Thr Leu Val Thr Val Ser Gly Ser Gly Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Arg Ser Ile
145                 150                 155                 160

Ser Asn Tyr Ala Met Ser Trp Phe Arg Gln Ala Pro Gly Lys Gly Leu
                165                 170                 175

Glu Phe Val Ser Ala Ser Val Trp Asn Asn Gly Gly Asn Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Val Val Ala Arg Thr Pro Glu Thr Pro Ile Thr Ser Ala
225                 230                 235                 240

Arg Gly Ala Asn Tyr Trp Gly Gln Gly Thr Leu Val Thr Val Ser Ser
                245                 250                 255

Ala Gly Gly Gly Gly
            260
```

<210> SEQ ID NO 109
<211> LENGTH: 263
<212> TYPE: PRT
<213> ORGANISM: Artificial Sequence
<220> FEATURE:
<223> OTHER INFORMATION: chemically synthesized

<400> SEQUENCE: 109

```
Glu Val Gln Leu Leu Glu Ser Gly Gly Gly Leu Val Gln Pro Gly Gly
1               5                   10                  15

Ser Leu Arg Leu Ser Cys Ala Ala Ser Val Ser Thr Phe Gly Thr Ser
            20                  25                  30
```

```
Pro Val Gly Trp Phe Arg Gln Ala Pro Gly Lys Glu Arg Glu Phe Val
         35                  40                  45

Ser Ala Ile Arg Trp Asp Gly Val Gly Ala Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Pro Arg Arg Gly Asp Ser Glu Leu Pro Ser Thr Val Lys Glu
                100                 105                 110

Tyr Gly Tyr Trp Gly Gln Gly Thr Leu Val Thr Val Ser Gly Ser Gly
             115                 120                 125

Gly Gly Gly Ser Glu Val Gln Leu Leu Glu Ser Gly Gly Gly Leu Val
         130                 135                 140

Gln Pro Gly Gly Ser Leu Arg Leu Ser Cys Ala Ala Ser Val Ser Thr
145                 150                 155                 160

Phe Gly Thr Ser Pro Val Gly Trp Phe Arg Gln Ala Pro Gly Lys Glu
                165                 170                 175

Arg Glu Phe Val Ser Ala Ile Arg Trp Asp Gly Val Gly Ala Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
        210                 215                 220

Val Tyr Tyr Cys Ala Leu Pro Arg Arg Gly Asp Ser Glu Leu Pro Ser
225                 230                 235                 240

Thr Val Lys Glu Tyr Gly Tyr Trp Gly Gln Gly Thr Leu Val Thr Val
                245                 250                 255

Ser Ser Ala Gly Gly Gly Gly
                260

<210> SEQ ID NO 110
<211> LENGTH: 272
<212> TYPE: PRT
<213> ORGANISM: Artificial Sequence
<220> FEATURE:
<223> OTHER INFORMATION: chemically synthesized

<400> SEQUENCE: 110

Glu Val Gln Leu Leu Glu Ser Gly Gly Gly Leu Val Gln Pro Gly Gly
 1               5                  10                  15

Ser Leu Arg Leu Ser Cys Ala Ala Ser Val Ser Thr Phe Gly Thr Ser
             20                  25                  30

Pro Val Gly Trp Phe Arg Gln Ala Pro Gly Lys Glu Arg Glu Phe Val
         35                  40                  45

Ser Ala Ile Arg Trp Asp Gly Val Gly Ala Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Pro Arg Arg Gly Asp Ser Glu Leu Pro Ser Thr Val Lys Glu
                100                 105                 110

Tyr Gly Tyr Trp Gly Gln Gly Thr Leu Val Thr Val Ser Ser Gly Gly
             115                 120                 125
```

```
Gly Gly Ser Gly Gly Gly Ser Gly Gly Gly Ser Glu Val Gln
    130             135             140
Leu Leu Glu Ser Gly Gly Gly Leu Val Gln Pro Gly Gly Ser Leu Arg
145             150             155             160
Leu Ser Cys Ala Ala Ser Val Ser Thr Phe Gly Thr Ser Pro Val Gly
                165             170             175
Trp Phe Arg Gln Ala Pro Gly Lys Glu Arg Glu Phe Val Ser Ala Ile
            180             185             190
Arg Trp Asp Gly Val Gly Ala Tyr Tyr Ala Asp Ser Val Lys Gly Arg
        195             200             205
Phe Thr Ile Ser Arg Asp Asn Ser Lys Asn Thr Leu Tyr Leu Gln Met
    210             215             220
Asn Ser Leu Arg Ala Glu Asp Thr Ala Val Tyr Tyr Cys Ala Leu Pro
225             230             235             240
Arg Arg Gly Asp Ser Glu Leu Pro Ser Thr Val Lys Glu Tyr Gly Tyr
                245             250             255
Trp Gly Gln Gly Thr Leu Val Thr Val Ser Ser Ala Gly Gly Gly Gly
            260             265             270

<210> SEQ ID NO 111
<211> LENGTH: 265
<212> TYPE: PRT
<213> ORGANISM: Artificial Sequence
<220> FEATURE:
<223> OTHER INFORMATION: chemically synthesized

<400> SEQUENCE: 111

Glu Val Gln Leu Leu Glu Ser Gly Gly Gly Glu Val Gln Pro Gly Gly
1               5                   10                  15
Ser Leu Arg Leu Ser Cys Ala Ala Ser Gly Leu Thr Phe Pro Asn Tyr
            20                  25                  30
Gly Met Gly Trp Phe Arg Gln Ala Pro Gly Lys Glu Arg Glu Phe Val
        35                  40                  45
Ser Ala Ile Tyr Trp Ser Gly Thr Val Phe Tyr Ala Glu Ser Val
    50                  55                  60
Lys Gly Arg Phe Thr Ile Ser Arg Asp Asn Ala Lys Asn Thr Val Tyr
65                  70                  75                  80
Leu Gln Met Ser Ser Leu Arg Ala Glu Asp Thr Ala Val Tyr Tyr Cys
                85                  90                  95
Ala Val Thr Ile Arg Gly Ala Ala Thr Gln Thr Trp Lys Tyr Asp Tyr
            100                 105                 110
Trp Gly Gln Gly Thr Leu Val Thr Val Lys Pro Gly Gly Ser Gly Gly
        115                 120                 125
Ser Glu Val Gln Leu Leu Glu Ser Gly Gly Gly Val Gln Pro Gly
    130                 135                 140
Gly Ser Leu Arg Leu Ser Cys Ala Ala Ser Gly Leu Thr Phe Pro Asn
145                 150                 155                 160
Tyr Gly Met Gly Trp Phe Arg Gln Ala Pro Gly Lys Glu Arg Glu Phe
                165                 170                 175
Val Ser Ala Ile Tyr Trp Ser Gly Thr Val Phe Tyr Ala Glu Ser
            180                 185                 190
Val Lys Gly Arg Phe Thr Ile Ser Arg Asp Asn Ala Lys Asn Thr Val
        195                 200                 205
Tyr Leu Gln Met Ser Ser Leu Arg Ala Glu Asp Thr Ala Val Tyr Tyr
    210                 215                 220
```

```
Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
                260                 265

<210> SEQ ID NO 112
<211> LENGTH: 265
<212> TYPE: PRT
<213> ORGANISM: Artificial Sequence
<220> FEATURE:
<223> OTHER INFORMATION: chemically synthesized

<400> SEQUENCE: 112

Glu Val Gln Leu Leu Glu Ser Gly Gly Glu Val Gln Pro Gly Gly
1               5                   10                  15

Ser Leu Arg Leu Ser Cys Ala Ala Ser Gly Leu Thr Phe Pro Asn Tyr
                20                  25                  30

Gly Met Gly Trp Phe Arg Gln Ala Pro Gly Lys Glu Arg Glu Phe Leu
            35                  40                  45

Ala Val Ile Tyr Trp Ser Gly Gly Thr Val Phe Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro Gly Ser Gly Gly
        115                 120                 125

Ser Glu Val Gln Leu Leu Glu Ser Gly Gly Glu Val Gln Pro Gly
    130                 135                 140

Gly Ser Leu Arg Leu Ser Cys Ala Ala Ser Gly Leu Thr Phe Pro Asn
145                 150                 155                 160

Tyr Gly Met Gly Trp Phe Arg Gln Ala Pro Gly Lys Glu Arg Glu Phe
                165                 170                 175

Leu Ala Val Ile Tyr Trp Ser Gly Gly Thr Val Phe Tyr Ala Glu Ser
            180                 185                 190

Val Lys Gly Arg Phe Thr Ile Ser Arg Asp Asn Ala Lys Asn Thr Val
        195                 200                 205

Tyr Leu Gln Met Ser Ser Leu Arg Ala Glu Asp Thr Ala Val Tyr Tyr
    210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
                260                 265

<210> SEQ ID NO 113
<211> LENGTH: 265
<212> TYPE: PRT
<213> ORGANISM: Artificial Sequence
<220> FEATURE:
<223> OTHER INFORMATION: chemically synthesized
```

<400> SEQUENCE: 113

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Val
        35                  40                  45

Ser Ala Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
            85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro Gly Gly Ser Gly Gly
            115                 120                 125

Ser Glu Val Gln Leu Leu Glu Ser Gly Gly Gly Glu Val Gln Pro Gly
    130                 135                 140

Gly Ser Leu Arg Leu Ser Cys Ala Ala Ser Gly Leu Thr Phe Pro Asn
145                 150                 155                 160

Tyr Gly Met Gly Trp Phe Arg Gln Ala Pro Gly Lys Glu Arg Glu Phe
                165                 170                 175

Val Ser Ala Ile Tyr Trp Ser Gly Gly Thr Val Tyr Tyr Ala Glu Ser
            180                 185                 190

Val Lys Gly Arg Phe Thr Ile Ser Arg Asp Asn Ala Lys Asn Thr Leu
        195                 200                 205

Tyr Leu Gln Met Ser Ser Leu Arg Ala Glu Asp Thr Ala Val Tyr Tyr
    210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
            260                 265

<210> SEQ ID NO 114
<211> LENGTH: 265
<212> TYPE: PRT
<213> ORGANISM: Artificial Sequence
<220> FEATURE:
<223> OTHER INFORMATION: chemically synthesized

<400> SEQUENCE: 114

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Leu
        35                  40                  45

Ala Val Ile Tyr Trp Ser Gly Gly Thr Val Tyr Tyr Ala Glu Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys

```
                    85                  90                  95
Ala Val Thr Ile Arg Gly Ala Ala Thr Gln Thr Trp Lys Tyr Asp Tyr
                100                 105                 110

Trp Gly Gln Gly Thr Leu Val Thr Val Lys Pro Gly Gly Ser Gly Gly
                115                 120                 125

Ser Glu Val Gln Leu Leu Glu Ser Gly Gly Gly Val Gln Pro Gly
        130                 135                 140

Gly Ser Leu Arg Leu Ser Cys Ala Ala Ser Gly Leu Thr Phe Pro Asn
145                 150                 155                 160

Tyr Gly Met Gly Trp Phe Arg Gln Ala Pro Gly Lys Glu Arg Glu Phe
                165                 170                 175

Leu Ala Val Ile Tyr Trp Ser Gly Gly Thr Val Tyr Tyr Ala Glu Ser
                180                 185                 190

Val Lys Gly Arg Phe Thr Ile Ser Arg Asp Asn Ala Lys Asn Thr Leu
                195                 200                 205

Tyr Leu Gln Met Ser Ser Leu Arg Ala Glu Asp Thr Ala Val Tyr Tyr
        210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
                260                 265

<210> SEQ ID NO 115
<211> LENGTH: 265
<212> TYPE: PRT
<213> ORGANISM: Artificial Sequence
<220> FEATURE:
<223> OTHER INFORMATION: chemically synthesized

<400> SEQUENCE: 115

Glu Val Gln Leu Leu Glu Ser Gly Gly Gly Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Val
        35                  40                  45

Ser Ala Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
                100                 105                 110

Trp Gly Gln Gly Thr Leu Val Thr Val Lys Pro Gly Gly Ser Gly Gly
                115                 120                 125

Ser Glu Val Gln Leu Leu Glu Ser Gly Gly Gly Glu Val Gln Pro Gly
        130                 135                 140

Gly Ser Leu Arg Leu Ser Cys Ala Ala Ser Gly Leu Thr Phe Pro Asn
145                 150                 155                 160

Tyr Gly Met Gly Trp Phe Arg Gln Ala Pro Gly Lys Glu Arg Glu Phe
                165                 170                 175

Val Ser Ala Ile Tyr Trp Ser Gly Gly Thr Val Tyr Tyr Ala Glu Ser
```

```
            180                 185                 190
Val Lys Gly Arg Phe Thr Ile Ser Arg Asp Asn Ala Lys Asn Thr Val
            195                 200                 205

Tyr Leu Gln Met Ser Ser Leu Arg Ala Glu Asp Thr Ala Val Tyr Tyr
            210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
            260                 265

<210> SEQ ID NO 116
<211> LENGTH: 265
<212> TYPE: PRT
<213> ORGANISM: Artificial Sequence
<220> FEATURE:
<223> OTHER INFORMATION: chemically synthesized

<400> SEQUENCE: 116

Glu Val Gln Leu Leu Glu Ser Gly Gly Gly Glu Val Gln Pro Gly Gly
1               5                   10                  15

Ser Leu Arg Leu Ser Cys Ala Ala Ser Gly Leu Thr Phe Pro Asn Tyr
            20                  25                  30

Gly Met Gly Trp Phe Arg Gln Ala Pro Gly Lys Glu Arg Glu Phe Leu
        35                  40                  45

Ala Val Ile Tyr Trp Ser Gly Gly Thr Val Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Val Thr Ile Arg Gly Ala Ala Thr Gln Thr Trp Lys Tyr Asp Tyr
            100                 105                 110

Trp Gly Gln Gly Thr Leu Val Thr Val Lys Pro Gly Gly Ser Gly Gly
        115                 120                 125

Ser Glu Val Gln Leu Leu Glu Ser Gly Gly Gly Glu Val Gln Pro Gly
    130                 135                 140

Gly Ser Leu Arg Leu Ser Cys Ala Ala Ser Gly Leu Thr Phe Pro Asn
145                 150                 155                 160

Tyr Gly Met Gly Trp Phe Arg Gln Ala Pro Gly Lys Glu Arg Glu Phe
                165                 170                 175

Leu Ala Val Ile Tyr Trp Ser Gly Gly Thr Val Tyr Tyr Ala Glu Ser
            180                 185                 190

Val Lys Gly Arg Phe Thr Ile Ser Arg Asp Asn Ala Lys Asn Thr Val
            195                 200                 205

Tyr Leu Gln Met Ser Ser Leu Arg Ala Glu Asp Thr Ala Val Tyr Tyr
            210                 215                 220

Cys Ala Val Thr Ile Arg Gly Ala Ala Thr Gln Thr Trp Lys Tyr Asp
225                 230                 235                 240

Tyr Trp Gly Gln Gly Thr Leu Val Thr Val Lys Pro Gly Gly Gly Gly
                245                 250                 255

Asp Lys Thr His Thr Cys Pro Pro Cys
            260                 265
```

```
<210> SEQ ID NO 117
<211> LENGTH: 267
<212> TYPE: PRT
<213> ORGANISM: Artificial Sequence
<220> FEATURE:
<223> OTHER INFORMATION: chemically synthesized

<400> SEQUENCE: 117
```

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Thr Val Ser Asn Tyr
            20                  25                  30

Ala Met Gly Trp Phe Arg Gln Ala Pro Gly Lys Asp Arg Glu Phe Val
        35                  40                  45

Ser Ala Leu Asn Trp Gly Gly Asp Thr Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Ala Gln Ser Phe Arg Arg Gly Gly Ala Pro Tyr Gly Asp Asn
            100                 105                 110

Tyr Trp Gly Gln Gly Thr Leu Val Thr Val Lys Pro Gly Gly Ser Gly
        115                 120                 125

Gly Ser Glu Val Gln Leu Leu Glu Ser Gly Gly Glu Val Gln Pro
130                 135                 140

Gly Gly Ser Leu Arg Leu Ser Cys Ala Ala Ser Gly Arg Thr Val Ser
145                 150                 155                 160

Asn Tyr Ala Met Gly Trp Phe Arg Gln Ala Pro Gly Lys Asp Arg Glu
                165                 170                 175

Phe Val Ser Ala Leu Asn Trp Gly Gly Asp Thr Thr Tyr Tyr Ala Glu
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Arg Ala Glu Asp Thr Ala Val Tyr
    210                 215                 220

Tyr Cys Ala Ala Ala Gln Ser Phe Arg Arg Gly Gly Ala Pro Tyr Gly
225                 230                 235                 240

Asp Asn Tyr Trp Gly Gln Gly Thr Leu Val Thr Val Lys Pro Gly Gly
                245                 250                 255

Gly Gly Asp Lys Thr His Thr Cys Pro Pro Cys
            260                 265

```
<210> SEQ ID NO 118
<211> LENGTH: 270
<212> TYPE: PRT
<213> ORGANISM: Artificial Sequence
<220> FEATURE:
<223> OTHER INFORMATION: chemically synthesized

<400> SEQUENCE: 118
```

Glu Val Gln Leu Leu Glu Ser Gly Gly Gly Glu Val Gln Pro Gly Gly
1               5                   10                  15

Ser Leu Arg Leu Ser Cys Ala Ala Ser Gly Arg Thr Val Ser Asn Tyr
            20                  25                  30

Ala Met Gly Trp Phe Arg Gln Ala Pro Gly Lys Asp Arg Glu Phe Val
        35                  40                  45

-continued

```
Ser Ala Leu Asn Trp Gly Gly Asp Thr Thr Tyr Tyr Ala Glu Ser Val
 50                  55                  60
Lys Gly Arg Phe Thr Ile Ser Arg Asp Asn Ala Lys Asn Thr Leu Tyr
 65                  70                  75                  80
Leu Gln Met Ser Ser Leu Arg Ala Glu Asp Thr Ala Val Tyr Tyr Cys
                 85                  90                  95
Ala Ala Ala Gln Ser Phe Arg Arg Gly Gly Ala Pro Tyr Gly Asp Asn
                100                 105                 110
Tyr Trp Gly Gln Gly Thr Leu Val Thr Val Lys Pro Gly Gly Ser Gly
            115                 120                 125
Gly Ser Gly Gly Ser Glu Val Gln Leu Leu Glu Ser Gly Gly Gly Glu
        130                 135                 140
Val Gln Pro Gly Gly Ser Leu Arg Leu Ser Cys Ala Ala Ser Gly Arg
145                 150                 155                 160
Thr Val Ser Asn Tyr Ala Met Gly Trp Phe Arg Gln Ala Pro Gly Lys
                165                 170                 175
Asp Arg Glu Phe Val Ser Ala Leu Asn Trp Gly Gly Asp Thr Thr Tyr
            180                 185                 190
Tyr Ala Glu Ser Val Lys Gly Arg Phe Thr Ile Ser Arg Asp Asn Ala
        195                 200                 205
Lys Asn Thr Leu Tyr Leu Gln Met Ser Ser Leu Arg Ala Glu Asp Thr
210                 215                 220
Ala Val Tyr Tyr Cys Ala Ala Gln Ser Phe Arg Arg Gly Gly Ala
225                 230                 235                 240
Pro Tyr Gly Asp Asn Tyr Trp Gly Gln Gly Thr Leu Val Thr Val Lys
                245                 250                 255
Pro Gly Gly Gly Gly Asp Lys Thr His Thr Cys Pro Pro Cys
            260                 265                 270

<210> SEQ ID NO 119
<211> LENGTH: 410
<212> TYPE: PRT
<213> ORGANISM: Artificial Sequence
<220> FEATURE:
<223> OTHER INFORMATION: chemically synthesized

<400> SEQUENCE: 119

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Arg Ser Ile Ser Asn Tyr
                 20                  25                  30
Ala Met Ser Trp Phe Arg Gln Ala Pro Gly Lys Gly Leu Glu Phe Val
             35                  40                  45
Ser Ala Ser Val Trp Asn Asn Gly Gly Asn Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Val Val Ala Arg Thr Pro Glu Thr Pro Ile Thr Ser Ala Arg Gly Ala
                100                 105                 110
Asn Tyr Trp Gly Gln Gly Thr Leu Val Thr Val Ser Ser Gly Gly Gly
            115                 120                 125
Gly Ser Gly Gly Gly Gly Ser Gly Gly Gly Gly Ser Glu Val Gln Leu
        130                 135                 140
```

```
Leu Glu Ser Gly Gly Gly Leu Val Gln Pro Gly Gly Ser Leu Arg Leu
145                 150                 155                 160

Ser Cys Ala Ala Ser Gly Arg Ser Ile Ser Asn Tyr Ala Met Ser Trp
            165                 170                 175

Phe Arg Gln Ala Pro Gly Lys Gly Leu Glu Phe Val Ser Ala Ser Val
        180                 185                 190

Trp Asn Asn Gly Gly Asn Tyr Tyr Ala Asp Ser Val Lys Gly Arg Phe
            195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Val Val Ala Arg
225                 230                 235                 240

Thr Pro Glu Thr Pro Ile Thr Ser Ala Arg Gly Ala Asn Tyr Trp Gly
                245                 250                 255

Gln Gly Thr Leu Val Thr Val Ser Ser Gly Gly Gly Ser Gly Gly
                260                 265                 270

Gly Gly Ser Gly Gly Gly Ser Glu Val Gln Leu Leu Glu Ser Gly
        275                 280                 285

Gly Gly Leu Val Gln Pro Gly Gly Ser Leu Arg Leu Ser Cys Ala Ala
    290                 295                 300

Ser Gly Arg Ser Ile Ser Asn Tyr Ala Met Ser Trp Phe Arg Gln Ala
305                 310                 315                 320

Pro Gly Lys Gly Leu Glu Phe Val Ser Ala Ser Val Trp Asn Asn Gly
                325                 330                 335

Gly Asn Tyr Tyr Ala Asp Ser Val Lys Gly Arg Phe Thr Ile Ser Arg
            340                 345                 350

Asp Asn Ser Lys Asn Thr Leu Tyr Leu Gln Met Asn Ser Leu Arg Ala
        355                 360                 365

Glu Asp Thr Ala Val Tyr Tyr Cys Val Val Ala Arg Thr Pro Glu Thr
    370                 375                 380

Pro Ile Thr Ser Ala Arg Gly Ala Asn Tyr Trp Gly Gln Gly Thr Leu
385                 390                 395                 400

Val Thr Val Ser Ser Ala Gly Gly Gly Gly
                405                 410

<210> SEQ ID NO 120
<211> LENGTH: 394
<212> TYPE: PRT
<213> ORGANISM: Artificial Sequence
<220> FEATURE:
<223> OTHER INFORMATION: chemically synthesized

<400> SEQUENCE: 120

Glu Val Gln Leu Leu Glu Ser Gly Gly Gly Glu Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Cys Ala Ile Arg Trp Glu Gly Val Gly Ala Tyr Tyr Ala Glu Ser Val
    50                  55                  60

Lys Gly Arg Phe Thr Cys Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95
```

-continued

```
Ala Leu Pro Arg Arg Gly Asp Ser Glu Leu Pro Ser Thr Val Lys Glu
                100                 105                 110

Tyr Gly Tyr Trp Gly Gln Gly Thr Leu Val Thr Val Lys Pro Gly Gly
            115                 120                 125

Ser Gly Gly Ser Glu Val Gln Leu Leu Glu Ser Gly Gly Glu Val
        130                 135                 140

Gln Pro Gly Gly Ser Leu Arg Leu Ser Cys Ala Ala Ser Val Ser Thr
145                 150                 155                 160

Phe Gly Thr Ser Pro Val Gly Trp Phe Arg Gln Ala Pro Gly Lys Glu
                165                 170                 175

Arg Glu Phe Val Cys Ala Ile Arg Trp Glu Gly Val Gly Ala Tyr Tyr
            180                 185                 190

Ala Glu Ser Val Lys Gly Arg Phe Thr Cys Ser Arg Asp Asn Ala Lys
        195                 200                 205

Asn Thr Leu Tyr Leu Gln Met Ser Ser Leu Arg Ala Glu Asp Thr Ala
                210                 215                 220

Val Tyr Tyr Cys Ala Leu Pro Arg Arg Gly Asp Ser Glu Leu Pro Ser
225                 230                 235                 240

Thr Val Lys Glu Tyr Gly Tyr Trp Gly Gln Gly Thr Leu Val Thr Val
                245                 250                 255

Lys Pro Gly Gly Ser Gly Gly Ser Glu Val Gln Leu Leu Glu Ser Gly
            260                 265                 270

Gly Gly Glu Val Gln Pro Gly Gly Ser Leu Arg Leu Ser Cys Ala Ala
        275                 280                 285

Ser Val Ser Thr Phe Gly Thr Ser Pro Val Gly Trp Phe Arg Gln Ala
290                 295                 300

Pro Gly Lys Glu Arg Glu Phe Val Cys Ala Ile Arg Trp Glu Gly Val
305                 310                 315                 320

Gly Ala Tyr Tyr Ala Glu Ser Val Lys Gly Arg Phe Thr Cys Ser Arg
                325                 330                 335

Asp Asn Ala Lys Asn Thr Leu Tyr Leu Gln Met Ser Ser Leu Arg Ala
            340                 345                 350

Glu Asp Thr Ala Val Tyr Tyr Cys Ala Leu Pro Arg Arg Gly Asp Ser
        355                 360                 365

Glu Leu Pro Ser Thr Val Lys Glu Tyr Gly Tyr Trp Gly Gln Gly Thr
370                 375                 380

Leu Val Thr Val Lys Pro Gly Gly Gly Gly
385                 390
```

<210> SEQ ID NO 121
<211> LENGTH: 394
<212> TYPE: PRT
<213> ORGANISM: Artificial Sequence
<220> FEATURE:
<223> OTHER INFORMATION: chemically synthesized

<400> SEQUENCE: 121

```
Glu Val Gln Leu Leu Glu Ser Gly Gly Gly Val Gln Pro Gly Gly
1               5                   10                  15

Ser Leu Arg Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Glu Gly Val Gly Ala Tyr Tyr Ala Glu Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
             85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Leu Val Thr Val Lys Pro Gly Gly
            115                 120                 125

Ser Gly Gly Ser Glu Val Gln Leu Leu Glu Ser Gly Gly Gly Glu Val
        130                 135                 140

Gln Pro Gly Gly Ser Leu Arg Leu Ser Cys Ala Ala Ser Val Ser Thr
145                 150                 155                 160

Phe Gly Thr Ser Pro Val Gly Trp Phe Arg Gln Ala Pro Gly Lys Glu
            165                 170                 175

Arg Glu Phe Val Ser Ala Ile Arg Trp Glu Gly Val Gly Ala Tyr Tyr
            180                 185                 190

Ala Glu Ser Val Lys Gly Arg Phe Thr Ile Ser Arg Asp Asn Ala Lys
        195                 200                 205

Asn Thr Leu Tyr Leu Gln Met Ser Ser Leu Arg Ala Glu Asp Thr Ala
210                 215                 220

Val Tyr Tyr Cys Ala Leu Pro Arg Arg Gly Asp Ser Glu Leu Pro Ser
225                 230                 235                 240

Thr Val Lys Glu Tyr Gly Tyr Trp Gly Gln Gly Thr Leu Val Thr Val
            245                 250                 255

Lys Pro Gly Gly Ser Gly Gly Ser Glu Val Gln Leu Leu Glu Ser Gly
        260                 265                 270

Gly Gly Glu Val Gln Pro Gly Gly Ser Leu Arg Leu Ser Cys Ala Ala
        275                 280                 285

Ser Val Ser Thr Phe Gly Thr Ser Pro Val Gly Trp Phe Arg Gln Ala
290                 295                 300

Pro Gly Lys Glu Arg Glu Phe Val Ser Ala Ile Arg Trp Glu Gly Val
305                 310                 315                 320

Gly Ala Tyr Tyr Ala Glu Ser Val Lys Gly Arg Phe Thr Ile Ser Arg
            325                 330                 335

Asp Asn Ala Lys Asn Thr Leu Tyr Leu Gln Met Ser Ser Leu Arg Ala
            340                 345                 350

Glu Asp Thr Ala Val Tyr Tyr Cys Ala Leu Pro Arg Arg Gly Asp Ser
        355                 360                 365

Glu Leu Pro Ser Thr Val Lys Glu Tyr Gly Tyr Trp Gly Gln Gly Thr
        370                 375                 380

Leu Val Thr Val Lys Pro Gly Gly Gly
385                 390

<210> SEQ ID NO 122
<211> LENGTH: 400
<212> TYPE: PRT
<213> ORGANISM: Artificial Sequence
<220> FEATURE:
<223> OTHER INFORMATION: chemically synthesized

<400> SEQUENCE: 122

Glu Val Gln Leu Leu Glu Ser Gly Gly Gly Glu Val Gln Pro Gly Gly
  1               5                  10                  15

Ser Leu Arg Leu Ser Cys Ala Ala Ser Gly Ser Thr Phe Ser Ser Leu
             20                  25                  30
```

```
Asp Met Gly Trp Phe Arg Gln Ala Pro Gly Lys Gly Arg Glu Phe Val
        35                  40                  45

Cys Ala Ile Ser Arg Ser Gly Asp Asn Ile Tyr Tyr Ala Glu Ser Val
 50                  55                  60

Lys Gly Arg Phe Thr Cys Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Val Glu Ser Gln Pro Thr Tyr Ser Gly Val Tyr Tyr Pro Arg
                100                 105                 110

Tyr Gly Met Asp Val Trp Gly Gln Gly Thr Leu Val Thr Val Lys Pro
                115                 120                 125

Gly Gly Ser Gly Gly Ser Glu Val Gln Leu Leu Glu Ser Gly Gly Gly
    130                 135                 140

Glu Val Gln Pro Gly Gly Ser Leu Arg Leu Ser Cys Ala Ala Ser Gly
145                 150                 155                 160

Ser Thr Phe Ser Ser Leu Asp Met Gly Trp Phe Arg Gln Ala Pro Gly
                165                 170                 175

Lys Gly Arg Glu Phe Val Cys Ala Ile Ser Arg Ser Gly Asp Asn Ile
            180                 185                 190

Tyr Tyr Ala Glu Ser Val Lys Gly Arg Phe Thr Cys Ser Arg Asp Asn
            195                 200                 205

Ala Lys Asn Thr Leu Tyr Leu Gln Met Ser Ser Leu Arg Ala Glu Asp
210                 215                 220

Thr Ala Val Tyr Tyr Cys Ala Val Glu Ser Gln Pro Thr Tyr Ser Gly
225                 230                 235                 240

Gly Val Tyr Tyr Pro Arg Tyr Gly Met Asp Val Trp Gly Gln Gly Thr
                245                 250                 255

Leu Val Thr Val Lys Pro Gly Gly Ser Gly Gly Ser Glu Val Gln Leu
                260                 265                 270

Leu Glu Ser Gly Gly Gly Glu Val Gln Pro Gly Gly Ser Leu Arg Leu
            275                 280                 285

Ser Cys Ala Ala Ser Gly Ser Thr Phe Ser Ser Leu Asp Met Gly Trp
290                 295                 300

Phe Arg Gln Ala Pro Gly Lys Gly Arg Glu Phe Val Cys Ala Ile Ser
305                 310                 315                 320

Arg Ser Gly Asp Asn Ile Tyr Tyr Ala Glu Ser Val Lys Gly Arg Phe
                325                 330                 335

Thr Cys Ser Arg Asp Asn Ala Lys Asn Thr Leu Tyr Leu Gln Met Ser
                340                 345                 350

Ser Leu Arg Ala Glu Asp Thr Ala Val Tyr Tyr Cys Ala Val Glu Ser
            355                 360                 365

Gln Pro Thr Tyr Ser Gly Gly Val Tyr Tyr Pro Arg Tyr Gly Met Asp
370                 375                 380

Val Trp Gly Gln Gly Thr Leu Val Thr Val Lys Pro Gly Gly Gly Gly
385                 390                 395                 400
```

<210> SEQ ID NO 123
<211> LENGTH: 400
<212> TYPE: PRT
<213> ORGANISM: Artificial Sequence
<220> FEATURE:
<223> OTHER INFORMATION: chemically synthesized

<400> SEQUENCE: 123

```
Glu Val Gln Leu Leu Glu Ser Gly Gly Gly Val Gln Pro Gly Gly
  1               5                  10                 15

Ser Leu Arg Leu Ser Cys Ala Ala Ser Gly Thr Phe Ser Ser Leu
             20                  25                  30

Asp Met Gly Trp Phe Arg Gln Ala Pro Gly Lys Gly Arg Glu Phe Val
         35                  40                  45

Ser Ala Ile Ser Arg Ser Gly Asp Asn Ile Tyr Tyr Ala Glu Ser Val
 50                  55                  60

Lys Gly Arg Phe Thr Ile Ser Arg Asp Asn Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Val Glu Ser Gln Pro Thr Tyr Ser Gly Val Tyr Tyr Pro Arg
                100                 105                 110

Tyr Gly Met Asp Val Trp Gly Gln Gly Thr Leu Val Thr Val Lys Pro
             115                 120                 125

Gly Gly Ser Gly Gly Ser Glu Val Gln Leu Leu Glu Ser Gly Gly Gly
         130                 135                 140

Glu Val Gln Pro Gly Gly Ser Leu Arg Leu Ser Cys Ala Ala Ser Gly
145                 150                 155                 160

Ser Thr Phe Ser Ser Leu Asp Met Gly Trp Phe Arg Gln Ala Pro Gly
                 165                 170                 175

Lys Gly Arg Glu Phe Val Ser Ala Ile Ser Arg Ser Gly Asp Asn Ile
             180                 185                 190

Tyr Tyr Ala Glu Ser Val Lys Gly Arg Phe Thr Ile Ser Arg Asp Asn
             195                 200                 205

Ala Lys Asn Thr Leu Tyr Leu Gln Met Ser Ser Leu Arg Ala Glu Asp
210                 215                 220

Thr Ala Val Tyr Tyr Cys Ala Val Glu Ser Gln Pro Thr Tyr Ser Gly
225                 230                 235                 240

Gly Val Tyr Tyr Pro Arg Tyr Gly Met Asp Val Trp Gly Gln Gly Thr
                 245                 250                 255

Leu Val Thr Val Lys Pro Gly Gly Ser Gly Gly Ser Glu Val Gln Leu
             260                 265                 270

Leu Glu Ser Gly Gly Gly Glu Val Gln Pro Gly Gly Ser Leu Arg Leu
             275                 280                 285

Ser Cys Ala Ala Ser Gly Ser Thr Phe Ser Ser Leu Asp Met Gly Trp
             290                 295                 300

Phe Arg Gln Ala Pro Gly Lys Gly Arg Glu Phe Val Ser Ala Ile Ser
305                 310                 315                 320

Arg Ser Gly Asp Asn Ile Tyr Tyr Ala Glu Ser Val Lys Gly Arg Phe
                 325                 330                 335

Thr Ile Ser Arg Asp Asn Ala Lys Asn Thr Leu Tyr Leu Gln Met Ser
             340                 345                 350

Ser Leu Arg Ala Glu Asp Thr Ala Val Tyr Tyr Cys Ala Val Glu Ser
             355                 360                 365

Gln Pro Thr Tyr Ser Gly Gly Val Tyr Tyr Pro Arg Tyr Gly Met Asp
             370                 375                 380

Val Trp Gly Gln Gly Thr Leu Val Thr Val Lys Pro Gly Gly Gly
385                 390                 395                 400

<210> SEQ ID NO 124
<211> LENGTH: 413
<212> TYPE: PRT
```

<213> ORGANISM: Artificial Sequence
<220> FEATURE:
<223> OTHER INFORMATION: chemically synthesized

<400> SEQUENCE: 124

Gln Val Gln Leu Val Gln Ser Gly Gly Gly Leu Val Gln Ala Gly Gly
1               5                   10                  15

Ser Leu Thr Leu Ser Cys Ala Ala Ser Val Ser Thr Phe Gly Thr Ser
            20                  25                  30

Pro Val Gly Trp Phe Arg Gln Ala Pro Gly Lys Glu Arg Glu Phe Val
        35                  40                  45

Ser Ala Ile Arg Trp Asp Gly Val Gly Ala Tyr Tyr Ala Asp Ser Val
    50                  55                  60

Arg Gly Arg Phe Lys Asn Ser Lys Asp Asn Ala Lys Arg Thr Ala Tyr
65                  70                  75                  80

Leu Gln Met Asn Arg Leu Lys Pro Glu Asp Thr Ala Val Tyr Tyr Cys
                85                  90                  95

Ala Leu Pro Arg Arg Gly Asp Ser Glu Leu Pro Ser Thr Val Lys Glu
            100                 105                 110

Tyr Gly Tyr Trp Gly Gln Gly Thr Gln Val Thr Val Ser Ser Gly Gly
        115                 120                 125

Gly Gly Ser Gly Gly Gly Ser Gly Gly Gly Ser Gln Val Gln
            130                 135                 140

Leu Val Gln Ser Gly Gly Gly Leu Val Gln Ala Gly Gly Ser Leu Thr
145                 150                 155                 160

Leu Ser Cys Ala Ala Ser Val Ser Thr Phe Gly Thr Ser Pro Val Gly
                165                 170                 175

Trp Phe Arg Gln Ala Pro Gly Lys Glu Arg Glu Phe Val Ser Ala Ile
            180                 185                 190

Arg Trp Asp Gly Val Gly Ala Tyr Tyr Ala Asp Ser Val Arg Gly Arg
        195                 200                 205

Phe Lys Asn Ser Lys Asp Asn Ala Lys Arg Thr Ala Tyr Leu Gln Met
    210                 215                 220

Asn Arg Leu Lys Pro Glu Asp Thr Ala Val Tyr Tyr Cys Ala Leu Pro
225                 230                 235                 240

Arg Arg Gly Asp Ser Glu Leu Pro Ser Thr Val Lys Glu Tyr Gly Tyr
                245                 250                 255

Trp Gly Gln Gly Thr Gln Val Thr Val Ser Ser Gly Gly Gly Gly Ser
            260                 265                 270

Gly Gly Gly Gly Ser Gly Gly Gly Ser Gln Val Gln Leu Val Gln
        275                 280                 285

Ser Gly Gly Gly Leu Val Gln Ala Gly Gly Ser Leu Thr Leu Ser Cys
    290                 295                 300

Ala Ala Ser Val Ser Thr Phe Gly Thr Ser Pro Val Gly Trp Phe Arg
305                 310                 315                 320

Gln Ala Pro Gly Lys Glu Arg Glu Phe Val Ser Ala Ile Arg Trp Asp
                325                 330                 335

Gly Val Gly Ala Tyr Tyr Ala Asp Ser Val Arg Gly Arg Phe Lys Asn
            340                 345                 350

Ser Lys Asp Asn Ala Lys Arg Thr Ala Tyr Leu Gln Met Asn Arg Leu
        355                 360                 365

Lys Pro Glu Asp Thr Ala Val Tyr Tyr Cys Ala Leu Pro Arg Arg Gly
    370                 375                 380

Asp Ser Glu Leu Pro Ser Thr Val Lys Glu Tyr Gly Tyr Trp Gly Gln

```
                385                 390                 395                 400
Gly Thr Gln Val Thr Val Ser Ser Ala Gly Gly Gly
                    405                 410

<210> SEQ ID NO 125
<211> LENGTH: 593
<212> TYPE: PRT
<213> ORGANISM: Artificial Sequence
<220> FEATURE:
<223> OTHER INFORMATION: chemically synthesized

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Val Tyr Tyr Cys Asn
                85                  90                  95

Ala Glu Ile Leu Lys Arg Ala Tyr Ile Asp Val Tyr Val Asn Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Leu Glu Ser Gly Gly Gly Leu Val Gln Pro Gly Gly Ser Leu Arg
                165                 170                 175

Leu Ser Cys Ala Ala Ser Gly Thr Phe Asp Lys Ile Asn Asn Met Gly
            180                 185                 190

Trp Tyr Arg Gln Ala Pro Gly Lys Gln Arg Asp Leu Val Ala Gln Ile
        195                 200                 205

Thr Pro Gly Gly Ile Thr Asp Tyr Ala Asp Ser Val Lys Gly Arg Phe
    210                 215                 220

Thr Ile Ser Arg Asp Asn Ser Lys Asn Thr Leu Tyr Leu Gln Met Asn
225                 230                 235                 240

Ser Leu Arg Pro Glu Asp Thr Ala Val Tyr Tyr Cys Asn Ala Glu Ile
                245                 250                 255

Leu Lys Arg Ala Tyr Ile Asp Val Tyr Val Asn Tyr Trp Gly Gln Gly
            260                 265                 270

Thr Leu Val Thr Val Ser Ser Gly Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Gly Gly Gly Gly Ser Glu Val Gln Leu Leu Glu
305                 310                 315                 320

Ser Gly Gly Gly Leu Val Gln Pro Gly Gly Ser Leu Arg Leu Ser Cys
                325                 330                 335

Ala Ala Ser Gly Thr Phe Asp Lys Ile Asn Asn Met Gly Trp Tyr Arg
```

```
            340                 345                 350
Gln Ala Pro Gly Lys Gln Arg Asp Leu Val Ala Gln Ile Thr Pro Gly
            355                 360                 365
Gly Ile Thr Asp Tyr Ala Asp Ser Val Lys Gly Arg Phe Thr Ile Ser
            370                 375                 380
Arg Asp Asn Ser Lys Asn Thr Leu Tyr Leu Gln Met Asn Ser Leu Arg
385                 390                 395                 400
Pro Glu Asp Thr Ala Val Tyr Tyr Cys Asn Ala Glu Ile Leu Lys Arg
                405                 410                 415
Ala Tyr Ile Asp Val Tyr Val Asn Tyr Trp Gly Gln Gly Thr Leu Val
            420                 425                 430
Thr Val Ser Ser Gly Gly Gly Ser Gly Gly Gly Ser Gly Gly
            435                 440                 445
Gly Gly Ser Gly Gly Gly Ser Gly Gly Gly Ser Gly Gly Gly
            450                 455                 460
Gly Ser Gly Gly Gly Ser Glu Val Gln Leu Leu Glu Ser Gly Gly
465                 470                 475                 480
Gly Leu Val Gln Pro Gly Gly Ser Leu Arg Leu Ser Cys Ala Ala Ser
                485                 490                 495
Gly Thr Phe Asp Lys Ile Asn Asn Met Gly Trp Tyr Arg Gln Ala Pro
            500                 505                 510
Gly Lys Gln Arg Asp Leu Val Ala Gln Ile Thr Pro Gly Gly Ile Thr
            515                 520                 525
Asp Tyr Ala Asp Ser Val Lys Gly Arg Phe Thr Ile Ser Arg Asp Asn
            530                 535                 540
Ser Lys Asn Thr Leu Tyr Leu Gln Met Asn Ser Leu Arg Pro Glu Asp
545                 550                 555                 560
Thr Ala Val Tyr Tyr Cys Asn Ala Glu Ile Leu Lys Arg Ala Tyr Ile
                565                 570                 575
Asp Val Tyr Val Asn Tyr Trp Gly Gln Gly Thr Leu Val Thr Val Ser
            580                 585                 590
Ser

<210> SEQ ID NO 126
<211> LENGTH: 595
<212> TYPE: PRT
<213> ORGANISM: Artificial Sequence
<220> FEATURE:
<223> OTHER INFORMATION: chemically synthesized

<400> SEQUENCE: 126

Glu Val Gln Leu Leu Glu Ser Gly Gly Gly Val Gln Pro Gly Gly
1               5                   10                  15
Ser Leu Arg Leu Ser Cys Ala Ala Ser Gly Thr Phe Asp Lys Ile Asn
            20                  25                  30
Asn Met Gly Trp Tyr Arg Gln Ala Pro Gly Lys Gln Arg Asp Leu Val
            35                  40                  45
Ala Gln Ile Thr Pro Gly Gly Ile Thr Asp Tyr Ala Asp Ser Val Lys
        50                  55                  60
Gly Arg Phe Thr Ile Ser Arg Asp Asn Ser Lys Asn Thr Leu Tyr Leu
65                  70                  75                  80
Gln Met Asn Ser Leu Arg Pro Glu Asp Thr Ala Val Tyr Tyr Cys Asn
                85                  90                  95
Ala Glu Ile Leu Lys Arg Ala Tyr Ile Asp Val Tyr Val Asn Tyr Trp
            100                 105                 110
```

-continued

```
Gly Gln Gly Thr Leu Val Thr Val Lys Pro Gly Gly Gly Ser Gly
            115                 120                 125
Gly Gly Gly Ser Gly Gly Gly Ser Gly Gly Gly Ser Gly Gly
        130                 135                 140
Gly Gly Ser Gly Gly Gly Ser Gly Gly Gly Ser Glu Val Gln
145                 150                 155                 160
Leu Leu Glu Ser Gly Gly Glu Val Gln Pro Gly Gly Ser Leu Arg
                165                 170                 175
Leu Ser Cys Ala Ala Ser Gly Thr Phe Asp Lys Ile Asn Asn Met Gly
            180                 185                 190
Trp Tyr Arg Gln Ala Pro Gly Lys Gln Arg Asp Leu Val Ala Gln Ile
            195                 200                 205
Thr Pro Gly Gly Ile Thr Asp Tyr Ala Asp Ser Val Lys Gly Arg Phe
            210                 215                 220
Thr Ile Ser Arg Asp Asn Ser Lys Asn Thr Leu Tyr Leu Gln Met Asn
225                 230                 235                 240
Ser Leu Arg Pro Glu Asp Thr Ala Val Tyr Tyr Cys Asn Ala Glu Ile
                245                 250                 255
Leu Lys Arg Ala Tyr Ile Asp Val Tyr Val Asn Tyr Trp Gly Gln Gly
            260                 265                 270
Thr Leu Val Thr Val Lys Pro Gly Gly Gly Ser Gly Gly Gly Gly
            275                 280                 285
Ser Gly Gly Gly Gly Ser Gly Gly Gly Ser Gly Gly Gly Gly Ser
        290                 295                 300
Gly Gly Gly Ser Gly Gly Gly Ser Glu Val Gln Leu Leu Glu
305                 310                 315                 320
Ser Gly Gly Glu Val Gln Pro Gly Gly Ser Leu Arg Leu Ser Cys
                325                 330                 335
Ala Ala Ser Gly Thr Phe Asp Lys Ile Asn Asn Met Gly Trp Tyr Arg
            340                 345                 350
Gln Ala Pro Gly Lys Gln Arg Asp Leu Val Ala Gln Ile Thr Pro Gly
            355                 360                 365
Gly Ile Thr Asp Tyr Ala Asp Ser Val Lys Gly Arg Phe Thr Ile Ser
            370                 375                 380
Arg Asp Asn Ser Lys Asn Thr Leu Tyr Leu Gln Met Asn Ser Leu Arg
385                 390                 395                 400
Pro Glu Asp Thr Ala Val Tyr Tyr Cys Asn Ala Glu Ile Leu Lys Arg
                405                 410                 415
Ala Tyr Ile Asp Val Tyr Val Asn Tyr Trp Gly Gln Gly Thr Leu Val
            420                 425                 430
Thr Val Lys Pro Gly Gly Gly Ser Gly Gly Gly Gly Ser Gly Gly
            435                 440                 445
Gly Gly Ser Gly Gly Gly Gly Ser Gly Gly Gly Ser Gly Gly Gly
        450                 455                 460
Gly Ser Gly Gly Gly Ser Glu Val Gln Leu Leu Glu Ser Gly Gly
465                 470                 475                 480
Gly Glu Val Gln Pro Gly Gly Ser Leu Arg Leu Ser Cys Ala Ala Ser
                485                 490                 495
Gly Thr Phe Asp Lys Ile Asn Asn Met Gly Trp Tyr Arg Gln Ala Pro
            500                 505                 510
Gly Lys Gln Arg Asp Leu Val Ala Gln Ile Thr Pro Gly Gly Ile Thr
            515                 520                 525
```

Asp Tyr Ala Asp Ser Val Lys Gly Arg Phe Thr Ile Ser Arg Asp Asn
    530                 535                 540

Ser Lys Asn Thr Leu Tyr Leu Gln Met Asn Ser Leu Arg Pro Glu Asp
545                 550                 555                 560

Thr Ala Val Tyr Tyr Cys Asn Ala Glu Ile Leu Lys Arg Ala Tyr Ile
                565                 570                 575

Asp Val Tyr Val Asn Tyr Trp Gly Gln Gly Thr Leu Val Thr Val Lys
                580                 585                 590

Pro Gly Gly
    595

<210> SEQ ID NO 127
<211> LENGTH: 218
<212> TYPE: PRT
<213> ORGANISM: Artificial Sequence
<220> FEATURE:
<223> OTHER INFORMATION: chemically synthesized

<400> SEQUENCE: 127

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 128
<211> LENGTH: 10
<212> TYPE: PRT
<213> ORGANISM: Artificial Sequence
<220> FEATURE:
<223> OTHER INFORMATION: chemically synthesized

<400> SEQUENCE: 128

Ser Gly Leu Thr Phe Pro Asn Tyr Gly Met
1               5                   10

<210> SEQ ID NO 129
<211> LENGTH: 10
<212> TYPE: PRT
<213> ORGANISM: Artificial Sequence
<220> FEATURE:
<223> OTHER INFORMATION: chemically synthesized

<400> SEQUENCE: 129

Val Ile Tyr Trp Ser Gly Gly Thr Val Phe
1               5                   10

<210> SEQ ID NO 130
<211> LENGTH: 17
<212> TYPE: PRT
<213> ORGANISM: Artificial Sequence
<220> FEATURE:
<223> OTHER INFORMATION: chemically synthesized

<400> SEQUENCE: 130

Ala Val Thr Ile Arg Gly Ala Ala Thr Gln Thr Trp Lys Tyr Asp Tyr
1               5                   10                  15

Trp

<210> SEQ ID NO 131
<211> LENGTH: 10
<212> TYPE: PRT
<213> ORGANISM: Artificial Sequence
<220> FEATURE:
<223> OTHER INFORMATION: chemically synthesized

<400> SEQUENCE: 131

Ala Ile Tyr Trp Ser Gly Gly Thr Val Tyr
1               5                   10

<210> SEQ ID NO 132
<211> LENGTH: 10
<212> TYPE: PRT
<213> ORGANISM: Artificial Sequence
<220> FEATURE:
<223> OTHER INFORMATION: chemically synthesized

<400> SEQUENCE: 132

Ala Ile Tyr Trp Ser Gly Gly Thr Val Phe
1               5                   10

<210> SEQ ID NO 133
<211> LENGTH: 10
<212> TYPE: PRT
<213> ORGANISM: Artificial Sequence
<220> FEATURE:
<223> OTHER INFORMATION: chemically synthesized

<400> SEQUENCE: 133

Val Ile Tyr Trp Ser Gly Gly Thr Val Tyr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: chemically synthesized

<400> SEQUENCE: 134

Ser Gly Arg Thr Val Ser Asn Tyr Ala Met

```
<210> SEQ ID NO 135
<211> LENGTH: 10
<212> TYPE: PRT
<213> ORGANISM: Artificial Sequence
<220> FEATURE:
<223> OTHER INFORMATION: chemically synthesized

<400> SEQUENCE: 135

Ala Leu Asn Trp Gly Gly Asp Thr Thr Ser
1               5                   10

<210> SEQ ID NO 136
<211> LENGTH: 18
<212> TYPE: PRT
<213> ORGANISM: Artificial Sequence
<220> FEATURE:
<223> OTHER INFORMATION: chemically synthesized

<400> SEQUENCE: 136

Ala Ala Ala Gln Ser Phe Arg Arg Gly Gly Ala Pro Tyr Gly Asp Asn
1               5                   10                  15

Tyr Trp

<210> SEQ ID NO 137
<211> LENGTH: 10
<212> TYPE: PRT
<213> ORGANISM: Artificial Sequence
<220> FEATURE:
<223> OTHER INFORMATION: chemically synthesized

<400> SEQUENCE: 137

Ala Leu Asn Trp Gly Gly Asp Thr Thr Tyr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: chemically synthesized

<400> SEQUENCE: 138

Ser Gly Arg Ala Leu Thr Gly Tyr His Met Ala Trp
1               5                   10

<210> SEQ ID NO 139
<211> LENGTH: 10
<212> TYPE: PRT
<213> ORGANISM: Artificial Sequence
<220> FEATURE:
<223> OTHER INFORMATION: chemically synthesized

<400> SEQUENCE: 139

Tyr Gly Ile Trp Asp Arg Ala Gly Ala Ala
1               5                   10

<210> SEQ ID NO 140
<211> LENGTH: 17
<212> TYPE: PRT
<213> ORGANISM: Artificial Sequence
<220> FEATURE:
<223> OTHER INFORMATION: chemically synthesized

<400> SEQUENCE: 140
```

```
Ala Ser Met Ala Val Arg Thr Tyr Tyr Ser Pro Arg Ser Tyr Asp Ser
1               5                   10                  15

Trp

<210> SEQ ID NO 141
<211> LENGTH: 12
<212> TYPE: PRT
<213> ORGANISM: Artificial Sequence
<220> FEATURE:
<223> OTHER INFORMATION: chemically synthesized

<400> SEQUENCE: 141

Ser Gly Arg Ala Leu Thr Gly Tyr His Met Ser Trp
1               5                   10

<210> SEQ ID NO 142
<211> LENGTH: 12
<212> TYPE: PRT
<213> ORGANISM: Artificial Sequence
<220> FEATURE:
<223> OTHER INFORMATION: chemically synthesized

<400> SEQUENCE: 142

Ser Gly Ser Thr Phe Ser Ser Leu Asp Met Gly Trp
1               5                   10

<210> SEQ ID NO 143
<211> LENGTH: 10
<212> TYPE: PRT
<213> ORGANISM: Artificial Sequence
<220> FEATURE:
<223> OTHER INFORMATION: chemically synthesized

<400> SEQUENCE: 143

Ala Ile Ser Arg Ser Gly Asp Asn Ile Tyr
1               5                   10

<210> SEQ ID NO 144
<211> LENGTH: 22
<212> TYPE: PRT
<213> ORGANISM: Artificial Sequence
<220> FEATURE:
<223> OTHER INFORMATION: chemically synthesized

<400> SEQUENCE: 144

Ala Val Asp Ser Gln Pro Thr Tyr Ser Gly Gly Val Tyr Tyr Pro Arg
1               5                   10                  15

Tyr Gly Met Asp Val Trp
            20

<210> SEQ ID NO 145
<211> LENGTH: 22
<212> TYPE: PRT
<213> ORGANISM: Artificial Sequence
<220> FEATURE:
<223> OTHER INFORMATION: chemically synthesized

<400> SEQUENCE: 145

Ala Val Asp Thr Gln Pro Thr Tyr Ser Gly Gly Val Tyr Tyr Pro Arg
1               5                   10                  15

Tyr Gly Met Asp Val Trp
            20

<210> SEQ ID NO 146
<211> LENGTH: 22
```

```
<212> TYPE: PRT
<213> ORGANISM: Artificial Sequence
<220> FEATURE:
<223> OTHER INFORMATION: chemically synthesized

<400> SEQUENCE: 146

Ala Val Asp Ala Gln Pro Thr Tyr Ser Gly Gly Val Tyr Tyr Pro Arg
1               5                   10                  15

Tyr Gly Met Asp Val Trp
            20

<210> SEQ ID NO 147
<211> LENGTH: 22
<212> TYPE: PRT
<213> ORGANISM: Artificial Sequence
<220> FEATURE:
<223> OTHER INFORMATION: chemically synthesized

<400> SEQUENCE: 147

Ala Val Glu Ser Gln Pro Thr Tyr Ser Gly Gly Val Tyr Tyr Pro Arg
1               5                   10                  15

Tyr Gly Met Asp Val Trp
            20

<210> SEQ ID NO 148
<211> LENGTH: 22
<212> TYPE: PRT
<213> ORGANISM: Artificial Sequence
<220> FEATURE:
<223> OTHER INFORMATION: chemically synthesized

<400> SEQUENCE: 148

Ala Val Asp Ser Gln Pro Thr Tyr Ser Gly Gly Val Tyr Tyr Pro Arg
1               5                   10                  15

Tyr Gly Tyr Asp Val Trp
            20

<210> SEQ ID NO 149
<211> LENGTH: 22
<212> TYPE: PRT
<213> ORGANISM: Artificial Sequence
<220> FEATURE:
<223> OTHER INFORMATION: chemically synthesized

<400> SEQUENCE: 149

Ala Val Asp Ser Gln Pro Thr Tyr Ser Gly Gly Val Tyr Tyr Pro Arg
1               5                   10                  15

Tyr Gly Leu Asp Val Trp
            20

<210> SEQ ID NO 150
<211> LENGTH: 22
<212> TYPE: PRT
<213> ORGANISM: Artificial Sequence
<220> FEATURE:
<223> OTHER INFORMATION: chemically synthesized

<400> SEQUENCE: 150

Ala Val Asp Ala Gln Pro Thr Tyr Ser Gly Gly Val Tyr Tyr Pro Arg
1               5                   10                  15

Tyr Gly Ala Asp Val Trp
            20

<210> SEQ ID NO 151
```

```
<211> LENGTH: 22
<212> TYPE: PRT
<213> ORGANISM: Artificial Sequence
<220> FEATURE:
<223> OTHER INFORMATION: chemically synthesized

<400> SEQUENCE: 151

Ala Val Asp Ala Gln Pro Thr Tyr Ser Gly Gly Val Tyr Tyr Pro Arg
1               5                   10                  15

Tyr Gly His Asp Val Trp
            20

<210> SEQ ID NO 152
<211> LENGTH: 22
<212> TYPE: PRT
<213> ORGANISM: Artificial Sequence
<220> FEATURE:
<223> OTHER INFORMATION: chemically synthesized

<400> SEQUENCE: 152

Ala Val Asp Ala Gln Pro Thr Tyr Ser Gly Gly Val Tyr Tyr Pro Arg
1               5                   10                  15

Tyr Gly Asn Asp Val Trp
            20

<210> SEQ ID NO 153
<211> LENGTH: 22
<212> TYPE: PRT
<213> ORGANISM: Artificial Sequence
<220> FEATURE:
<223> OTHER INFORMATION: chemically synthesized

<400> SEQUENCE: 153

Ala Val Asp Ala Gln Pro Thr Tyr Ser Gly Gly Val Tyr Tyr Pro Arg
1               5                   10                  15

Tyr Gly Pro Asp Val Trp
            20

<210> SEQ ID NO 154
<211> LENGTH: 22
<212> TYPE: PRT
<213> ORGANISM: Artificial Sequence
<220> FEATURE:
<223> OTHER INFORMATION: chemically synthesized

<400> SEQUENCE: 154

Ala Val Asp Ala Gln Pro Thr Tyr Ser Gly Gly Val Tyr Tyr Pro Arg
1               5                   10                  15

Tyr Gly Gln Asp Val Trp
            20

<210> SEQ ID NO 155
<211> LENGTH: 22
<212> TYPE: PRT
<213> ORGANISM: Artificial Sequence
<220> FEATURE:
<223> OTHER INFORMATION: chemically synthesized

<400> SEQUENCE: 155

Ala Val Asp Ala Gln Pro Thr Tyr Ser Gly Gly Val Tyr Tyr Pro Arg
1               5                   10                  15

Tyr Gly Arg Asp Val Trp
            20
```

```
<210> SEQ ID NO 156
<211> LENGTH: 22
<212> TYPE: PRT
<213> ORGANISM: Artificial Sequence
<220> FEATURE:
<223> OTHER INFORMATION: chemically synthesized

<400> SEQUENCE: 156

Ala Val Asp Ala Gln Pro Thr Tyr Ser Gly Gly Val Tyr Tyr Pro Arg
1               5                   10                  15

Tyr Gly Ser Asp Val Trp
            20

<210> SEQ ID NO 157
<211> LENGTH: 22
<212> TYPE: PRT
<213> ORGANISM: Artificial Sequence
<220> FEATURE:
<223> OTHER INFORMATION: chemically synthesized

<400> SEQUENCE: 157

Ala Val Asp Ala Gln Pro Thr Tyr Ser Gly Gly Val Tyr Tyr Pro Arg
1               5                   10                  15

Tyr Gly Thr Asp Val Trp
            20

<210> SEQ ID NO 158
<211> LENGTH: 22
<212> TYPE: PRT
<213> ORGANISM: Artificial Sequence
<220> FEATURE:
<223> OTHER INFORMATION: chemically synthesized

<400> SEQUENCE: 158

Ala Val Asp Ala Gln Pro Thr Tyr Ser Gly Gly Val Tyr Tyr Pro Arg
1               5                   10                  15

Tyr Gly Val Asp Val Trp
            20

<210> SEQ ID NO 159
<211> LENGTH: 12
<212> TYPE: PRT
<213> ORGANISM: Artificial Sequence
<220> FEATURE:
<223> OTHER INFORMATION: chemically synthesized

<400> SEQUENCE: 159

Ser Gly Arg Ala Phe Ser Asn Tyr Ala Leu Gly Trp
1               5                   10

<210> SEQ ID NO 160
<211> LENGTH: 10
<212> TYPE: PRT
<213> ORGANISM: Artificial Sequence
<220> FEATURE:
<223> OTHER INFORMATION: chemically synthesized

<400> SEQUENCE: 160

Ala Ile Asn Trp Asn Gly Glu Asn Arg Tyr
1               5                   10

<210> SEQ ID NO 161
<211> LENGTH: 18
<212> TYPE: PRT
<213> ORGANISM: Artificial Sequence
<220> FEATURE:
```

```
<223> OTHER INFORMATION: chemically synthesized

<400> SEQUENCE: 161

Ala Ala Ala Leu Ser Phe Arg Leu Gly Gly Glu Pro Tyr Gly Asp Ala
1               5                   10                  15
Tyr Trp

<210> SEQ ID NO 162
<211> LENGTH: 12
<212> TYPE: PRT
<213> ORGANISM: Artificial Sequence
<220> FEATURE:
<223> OTHER INFORMATION: chemically synthesized

<400> SEQUENCE: 162

Ser Gly Arg Ala Phe Ser Asn Tyr Ala Met Ser Trp
1               5                   10

<210> SEQ ID NO 163
<211> LENGTH: 10
<212> TYPE: PRT
<213> ORGANISM: Artificial Sequence
<220> FEATURE:
<223> OTHER INFORMATION: chemically synthesized

<400> SEQUENCE: 163

Ser Gly Ser Ile Phe Thr Asn Asn Ala Met
1               5                   10

<210> SEQ ID NO 164
<211> LENGTH: 10
<212> TYPE: PRT
<213> ORGANISM: Artificial Sequence
<220> FEATURE:
<223> OTHER INFORMATION: chemically synthesized

<400> SEQUENCE: 164

Gln Ile Thr Met Gly Gly Gly Ile Thr Asn
1               5                   10

<210> SEQ ID NO 165
<211> LENGTH: 16
<212> TYPE: PRT
<213> ORGANISM: Artificial Sequence
<220> FEATURE:
<223> OTHER INFORMATION: chemically synthesized

<400> SEQUENCE: 165

Asn Ala Glu Val Lys Ser Ala Asp Trp Gly Ala Tyr Ala Asn Tyr Trp
1               5                   10                  15

<210> SEQ ID NO 166
<211> LENGTH: 10
<212> TYPE: PRT
<213> ORGANISM: Artificial Sequence
<220> FEATURE:
<223> OTHER INFORMATION: chemically synthesized

<400> SEQUENCE: 166

Ala Ile Thr Met Gly Gly Gly Ile Thr Tyr
1               5                   10

<210> SEQ ID NO 167
<211> LENGTH: 10
<212> TYPE: PRT
<213> ORGANISM: Artificial Sequence
```

```
<220> FEATURE:
<223> OTHER INFORMATION: chemically synthesized

<400> SEQUENCE: 167

Gln Ile Thr Met Gly Gly Gly Ile Thr Tyr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: chemically synthesized

<400> SEQUENCE: 168

Ser Gly Arg Ser Ile Ser Asn Tyr Ala Met
1               5                   10

<210> SEQ ID NO 169
<211> LENGTH: 10
<212> TYPE: PRT
<213> ORGANISM: Artificial Sequence
<220> FEATURE:
<223> OTHER INFORMATION: chemically synthesized

<400> SEQUENCE: 169

Ala Ser Val Trp Asn Asn Gly Gly Asn Tyr
1               5                   10

<210> SEQ ID NO 170
<211> LENGTH: 19
<212> TYPE: PRT
<213> ORGANISM: Artificial Sequence
<220> FEATURE:
<223> OTHER INFORMATION: chemically synthesized

<400> SEQUENCE: 170

Val Val Ala Arg Thr Pro Glu Thr Pro Ile Thr Ser Ala Arg Gly Ala
1               5                   10                  15

Asn Tyr Trp

<210> SEQ ID NO 171
<211> LENGTH: 10
<212> TYPE: PRT
<213> ORGANISM: Artificial Sequence
<220> FEATURE:
<223> OTHER INFORMATION: chemically synthesized

<400> SEQUENCE: 171

Ala Ser Val Trp Asn Gln Gly Gly Asn Tyr
1               5                   10

<210> SEQ ID NO 172
<211> LENGTH: 10
<212> TYPE: PRT
<213> ORGANISM: Artificial Sequence
<220> FEATURE:
<223> OTHER INFORMATION: chemically synthesized

<400> SEQUENCE: 172

Ala Ser Val Trp Asn Asn Ala Gly Asn Tyr
1               5                   10

<210> SEQ ID NO 173
<211> LENGTH: 10
<212> TYPE: PRT
```

```
<213> ORGANISM: Artificial Sequence
<220> FEATURE:
<223> OTHER INFORMATION: chemically synthesized

<400> SEQUENCE: 173

Ser Gly Arg Ala Ala Ser Asp Tyr Ala Val
1               5                   10

<210> SEQ ID NO 174
<211> LENGTH: 10
<212> TYPE: PRT
<213> ORGANISM: Artificial Sequence
<220> FEATURE:
<223> OTHER INFORMATION: chemically synthesized

<400> SEQUENCE: 174

Ala Cys Asn Trp Ser Gly Glu Asp Thr Val
1               5                   10

<210> SEQ ID NO 175
<211> LENGTH: 21
<212> TYPE: PRT
<213> ORGANISM: Artificial Sequence
<220> FEATURE:
<223> OTHER INFORMATION: chemically synthesized

<400> SEQUENCE: 175

Ala Ala Ala Pro Ser Phe Ser Arg Ser Val Leu Asp Gly Asn Leu Ser
1               5                   10                  15

Gln Ile Asp Tyr Trp
            20

<210> SEQ ID NO 176
<211> LENGTH: 10
<212> TYPE: PRT
<213> ORGANISM: Artificial Sequence
<220> FEATURE:
<223> OTHER INFORMATION: chemically synthesized

<400> SEQUENCE: 176

Ser Gly Arg Ala Ala Ser Asp Tyr Ala Met
1               5                   10

<210> SEQ ID NO 177
<211> LENGTH: 9
<212> TYPE: PRT
<213> ORGANISM: Artificial Sequence
<220> FEATURE:
<223> OTHER INFORMATION: chemically synthesized

<400> SEQUENCE: 177

Ile Asn Trp Gly Gly Glu Asp Thr Val
1               5

<210> SEQ ID NO 178
<211> LENGTH: 10
<212> TYPE: PRT
<213> ORGANISM: Artificial Sequence
<220> FEATURE:
<223> OTHER INFORMATION: chemically synthesized

<400> SEQUENCE: 178

Ser Gly Arg Thr Phe Thr Asn Tyr Ala Met
1               5                   10

<210> SEQ ID NO 179
```

```
<211> LENGTH: 10
<212> TYPE: PRT
<213> ORGANISM: Artificial Sequence
<220> FEATURE:
<223> OTHER INFORMATION: chemically synthesized

<400> SEQUENCE: 179

Ala Ile Asn Trp Ser Gly Asp Ser Thr Tyr
1               5                   10

<210> SEQ ID NO 180
<211> LENGTH: 18
<212> TYPE: PRT
<213> ORGANISM: Artificial Sequence
<220> FEATURE:
<223> OTHER INFORMATION: chemically synthesized

<400> SEQUENCE: 180

Ala Ser Ala Glu Ser Phe Ser Arg Gly Gly Leu Pro Tyr Gly Met Asn
1               5                   10                  15

Tyr Trp

<210> SEQ ID NO 181
<211> LENGTH: 10
<212> TYPE: PRT
<213> ORGANISM: Artificial Sequence
<220> FEATURE:
<223> OTHER INFORMATION: chemically synthesized

<400> SEQUENCE: 181

Ser Val Ser Thr Phe Gly Thr Ser Pro Val
1               5                   10

<210> SEQ ID NO 182
<211> LENGTH: 10
<212> TYPE: PRT
<213> ORGANISM: Artificial Sequence
<220> FEATURE:
<223> OTHER INFORMATION: chemically synthesized

<400> SEQUENCE: 182

Ala Ile Arg Trp Asp Gly Val Gly Ala Tyr
1               5                   10

<210> SEQ ID NO 183
<211> LENGTH: 20
<212> TYPE: PRT
<213> ORGANISM: Artificial Sequence
<220> FEATURE:
<223> OTHER INFORMATION: chemically synthesized

<400> SEQUENCE: 183

Ala Leu Pro Arg Arg Gly Asp Ser Glu Leu Pro Ser Thr Val Lys Glu
1               5                   10                  15

Tyr Gly Tyr Trp
            20

<210> SEQ ID NO 184
<211> LENGTH: 10
<212> TYPE: PRT
<213> ORGANISM: Artificial Sequence
<220> FEATURE:
<223> OTHER INFORMATION: chemically synthesized

<400> SEQUENCE: 184

Ala Ile Arg Trp Glu Gly Val Gly Ala Tyr
```

```
1               5                   10
```

<210> SEQ ID NO 185
<211> LENGTH: 10
<212> TYPE: PRT
<213> ORGANISM: Artificial Sequence
<220> FEATURE:
<223> OTHER INFORMATION: chemically synthesized

<400> SEQUENCE: 185

```
Ala Ile Arg Trp Asp Ala Val Gly Ala Tyr
1               5                   10
```

<210> SEQ ID NO 186
<211> LENGTH: 20
<212> TYPE: PRT
<213> ORGANISM: Artificial Sequence
<220> FEATURE:
<223> OTHER INFORMATION: chemically synthesized

<400> SEQUENCE: 186

```
Ala Leu Pro Arg Arg Gly Glu Ser Glu Leu Pro Ser Thr Val Lys Glu
1               5                   10                  15

Tyr Gly Tyr Trp
            20
```

<210> SEQ ID NO 187
<211> LENGTH: 20
<212> TYPE: PRT
<213> ORGANISM: Artificial Sequence
<220> FEATURE:
<223> OTHER INFORMATION: chemically synthesized

<400> SEQUENCE: 187

```
Ala Leu Pro Arg Arg Gly Asp Ala Glu Leu Pro Ser Thr Val Lys Glu
1               5                   10                  15

Tyr Gly Tyr Trp
            20
```

<210> SEQ ID NO 188
<211> LENGTH: 10
<212> TYPE: PRT
<213> ORGANISM: Artificial Sequence
<220> FEATURE:
<223> OTHER INFORMATION: chemically synthesized

<400> SEQUENCE: 188

```
Ser Gly Arg Thr Leu Ser Ala Tyr Leu Met
1               5                   10
```

<210> SEQ ID NO 189
<211> LENGTH: 10
<212> TYPE: PRT
<213> ORGANISM: Artificial Sequence
<220> FEATURE:
<223> OTHER INFORMATION: chemically synthesized

<400> SEQUENCE: 189

```
Arg Ile Arg Trp Asn Glu Gly Asp Thr Tyr
1               5                   10
```

<210> SEQ ID NO 190
<211> LENGTH: 15
<212> TYPE: PRT
<213> ORGANISM: Artificial Sequence
<220> FEATURE:

-continued

```
<223> OTHER INFORMATION: chemically synthesized

<400> SEQUENCE: 190

Ala Ala Arg Ser Ile Phe Asn Pro Ser Asp Gln Tyr Val Tyr Trp
1               5                   10                  15
```

MULTIVALENT AND MULTISPECIFIC DR5-BINDING FUSION PROTEINS

RELATED APPLICATIONS

This application claims the benefit of U.S. Provisional Application No. 62/193,309, filed Jul. 16, 2015, the contents of which are incorporated herein by reference in their entirety.

The contents of the text file named "INHI021001US_ST25.txt", which was created on Oct. 4, 2016 and is 210 KB in size, are hereby incorporated by reference in their entirety.

FIELD OF THE INVENTION

The disclosure relates generally to molecules that specifically engage death receptor 5 (DR5), a member of the TNF receptor superfamily (TNFRSF). More specifically the disclosure relates to multivalent and multispecific molecules that bind at least DR5.

BACKGROUND OF THE INVENTION

The tumor necrosis factor receptor superfamily consists of several structurally related cell surface receptors. Activation by multimeric ligands is common feature of many of these receptors. Many members of the TNFRSF have therapeutic utility in numerous pathologies, if activated properly. Importantly to properly agonize this receptor family often requires higher order clustering and conventional bivalent antibodies are not ideal for this. Therefore, there exists a therapeutic need for more potent agonist molecules of the TNFRSF.

SUMMARY OF THE INVENTION

The disclosure provides multivalent fusion polypeptides that bind at least death receptor 5 (DR5, also known as TRAIL receptor 2 (TRAILR2), or tumor necrosis factor receptor superfamily member 10B (TNFRSF10B)). These DR5 binding fusion polypeptides are also referred to herein as DR5-targeting molecules. DR5 is a member of the TNF receptor superfamily (TNFRSF) and a cell surface receptor of the TNF-receptor superfamily that binds TNF-related apoptosis-inducing ligand (TRAIL). TRAIL evolved to play critical roles in mammalian development and host defense by selectively eradicating unwanted, infected and malignant cells from healthy cell populations. On binding the TNF receptor family members DR4 or DR5, TRAIL induces cell death via caspase-dependent apoptosis. DR5 appears to be the primary receptor on tumor cells that facilitates the observed tumor biased activity of the TRAIL pathway. DR5 is activated by the natural ligand TRAIL, which brings three DR5 receptors within close proximity thereby activating intracellular caspase-8 and initiating activation of other death-inducing caspases, such as caspases-9 and caspases-3. Thus initiation of this cell death pathway requires clustering of DR5 receptors for efficient cell death.

Conventional antibodies targeting members of the TNF receptor superfamily (TNFRSF) have been shown to require an exogenous crosslinking to achieve sufficient agonist activity, as evidenced by the necessity for Fc-gamma Receptor (FcγRs) for the activity antibodies to DR4, DR5, GITR and OX40 (Ichikawa et at 2001 al Nat. Med. 7, 954-960, Li et at 2008 Drug Dev. Res. 69, 69-82; Pukac et al 2005 Br. J. Cancer 92, 1430-1441; Yanda et at 2008 Ann. Oncol. 19, 1060-1067; Yang et al 2007 Cancer Lett. 251:146-157; Bulliard et al 2013 JEM 210(9): 1685; Bulliard et at 2014 Immunol and Cell Biol 92: 475-480). In addition to crosslinking via FcγRs, other exogenous agents including addition of the oligomeric ligand or antibody binding entities (e.g. protein A and secondary antibodies) have be demonstrated to enhance anti-TNFRSF antibody clustering and downstream signaling. For instance, in vitro agonist activity of the CD137 antibody, PF-05082566, requires crosslinking via a secondary antibody (Fisher et at Cancer Immunol Immunother 2012 61:1721-1733). These findings suggest the need for clustering of TNFRSFs beyond a dimer.

Efforts to clinically exploit the TRAIL pathway for cancer therapy relied upon a recombinant version of the natural ligand TRAIL and antibodies specific for DR5. Antibody agonists targeting DR5 required a crosslinking agent in preclinical in vitro experiments. For example, the addition of the DR5 ligand TRAIL enhanced the apoptosis inducing ability of an anti-DR5 antibody, AMG655 (Graves et al 2014 Cancer Cell 26: 177-189). Conventional antibodies are bivalent and capable clustering only two DR5 receptors (one per each FAB arm). Consistent with other members of the TNFRSF, clustering of two DR5 receptors is insufficient to mediate signaling and activate the cell death pathway in vitro. Surprisingly in vivo administration of DR5 targeting antibodies in pre-clinical mouse models of human cancers showed significant activity in a wide variety of tumor types. This activity was later shown to be dependent on mouse FcgammaR (FcγR) receptors. Clinical studies in humans failed to reproduce the robust responses seen in these pre-clinical mouse models. The lack of activity in humans is hypothesized to be due to insufficient antibody crosslinking. This may be due to differences in serum IgG, FcγR and or TRAIL concentrations between immune compromised mice and human cancer patients.

The present disclosure provides multivalent fusion proteins targeting DR5 that are capable of potently agonizing DR5 signaling mediating direct cell death. The fusion proteins of the present disclosure can be bivalent, trivalent, tetravalent, pentavalent, or hexavalent. Importantly, the fusion proteins of the present disclosure are capable of eliciting apoptosis of DR5 expressing cells independently of exogenous crosslinking agents.

In some embodiments, the fusion proteins of the present disclosure incorporate a binding domain (DR5BD) that binds DR5. In preferred embodiments, the DR5 binding DR5BD does not bind DR4, decoy R1, decoy R2, Osteopontin, or any other TNFRSF member. In preferred embodiments the DR5 binding DR5BD binds human and cynomolgus monkey DR5. In some embodiments, the DR5 binding DR5BD blocks the interaction of DR5 and its ligand TRAIL. In other embodiments, the DR5 binding DR5BD does not block the interaction of DR5 and its ligand TRAIL. In some embodiments, the fusion protein of the present disclosure incorporates multiple DR5 binding DR5BDs that recognize distinct epitopes on DR5. In some embodiments, the fusion protein of the present disclosure incorporates multiple DR5 binding DR5BDs, wherein some DR5BDs block the DR5-TRAIL interaction and other do not block the DR5-TRAIL interaction. In preferred embodiments, DR5 targeting fusion proteins of the present disclosure induce direct cell death of tumor cells. The DR5 targeting fusion proteins of the present disclosure have utility in treating tumors both hematologic and solid in nature.

The present disclosure provides multivalent DR5 binding fusion proteins, which comprise 2 or more DR5 binding domains (DR5BDs). In some embodiments, the fusion proteins of the present disclosure have utility in treating neoplasms. In some embodiments, the fusion proteins of the present disclosure bind DR5 expressed on a tumor cell. In some embodiments, the fusion protein contains two or more different DR5BDs, where each DR5BD binds DR5. In some embodiments, the fusion protein contains multiple copies of a DR5BD that binds DR5. For example, in some embodiments, the fusion protein contains at least two copies of a DR5BD that binds DR5. In some embodiments, the fusion protein contains at least three copies of a DR5BD that binds DR5. In some embodiments, the fusion protein contains at least four copies of a DR5BD that binds DR5. In some embodiments, the fusion protein contains at least five copies of a DR5BD that binds DR5. In some embodiments, the fusion protein contains at least six copies of a DR5BD that binds DR5. In some embodiments, the fusion protein contains six or more copies of a DR5BD that binds DR5.

Multivalent DR5 binding fusion proteins of the present disclosure are capable of inducing direct cell death of damaged, transformed, virally infected, or neoplastic cells without the need for exogenous crosslinking agents. In addition, DR5 binding fusion proteins of the present disclosure do not induce direct cell death of normal, non-transformed cells, non-virally infected or non-neoplastic cells. Importantly, the DR5BDs and fusion proteins composed thereof of the present disclosure have reduced or eliminated recognition by pre-existing antibodies directed toward single domain antibodies present in some human subjects.

TAS266 is a tetravalent humanized DR5-targeting nanobody-based therapeutic, which displays superior apoptosis inducing capacity compared to bivalent antibodies, without the need for additional crosslinking by FcγRs. (Huet, H. A., et al., Multivalent nanobodies targeting death receptor 5 elicit superior tumor cell killing through efficient caspase induction. mAbs Vol. 6, Iss. 6, 2014).

It has previously been predicted that approximately half of healthy human subjects have pre-existing antibodies recognizing human single domain antibodies, known as human anti-VH autoantibodies (HAVH), which target an epitope within human VH domains (Holland et al. J Clin Immunol (2013) 33:1192-1203)). Thus, it expected that humanized camelid-derived VHHs would also be recognized by HAVH autoantibodies as the target epitope seems to be cryptic and located within human germline framework regions. The interaction of HAVH autoantibodies (also called anti-drug antibodies (ADA) or anti-single domain antibodies (ASDA), herein) can cause enhanced clustering and activation. In agreement with this hypothesis, in a Phase I clinical trial, administration of TAS266 induced elevated AST and ALT levels indicative of hepatotoxicity. Elevated enzyme levels occurred in 3 out of 4 patients leading to termination of the TAS266 trial. It was noted that the 3 patients exhibiting clinical signs of hepatotoxicity had pre-existing ADA leading trial investigators to suspect that ADA-induced hyper-clustering of the DR5 receptor causing toxicity. It was noted that the one patient without ADA had no signs of toxicity (Isaacs R, Bilic S, Kentsch K, Huet H A, Hofmann M, Rasco D, Kundamal N, Tang Z, Cooksey J, Mahipal A. Unexpected hepatotoxicity in a phase I study of TAS266, a novel tetravalent agonistic Nanobody® targeting the DR5 receptor. Papadopoulos KP1, Cancer Chemother Pharmacol. 2015 May; 75(5):887-95. doi: 10.1007/s00280-015-2712-0. Epub 2015 Feb. 27.). In support of this idea, it has been well-documented that aggregated forms of DR5 agonists induce hepatotoxicity whereas non-aggregated forms do not (J Lemke, S von Karstedt, J Zinngrebe and H Walczak. Getting TRAIL back on track for cancer therapy. Cell Death and Differentiation (2014) 21, 1350-1364).

In some embodiments, the fusion protein contains at least one DR5BD that comprises an amino acid sequence selected from the group consisting of SEQ ID NO: 15-91. In some embodiments, the fusion protein contains two or more copies of a DR5BD that comprises an amino acid sequence selected from the group consisting of SEQ ID NO: 15-91. In some embodiments, the fusion protein contains three or more copies of a DR5BD that comprises an amino acid sequence selected from the group consisting of SEQ ID NO: 15-91. In some embodiments, the fusion protein contains four or more copies of a DR5BD that comprises an amino acid sequence selected from the group consisting of SEQ ID NO: 15-91. In some embodiments, the fusion protein contains five or more copies of a DR5BD that comprises an amino acid sequence selected from the group consisting of SEQ ID NO: 15-91. In some embodiments, the fusion protein contains six or more copies of a DR5BD that comprises an amino acid sequence selected from the group consisting of SEQ ID NO: 15-91.

In some embodiments, the fusion protein contains at least one DR5BD that comprises a complementarity determining region 1 (CDR1) comprising an amino acid sequence selected from the group consisting of SEQ ID NO: 31, 128, 134, 138, 141, 142, 159, 162, 163, 168, 173, 176, 178, 181, and 188; a complementarity determining region 2 (CDR2) comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a complementarity determining region 3 (CDR3) comprising an amino acid sequence selected from the group consisting of SEQ ID NO: 130, 136, 140, 144-158, 161, 165, 170, 175, 180, 183, 186, 187, and 190. In some embodiments, the fusion protein contains two or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190. In some embodiments, the fusion protein contains three or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190. In some embodiments, the fusion protein contains four or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190. In some embodiments, the fusion protein contains five or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190. In some embodiments, the fusion protein contains six or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190.

In some embodiments, the fusion protein contains at least one DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127. In some embodiments, the fusion protein contains two or more copies of a DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127. In some embodiments, the fusion protein contains three or more copies of a DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127. In some embodiments, the fusion protein contains four or more copies of a DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127. In some embodiments, the fusion protein contains five or more copies of a DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127. In some embodiments, the fusion protein contains six or more copies of a DR5BD that comprises an amino acid sequence selected from the group consisting of SEQ ID NO: 15-91 and at least one immunoglobulin Fc region polypeptide comprising an amino acid sequence selected from the group consisting of SEQ ID NOs: 1-5 or 127.

In some embodiments, the fusion protein contains at least one DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127. In some embodiments, the fusion protein contains two or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127. In some embodiments, the fusion protein contains three or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127. In some embodiments, the fusion protein contains four or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127. In some embodiments, the fusion protein contains five or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127. In some embodiments, the fusion protein contains six or more copies of a DR5BD that comprises a CDR1 comprising an amino acid sequence selected from the group consisting of SEQ ID NO: 31, 128, 134, 138, 141, 142, 159, 162, 163, 168, 173, 176, 178, 181, and 188; a CDR2 comprising an amino acid sequence selected from the group consisting of SEQ ID NO: 28, 129, 131-133, 135, 137, 139, 143, 160, 164, 166, 167, 169, 171, 172, 174, 177, 179, 182, 184, 185, and 189; and a CDR3 comprising an amino acid sequence selected from the group consisting of SEQ ID NO: 130, 136, 140, 144-158, 161, 165, 170, 175, 180, 183, 186, 187, and 190; and at least one immunoglobulin Fc region polypeptide comprising an amino acid sequence selected from the group consisting of SEQ ID NOs: 1-5 or 127.

In some embodiments, the fusion protein comprises an amino acid sequence selected from the group consisting of SEQ ID NOs: 92-124. In some embodiments, the fusion protein comprises an amino acid sequence selected from the group consisting of SEQ ID NOs: 92-118. In some embodiments, the fusion protein comprises an amino acid sequence selected from the group consisting of SEQ ID NOs: 119-124.

The fusion proteins of the present disclosure are capable of enhanced clustering of TNFRSF members compared to non-cross-linked bivalent antibodies. The enhanced clustered of TNFRSF members mediated by the fusion proteins of the present disclosure induce enhanced TNFRSF-dependent signaling compared to non-cross-linked bivalent antibodies. In most embodiments, the fusion protein will incorporate more than 2 DR5BDs, for example, three, four, five, or six. In some embodiments the fusion protein will incorporate DR5BDs and a binding domain directed toward non-TNFRSF member antigen. In these embodiments, the interaction of the non-TNFRSF antigen is capable of providing the additional crosslinking function and TNFRSF activation is achieved with only one or two DR5BDs. In these embodiments, the fusion protein is multispecific, binding two distinct antigens. In other embodiments, the fusion protein incorporates three or more DR5BDs and a binding domain directed toward an antigen other than DR5, wherein the interaction with this additional antigen dose not enhance DR5 clustering beyond what is achieved by the DR5BD containing portion alone, but rather provides a biodistribution advantage, focusing the DR5 agonistic activity of the fusion protein to a specific site within a subject. For example, a tetravalent DR5 binding fusion protein of the present disclosure may include an additional antigen binding domain that focuses activity to a specific site, yet does not enhance the agonistic activity beyond that achieved by a tetravalent DR5 binding fusion protein lacking this additional antigen binding domain.

In some embodiments, DR5BDs of the present disclosure are derived from antibodies or antibody fragments including scFv, Fabs, single domain antibodies (sdAb), $V_{NAR}$, or VHHs. In preferred embodiments the DR5BDs are human or humanized sdAb. The sdAb fragments, can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families. In other embodiments, the DR5BDs are derived from non-antibody scaffold proteins for example but not limited to designed ankyrin repeat proteins (darpins), avimer, anticalin/lipocalins, centyrins and fynomers.

Generally the fusion proteins of the present disclosure consist of at least two or more DR5BDs operably linked via a linker polypeptide. The utilization of sdAb fragments as the specific DR5BD within the fusion the present disclosure has the benefit of avoiding the heavy chain:light chain mis-pairing problem common to many bi/multispecific antibody approaches. In addition, the fusion proteins of the present disclosure avoid the use of long linkers necessitated by many bispecific antibodies.

In some embodiments, all of the DR5BDs of the fusion protein recognize the same epitope on DR5. For example, the fusion proteins of present disclosure may incorporate 2, 3, 4, 5, or 6 DR5BDs with distinct recognition specificities toward various epitopes on DR5. In these embodiments, the fusion proteins of the present disclosure with contain multiple DR5BDs that target distinct regions of DR5. In some embodiments, the DR5BDs may recognize different epitopes on DR5 or recognize epitopes on DR5 and a distinct antigen. For example, the present disclosure provides multispecific fusion proteins incorporating DR5BDs that bind DR5 and at least a second antigen.

In some embodiments, the fusion protein of the present disclosure is composed of a single polypeptide. In other embodiments, the fusion protein of the present disclosure is composed of more than one polypeptide. For example, wherein a heterodimerization domain is incorporated into the fusion protein so as the construct an asymmetric fusion protein. For example if an immunoglobulin Fc region is incorporated into the fusion protein the CH3 domain can be used as homodimerization domain, or the CH3 dimer interface region can be mutated so as to enable heterodimerization.

In some embodiments, the fusion protein contains the DR5BDs at opposite ends. For example the DR5BDs are located on both the amino-terminal (N-terminal) portion of the fusion protein and the carboxy-terminal (C-terminal) portion of the fusion protein. In other embodiments, all the DR5BDs reside on the same end of the fusion protein. For example, DR5BDs reside on either the amino or carboxyl terminal portions of the fusion protein.

In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype. For example, the immunoglobulin Fc region of the fusion protein is of human IgG1 isotype, having an amino acid sequence:

(SEQ ID NO: 1)

PAPELLGGPS VFLFPPKPKD TLMISRTPEV TCVVVDVSHE DPEVKFNWYV

DGVEVHNAKT KPREEQYNST YRVVSVLTVL HQDWLNGKEY KCKVSNKALP

APIEKTISKA KGQPREPQVY TLPPSRDELT KNQVSLTCLV KGFYPSDIAV

EWESNGQPEN NYKTTPPVLD SDGSFFLYSK LTVDKSRWQQ GNVFSCSVMH

EALHNHYTQK SLSLSPGK

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified at amino acid Asn297 (Boxed, Kabat Numbering) to prevent to glycosylation of the fusion protein, e.g., Asn297Ala (N297A) or Asn297Asp (N297D). In some embodiments, the Fc region of the fusion protein is modified at amino acid Leu235 (Boxed, Kabat Numbering) to alter Fc receptor interactions, e.g., Leu235Glu (L235E) or Leu235Ala (L235A). In some embodiments, the Fc region of the fusion protein is modified at amino acid Leu234 (Boxed, Kabat Numbering) to alter Fc receptor interactions, e.g., Leu234Ala (L234A). In some embodiments, the Fc region of the fusion protein is altered at both amino acid 234 and 235, e.g., Leu234Ala and Leu235Ala (L234A/L235A) or Leu234Val and Leu235Ala (L234V/L235A). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region is lacks Lys447 (EU index of Kabat et at 1991 *Sequences of Proteins of Immunological Interest*).

positions to reduce Fc receptor binding: Glu233 (E233), Leu234 (L234), or Leu235 (L235). In these embodiments, Fc deletion of these three amino acids reduces the complement protein C1q binding.

```
                                              (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 isotype, having an amino acid sequence:

```
                                              (SEQ ID NO: 3)
PAPPVAGPSV FLFPPKPKDT LMISRTPEVT CVVVDVSHED PEVQFNWYVD

GVEVHNAKTK PREEQFNSTF RVVSVLTVVH QDWLNGKEYK CKVSNKGLPA

PIEKTISKTK GQPREPQVYT LPPSREEMTK NQVSLTCLVK GFYPSDISVE

WESNGQPENN YKTTPPMLDS DGSFFLYSKL TVDKSRWQQG NVFSCSVMHE

ALHNHYTQKS LSLSPGK
```

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the Fc region of the fusion protein is lacking an amino acid at one or more of the following In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region is lacks Lys447 (EU index of Kabat et at 1991 *Sequences of Proteins of Immunological Interest*).

In some embodiments, the immunoglobulin Fc region or immunologically active fragment of the fusion protein is of human IgG3 isotype, having an amino acid sequence:

```
                                              (SEQ ID NO: 4)
PAPELLGGPS VFLFPPKPKD TLMISRTPEV TCVVVDVSHE DPEVQFKWYV

DGVEVHNAKT KPREEQYNST FRVVSVLTVL HQDWLNGKEY KCKVSNKALP

APIEKTISKT KGQPREPQVY TLPPSREEMT KNQVSLTCLV KGFYPSDIAV

EWESSGQPEN NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et at 1991 *Sequences of Proteins of Immunological Interest*).

In some embodiments, the immunoglobulin Fc region or immunologically active fragment of the fusion protein is of human IgG4 isotype, having an amino acid sequence:

```
                                                        (SEQ ID NO: 5)
PAPEFLGGPS VFLFPPKPKD TLMISRTPEV TCVVVDVSQE DPEVQFNWYV

DGVEVHNAKT KPREEQFNST YRVVSVLTVL HQDWLNGKEY KCKVSNKGLP

SSIEKTISKA KGQPREPQVY TLPPSQEEMT KNQVSLTCLV KGFYPSDIAV

EWESNGQPEN NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In some embodiments, the immunoglobulin Fc region or immunologically active fragment of the fusion protein is of human IgG4 isotype, having an amino acid sequence:

```
                                                        (SEQ ID NO: 127)
PAPELLGGPS VFLFPPKPKD TLMISRTPEV TCVVVDVSQE DPEVQFNWYV

DGVEVHNAKT KPREEQFNST YRVVSVLTVL HQDWLNGKEY KCKVSNKGLP

SSIEKTISKA KGQPREPQVY TLPPSQEEMT KNQVSLTCLV KGFYPSDIAV

EWESNGQPEN NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 127.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et at 1991 *Sequences of Proteins of Immunological Interest*).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et at 2006, *J. Biol Chem Vol.* 281(33) 23514-23524), Met428Leu and Asn434Ser (M428L, N434S) (Zalevsky et at 2010 *Nature Biotech*, Vol. 28(2) 157-159), or Met252Ile, Thr256Asp, Met428Leu (M252I, T256D, M428L, respectively), (EU index of Kabat et at 1991 *Sequences of Proteins of Immunological Interest*).

In some embodiments where the fusion protein of the disclosure includes an Fc polypeptide, the Fc polypeptide is mutated or modified. In these embodiments the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments the Fc region is modified at one or both of these positions, for example Lys326Ala and/or Glu333Ala (K326A and E333A) using the Kabat numbering system.

In some embodiments, the human IgG Fc region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15).

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example the fusion protein may contain a modified IgG1 hinge having the sequence of EPKSSDKTHTCPPC (SEQ ID NO: 6), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 7).

In some embodiments, the fusion protein has a modified hinge from IgG4, which is modified to prevent or reduce strand exchange, e.g., Ser228Pro (S228P), having the sequence ESKYGPPCPPC (SEQ ID NO: 8). In some embodiments, the fusion protein contains linker polypeptides. In other embodiments, the fusion protein contains linker and hinge polypeptides.

In some embodiments, the fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the DR5BD is engineered to eliminate recognition by pre-existing antibodies found in humans. In some embodiments, single domain antibodies of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence consists of GQGTLVTVKPGG (SEQ ID NO: 9) or GQGTLVTVEPGG (SEQ ID NO: 10) or modification thereof. In some embodiments, the single domain antibodies of the present disclosure are modified by mutation of position 11 and by changes in carboxy-terminal region.

In some embodiments, the DR5BDs of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 11); GGSGGSGGS, i.e., $(GGS)_3$ (SEQ ID NO: 12); GGSGGSGGSGGS, i.e., $(GGS)_4$ (SEQ ID NO: 13); and GGSGGSGGSGGSGGS, i.e., $(GGS)_5$ (SEQ ID NO: 14).

In some embodiments, the multivalent TNFRSF binding fusion protein is tetravalent. In some embodiments, the tetravalent TNFRSF binding fusion protein has the following structure: VHH-Linker-VHH-Linker-Hinge-Fc, where the VHH is a humanized or fully human VHH sequence that binds at least DR5.

In some embodiments, the multivalent TNFRSF binding fusion protein is tetravalent. In some embodiments, the tetravalent TNFRSF binding fusion protein has the following structure: DR5BD-Linker-DR5BD-Linker-Hinge-Fc, where the DR5BD is a humanized or fully human VHH sequence.

In some embodiments, the multivalent TNFRSF binding fusion protein is hexavalent. In some embodiments, the hexavalent TNFRSF binding fusion protein has the following structure: VHH-Linker-VHH-Linker-VHH-Linker-Hinge-Fc, where the VHH is a humanized or fully human VHH sequence that binds at least DR5.

In some embodiments, the multivalent TNFRSF binding fusion protein is hexavalent. In some embodiments, the hexavalent TNFRSF binding fusion protein has the following structure: DR5BD-Linker-DR5BD-Linker-DR5BD-Linker-Hinge-Fc, where the DR5BD is a humanized or fully human VHH sequence.

In some embodiments, the multivalent fusion proteins targeting DR5 of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 11); GGSGGSGGS, i.e., $(GGS)_3$ (SEQ ID NO: 12); GGSGGSGGSGGS, i.e., $(GGS)_4$ (SEQ ID NO: 13); and GGSGGSGGSGGSGGS, i.e., $(GGS)_5$ (SEQ ID NO: 14).

In some embodiments, the multivalent DR5 binding fusion protein is tetravalent. In some embodiments, the tetravalent DR5 binding fusion protein has the following structure: VHH-Linker-VHH-Linker-Hinge-Fc, where the VHH is a humanized or fully human VHH sequence. In some embodiments, the VHH sequence is selected from the group consisting of SEQ ID NO: 15-91. In some embodiments, the tetravalent DR5 binding fusion protein comprises an amino acid sequence selected from the group consisting of SEQ ID NOs: 92-118.

In some embodiments, the multivalent DR5 binding fusion protein is hexavalent. In some embodiments, the hexavalent DR5 binding fusion protein has the following structure: VHH-Linker-VHH-Linker-VHH-Linker-Hinge-Fc, where the VHH is a humanized or fully human VHH sequence. In some embodiments, the VHH sequence is selected from the group consisting of SEQ ID NO: 15-91. In some embodiments, the hexavalent DR5 binding fusion protein comprises an amino acid sequence selected from the group consisting of SEQ ID NOs: 119-124.

BRIEF DESCRIPTION OF FIGURES

FIGS. 2A, 2B, 2C, 2D, 2E, 2F, and 2G are a series of graphs demonstrating the binding of representative DR5 VHHs or humanized variants thereof to either human DR5 (FIGS. 2A, 2B, 2E, 2F, and 2G) and cyno DR5 (FIGS. 2C and 2D). FIGS. 2A, 2B, 2E, 2F, and 2G demonstrate the binding of some VHHs and humanized VHHs binding to human DR5 as assessed by flow cytometry on DR5 expressing CHO cells. FIGS. 2C and 2D demonstrate the binding of VHHs and humanized VHHs binding to cyno DR5 as assessed by ELISA using recombinant cyno DR5. In FIGS. 2A, B, C, D and E, the DR5 targeting fusion proteins used were bivalent, and formats used were VHH-Fc or humanized (hz) hzVHH-Fc. In FIGS. 2F and 2G, humanized tetravalent (VHH-linker-VHH-Fc) DR5 targeting Fc-fusion proteins were used.

FIG. 3A is a graph demonstrating the enhanced apoptosis inducing capacity of a bivalent DR5 targeting fusion protein when a crosslinking agent is used. FIG. 3B is a graph demonstrating the enhanced apoptosis inducing capacity of a tetravalent DR5 targeting fusion protein compared to a bivalent DR5 targeting fusion protein. FIG. 3C is a graph demonstrating the enhanced apoptosis inducing capacity of a tetravalent and furthermore hexavalent DR5 targeting fusion protein compared to a bivalent DR5 targeting fusion protein and TRAIL.

FIG. 4A is a graph demonstrating the ability of a hexavalent DR5 targeting fusion protein to induce apoptosis of the resistant cell line Panc-1. Colo205 is shown for comparison. H10 DR5 targeting VHH is shown.

FIG. 4B is a graph demonstrating the enhanced sensitivity of Panc-1 to a tetravalent DR5 targeting fusion protein when doxorubicin is added. The DR5 targeting VHH shown is humanized F03 (hzF03), formatted as hzF03-linker-hzF03-Fc.

In FIGS. 6A-6D, the DR5 targeting VHH is a humanized variant of 1F5 (hz1F5) formatted as hzVHH-linker-hzVHH-Fc. In FIGS. 6E-6J, the DR5 targeting VHH is a humanized variant of either 1F2 (hz1F2) or 2C6 (hz2C6) formatted as hzVHH-linker-hzVHH-Fc variants.

FIGS. 8A and 8B are a series of graphs demonstrating the autoantibody recognition-dependent hepatotoxicity of TAS266, but not Tet-hz1F5v5, on HepRG™ the terminally differentiated hepatic cells derived from a hepatic progenitor cell line. In FIG. 8A, apoptosis was monitored using a caspase-3/7-specific fluorogenic substrate with IncuCyte Zoom live cell imager (Essen Biosciences), data shown is at 48 hours. In FIG. 8B, apoptosis was monitored after 48 hours using a CellTiter Glo assay (Promega). IVIG (Gamunex®-C, Grifols) was used an sdAb-directed autoantibody containing antibody pool.

FIGS. 9A, 9B, 9C, and 9D are a series of graphs demonstrating the autoantibody recognition-dependent hepatoxicity of TAS266, but not the tetravalent DR5 targeting fusion proteins of the present disclosure. HepRG™ cells were used as a surrogate for human hepatocytes. IVIG (Gamunex®-C, Grifols) was used an sdAb-directed autoantibody containing antibody pool. FIGS. 9A and 9C depict independent 48 hour assays and demonstrate that TAS266 induces hepatotoxicity when crosslinked by autoantibodies. Moderate hepatotoxicity was observed when a crosslinking anti-human Fc secondary was added to the tetravalent DR5 targeting fusion proteins of the present disclosure, hz1F5, hz1F2 or hz2C6, formatted as hzVHH-linker-hzVHH-Fc. Cell viability was assessed by CellTiter Glo (Promega). FIG. 9D depicts the reduction autoantibody recognition-dependent hepatotoxicity of TAS266 when it is modified at amino acid positions Leu11 and the C-terminal region of each of the four DR5 sdAbs (FIX-TAS266, SEQ ID NO: 126). This data demonstrate that hepatocytoxicity of FIX-266 in the presence of IVIG is reduced to that of TAS266 in the absence of IVIG. HepRG cell viability was assessed by CellTiter Glo (Promega). FIG. 9B depicts the kinetics of autoantibody recognition-dependent hepatotoxicity of TAS266 as well as the secondary antibody crosslinking-dependent hepatotoxicity of Tet-hz1F5v6. Apoptosis was monitored over a 46 hour period using a caspase-3/7-specific fluorogenic substrate with IncuCyte Zoom live cell imager (Essen Biosciences). Tetravalent DR5 targeting fusion proteins of the present disclosure do not induce hepatotoxicity in the presence or absence of sdAb-directed autoantibody containing antibodies.

DETAILED DESCRIPTION

Figure 1:
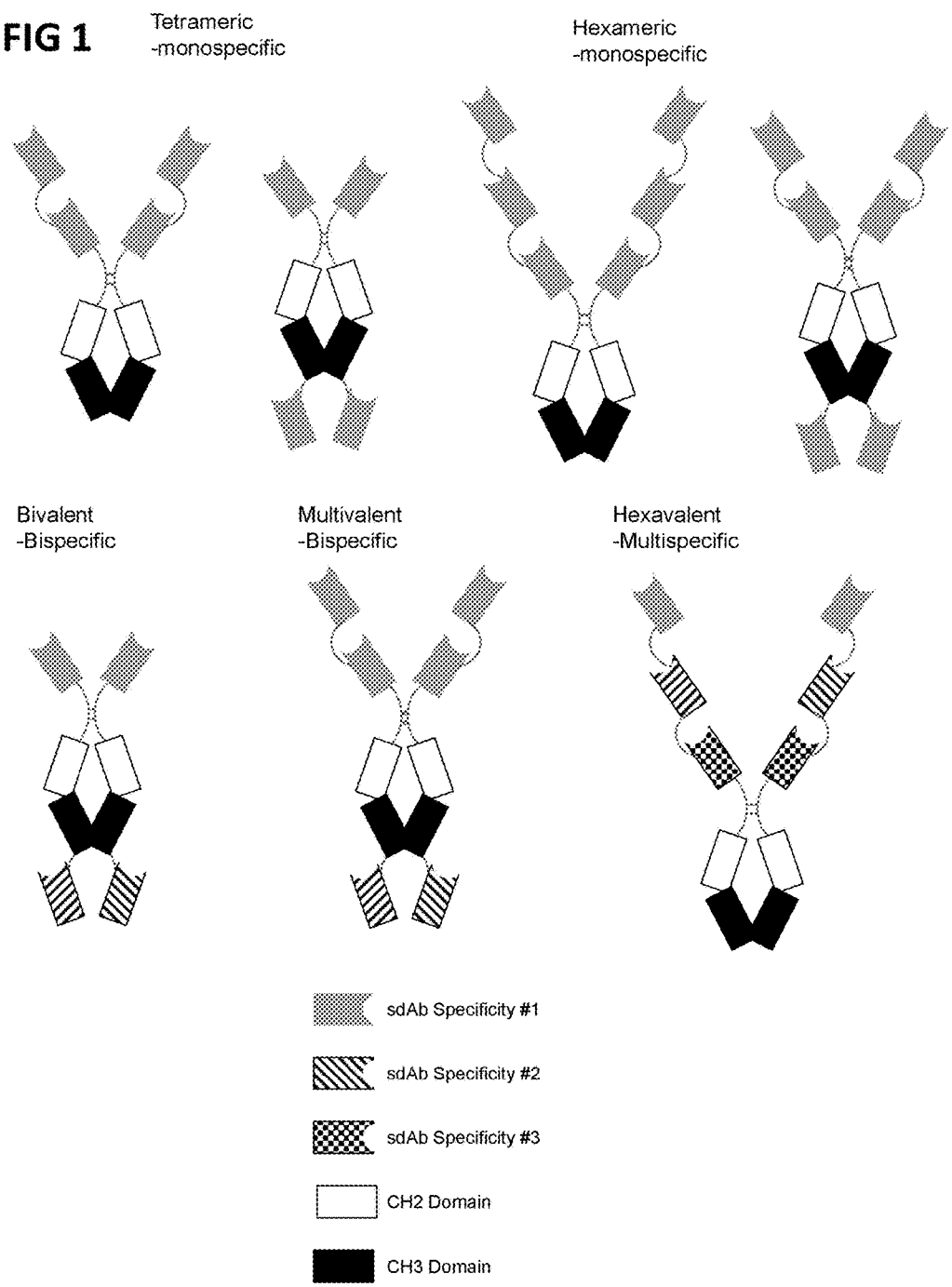
FIG. 1 is schematic of exemplary multivalent and multi-specific fusion proteins of the present disclosure.
Figure 3:
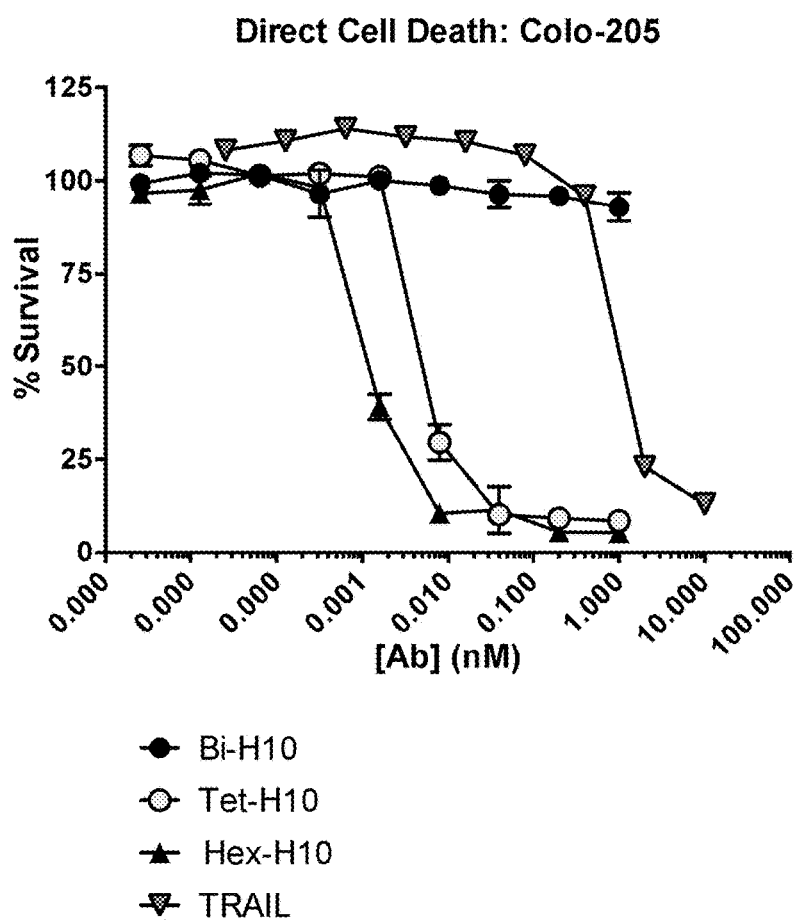
FIGS. 3A, 3B, and 3C are a series of graphs demonstrating the direct apoptosis inducing capacity of DR5 targeting fusion proteins of the present disclosure. In all assays, the Colo205 cells were used and the DR5 targeting VHH was H10 formatted as (A) H10-Fc (bivalent), (B) H10-linker-H10-Fc (tetravalent), or (C) H10-linker-H10-linker-H10-Fc (hexavalent).
Figure 5:
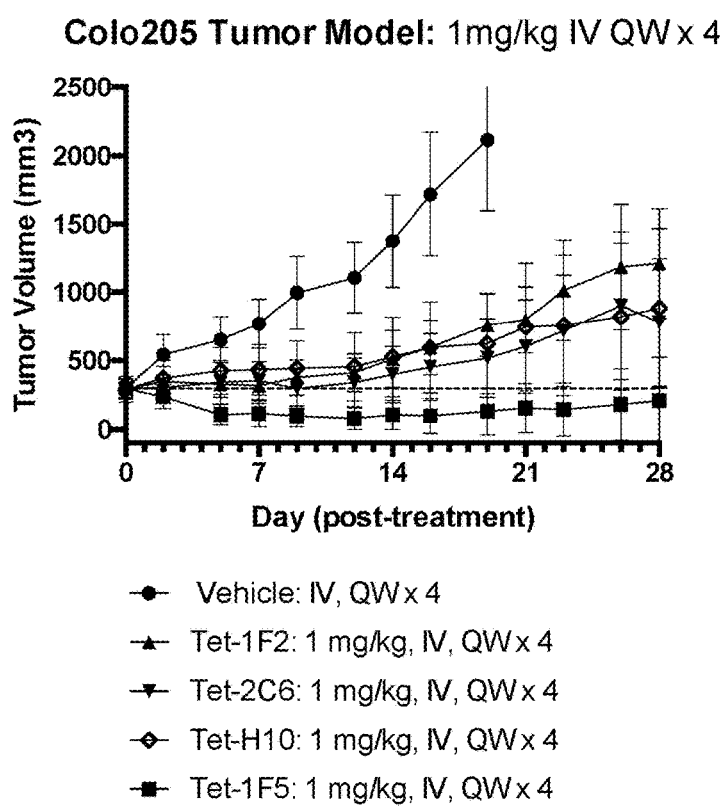
FIG. 5 is a graph demonstrating the anti-tumor activity of tetravalent DR5 targeting fusion proteins of the present disclosure in a murine tumor xenograft model with Colo-205 cells. Fusion proteins were dosed at 1 mg/kg weekly for 4 weeks via IV administration. Dosing began when tumors reached approximately 300 mm³.
Figure 6:
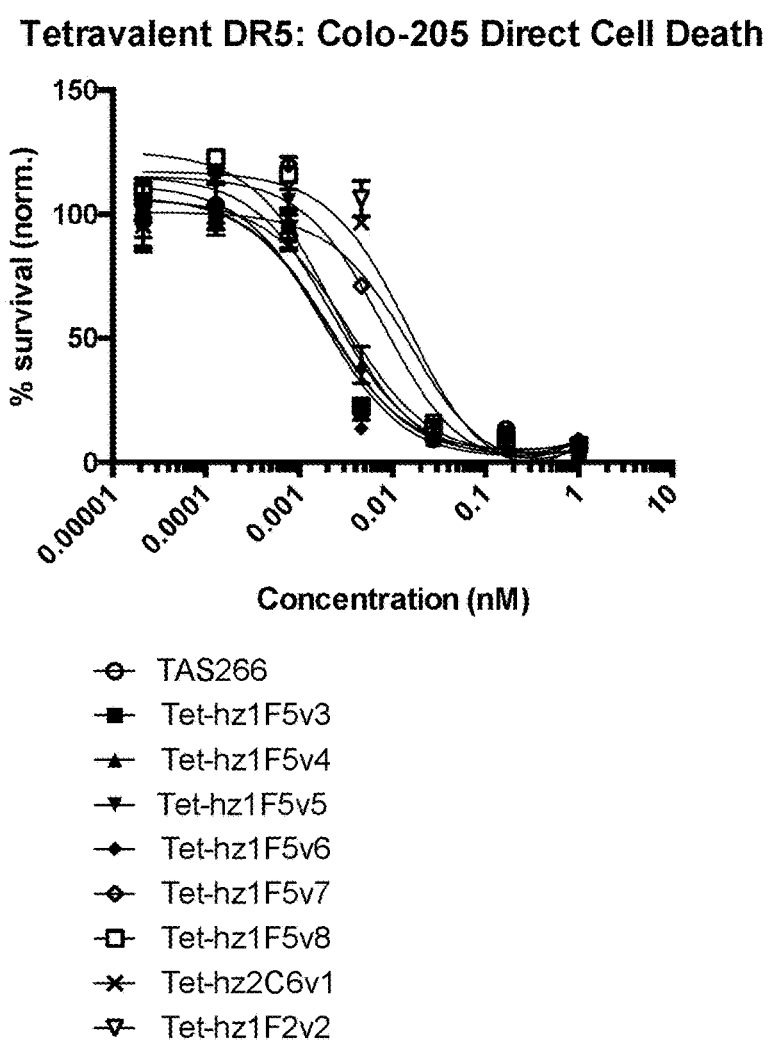
FIGS. 6A, 6B, 6C, 6D, 6E, 6F, 6G, 6H, 6I, and 6J are a series of graphs demonstrating direct cell death inducing capacity of some of the tetravalent DR5 targeting fusion proteins of the present disclosure compared to TAS266 (a tetravalent DR5 nanobody described in PCT Publication No. WO 2011/098520A1) on various cancer cell lines (FIGS. 6A and 6B) Colo-205, Panc-1 (FIGS. 6C and 6J), JL-1 (FIG. 6D), HCT-116 (FIG. 6E), NCI-H28 (FIG. 6F), NCI-H460 (FIG. 6G), HT-29 (FIG. 6H), and MSTO-211H (FIG. 6I).
Figure 6:
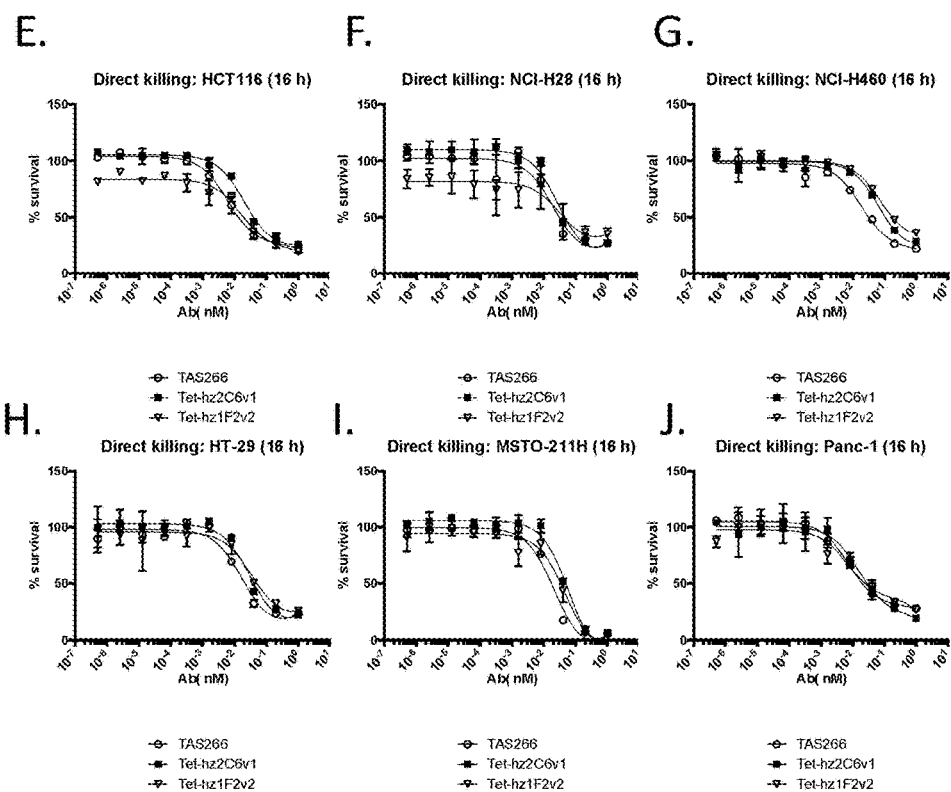
Figure 7:
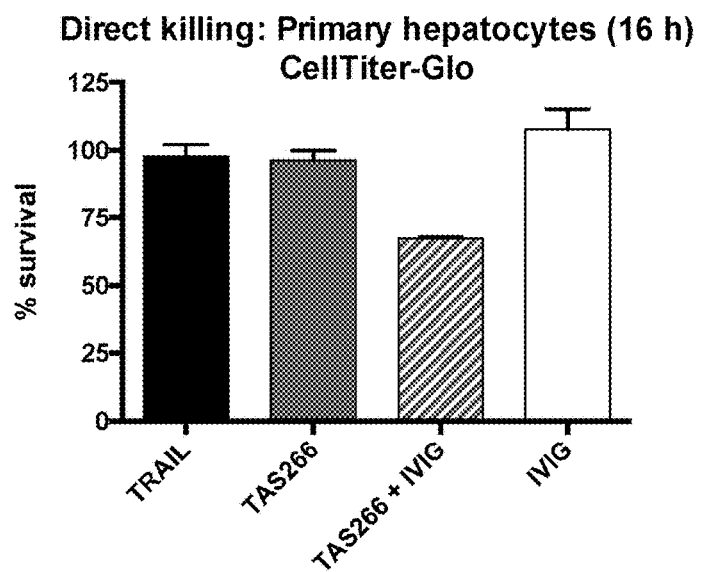
FIG. 7A is a graph demonstrating the differences in autoantibody recognition of TAS266, (a tetravalent DR5 nanobody described in PCT Publication No. WO 2011/098520A1) and humanized tetravalent 1F5 (Tet-hz1F5v5) of present disclosure. This graph depicts the results from the serum of 45 human donors. Autoantibodies containing either a kappa or lambda light chain were detected in separate assays using the respective anti-human Ig Kappa or anti-human Ig Lambda HRP-conjugated secondary antibodies. Data are normalized to positive control of an IgG antibody having either a lambda or kappa light chain, respectively. TAS266 displays significant autoantibody recognition while autoantibody recognition of Tet-hz1F5v5 is reduced to that of IgG control background.
FIG. 7B is a graph that demonstrates that pooled serum from multiple human donors (IVIG, Gamunex®-C, Grifols) contains some IgG antibodies that recognize single domain antibodies (sdAb) including TAS266.
FIG. 7C is a graph that demonstrates that recognition of TAS266 by autoantibodies within IVIG induces apoptosis of primary human hepatocytes.

The disclosure provides molecules that specifically engage death receptor 5 (DR5), a member of the TNF receptor superfamily (TNFRSF). More specifically this disclosure relates to multivalent molecules that bind at least DR5. These multivalent TNFRSF binding fusion proteins comprise two or more TNFRSF binding domains (DR5BDs), where at least one DR5BD binds DR5. These molecules are referred to herein as DR5-targeting molecules.

These DR5-targeting molecules include at least one copy of a single-domain antibody (sdAb) sequence that specifically binds DR5. In some embodiments, the DR5-targeting molecules include two or more copies of a sdAb that specifically binds DR5, for example, three or more, four or more, five or more, or six or more copies of a sdAb that specifically binds DR5.

A single-domain antibody (sdAb) is an antibody fragment consisting of a single monomeric variable antibody domain that is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the disclosure.

A single-domain antibody can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen. (See e.g., Arbabi Ghahroudi, M.; Desmyter, A.; et al. (1997). "Selection and identification of single domain antibody fragments from camel heavy-chain antibodies". FEBS Letters 414 (3): 521-526.)

A different method uses gene libraries from animals that have not been immunized beforehand. Such naïve libraries usually contain only antibodies with low affinity to the desired antigen, making it necessary to apply affinity maturation by random mutagenesis as an additional step. (Saerens, D.; et al. (2008). "Single-domain antibodies as building blocks for novel therapeutics". Current Opinion in Pharmacology 8 (5): 600-608.)

When the most potent clones have been identified, their DNA sequence is optimized, for example to improve their stability towards enzymes. Another goal is humanization to prevent immunological reactions of the human organism against the antibody. Humanization is unproblematic because of the homology between camelid VHH and human VH fragments. (See e.g., Saerens, et al., (2008). "Single-domain antibodies as building blocks for novel therapeutics". Current Opinion in Pharmacology 8 (5): 600-608.) The final step is the translation of the optimized single-domain antibody in *E. coli, Saccharomyces cerevisiae* or other suitable organisms.

Single domain antibody fragments are also derived from conventional antibodies. In some embodiments, single-domain antibodies can be made from common murine or human IgG with four chains. (Holt, L. J.; et al. (2003). "Domain antibodies: proteins for therapy". Trends in Biotechnology 21 (11): 484-490.) The process is similar, comprising gene libraries from immunized or naïve donors and display techniques for identification of the most specific antigens. A problem with this approach is that the binding region of common IgG consists of two domains (VH and VL), which tend to dimerize or aggregate because of their lipophilicity. Monomerization is usually accomplished by replacing lipophilic by hydrophilic amino acids, but often results in a loss of affinity to the antigen. (See e.g., Borrebaeck, C. A. K.; Ohlin, M. (2002). "Antibody evolution beyond Nature". Nature Biotechnology 20 (12): 1189-90.) If affinity can be retained, the single-domain antibodies can likewise be produced in *E. coli, S. cerevisiae* or other organisms.

Monovalent single domain antibodies can be made multivalent via several methods. For example the cDNA encoding a first sdAb can be genetically fused to a linker encoding DNA sequence followed by a second cDNA encoding an sdAb and so forth and so on. Alternatively, the cDNA encoding an sdAb can be fused to cDNA encoding a second protein or fragment thereof that naturally multimerizes or is engineered to multimerize. For example, fusion of an sdAb to an IgG Fc region will dimerize the sdAb. Wherein a tandem sdAb encoding constructed is linked to an Fc encoding construct the resultant fusion protein once expressed will be tetravalent. Wherein a construct that encodes three sdAbs is linked to an Fc encoding construct the resultant fusion protein once expressed will be hexavalent. This disclosure contemplates the use of the additional multimerization domains, including collagen homotrimerization and heterotrimerization domains, leucine zipper domains, p53 tetramerization domains, c-Jun:Fos heterodimeric peptide sequences, cartilage oligomeric matrix protein (COMP48), trimeric adiponectin, trimeric surfactant protein D, and/or synaptic acetylcholinesterase tetramer.

Death Receptor 5 (TRIAL-R2, TNFRSF10B) Targeting

The TNF-related apoptosis-inducing ligand (TRAIL) evolved to play critical roles in mammalian development and host defense by selectively eradicating unwanted, infected and malignant cells from healthy cell populations. On binding the TNF receptor family members DR4 or DR5, TRAIL induces cell death via caspase-dependent apoptosis. DR5 (TNFRSF10B) appears to be the primary receptor on tumor cells that facilitates the observed tumor biased activity of the TRAIL pathway. DR5 is activated by the natural ligand TRAIL, which brings three DR5 receptors within close proximity thereby activating intracellular caspase-8 and initiating activation of other death-inducing caspases, such as caspases-9 and caspases-3. Thus initiation of this cell death pathway requires clustering of DR5 receptors for efficient cell death.

Efforts to clinically exploit the TRAIL pathway for cancer therapy relied upon a recombinant version of the natural ligand TRAIL and antibodies specific for DR5. Antibody agonists targeting DR5 required a crosslinking agent in preclinical in vitro experiments. This was due to the fact the conventional antibodies resulted in clustering of only two DR5 receptors (one per each heavy and light chain). Two DR5 receptors are insufficient to activate the cell death pathway thus the need for a crosslinking agent. Surprisingly in vivo administration of DR5 targeting antibodies in pre-clinical mouse models of human cancers showed significant activity in a wide variety of tumor types. This activity was later shown to be dependent on mouse FcgammaR (FcγR) receptors. Clinical studies in humans failed to reproduce the robust responses seen in these pre-clinical mouse models. The lack of activity in humans is hypothesized to be due to insufficient antibody crosslinking. This may be due to differences in serum IgG, FcgammaR (FcγR) and or TRAIL concentrations between immune compromised mice and human cancer patients.

The present disclosure provides multivalent fusion proteins targeting DR5 that are capable of potently agonizing DR5 signaling mediating direct cell death. The fusion proteins of the present disclosure can be trivalent, tetravalent, pentavalent, or hexavalent. Importantly, the fusion proteins of the present disclosure are capable of eliciting apoptosis of DR5 expressing cells independently of exogenous crosslinking agents.

In some embodiments, the fusion proteins of the present disclosure incorporate a DR5BD that binds DR5. In preferred embodiments, the DR5 binding DR5BD does not bind DR4, decoy R1, decoy R2, Osteopontin, or any other TNFRSF member. In preferred embodiments the DR5 binding DR5BD binds human and cynomolgus monkey DR5. In some embodiments, the DR5 binding DR5BD blocks the interaction of DR5 and its ligand TRAIL. In other embodiments, the DR5 binding DR5BD does not block the interaction of DR5 and its ligand TRAIL. In some embodiments, the fusion protein of the present disclosure incorporates multiple DR5 binding DR5BDs that recognize distinct epitopes on DR5. In some embodiments, the fusion protein of the present disclosure incorporates multiple DR5 binding DR5BDs, wherein some DR5BDs block the DR5-TRAIL interaction and other do not block the DR5-TRAIL interaction. In preferred embodiments, DR5 targeting fusion proteins of the present disclosure induce direct cell death of tumor cells. The DR5 targeting fusion proteins of the present disclosure have utility in treating tumors of both hematologic and solid in nature.

Exemplary DR5 Binding sdAbs

DR5 VHH (llama-derived) and humanized sequences are shown below, and the CDR sequences are shown below each sequence. In some embodiments, the DR5 binding sdAb is fused to an IgG Fc region and in these embodiments the fusion protein is bivalent having two DR5 binding domains per molecule. In some embodiments, two DR5 binding sdAbs (2×) are fused to an IgG Fc region and in these embodiments the fusion protein is tetravalent having four DR5 binding domains per molecule. In some embodiments, three DR5 binding sdAbs (3×) are fused to an IgG Fc region and in these embodiments the fusion protein is hexavalent having six DR5 binding domains per molecule.

1F5
(SEQ ID NO: 15)
QVQLVQSGGGLVQAGDSLRLSCAASGLTFPNYGMGWFRQAPGEEREFLAV
IYWSGGTVFYADSVKGRFTISRDAAKNMVYLQMNSLKSDDTAVYYCAVTI
RGAATQTWKYDYWGRGTQVTVSS (SEQ ID NO: 128)
CDR1: SGLTFPNYGM (SEQ ID NO: 129)
CDR2: VIYWSGGTVF (SEQ ID NO: 130)
CDR3: AVTIRGAATQTWKYDYW hz1F5v1
(SEQ ID NO: 16)
EVQLLESGGGLVQPGGSLRLSCAASGLTFPNYGMSWFRQAPGKGLEFVSA
IYWSGGTVYYADSVKGRFTISRDNSKNTLYLQMNSLRAEDTAVYYCAVTI
RGAATQTWKYDYWGQGTLVTVSS (SEQ ID NO: 128)
CDR1: SGLTFPNYGM (SEQ ID NO: 131)
CDR2: AIYWSGGTVY (SEQ ID NO: 130)
CDR3: AVTIRGAATQTWKYDYW hz1F5v1opt
(SEQ ID NO: 17)
EVQLLESGGGEVQPGGSLRLSCAASGLTFPNYGMSWFRQAPGKGLEFVSA
IYWSGGTVYYAESVKGRFTISRDNAKNTLYLQMSSLRAEDTAVYYCAVTI
RGAATQTWKYDYWGQGTLVTVKPGG (SEQ ID NO: 128)
CDR1: SGLTFPNYGM (SEQ ID NO: 131)
CDR2: AIYWSGGTVY (SEQ ID NO: 130)
CDR3: AVTIRGAATQTWKYDYW hz1F5v1opt1
(SEQ ID NO: 18)
EVQLLESGGGEVQPGGSLRLSCAASGLTFPNYGMSWFRQAPGKGLEFVSA
IYWSGGTVYYAESVKGRFTISRDNAKNTLYLQMSSLRAEDTAVYYCAVTI
RGAATQTWKYDYWGQGTLVTVKP (SEQ ID NO: 128)
CDR1: SGLTFPNYGM (SEQ ID NO: 131)
CDR2: AIYWSGGTVY (SEQ ID NO: 130)
CDR3: AVTIRGAATQTWKYDYW hz1F5v2
(SEQ ID NO: 19)
EVQLLESGGGEVQPGGSLRLSCAASGLTFPNYGMSWFRQAPGKEREFVSA
IYWSGGTVYYAESVKGRFTISRDNAKNTLYLQMSSLRAEDTAVYYCAVTI
RGAATQTWKYDYWGQGTQVTVKP (SEQ ID NO: 128)
CDR1: SGLTFPNYGM (SEQ ID NO: 131)
CDR2: AIYWSGGTVY

```
                                              (SEQ ID NO: 130)
CDR3: AVTIRGAATQTWKYDYW
hz1F5v1DS
                                              (SEQ ID NO: 20)
EVQLLESGGGEVQPGGSLRLSCAASGLTFPNYGMSWFRQAPGKGLEFVCA
IYWSGGTVYYAESVKGRFTCSRDNAKNTLYLQMSSLRAEDTAVYYCAVTI
RGAATQTWKYDYWGQGTLVTVKPGG
                                              (SEQ ID NO: 128)
CDR1: SGLTFPNYGM
                                              (SEQ ID NO: 131)
CDR2: AIYWSGGTVY
                                              (SEQ ID NO: 130)
CDR3: AVTIRGAATQTWKYDYW
hz1F5v3
                                              (SEQ ID NO: 85)
EVQLLESGGGEVQPGGSLRLSCAASGLTFPNYGMGWFRQAPGKEREFVSA
IYWSGGTVFYAESVKGRFTISRDNAKNTVYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 132)
CDR2: AIYWSGGTVF
                                              (SEQ ID NO: 130)
CDR3: AVTIRGAATQTWKYDYW
hz1F5v4
                                              (SEQ ID NO: 86)
EVQLLESGGGEVQPGGSLRLSCAASGLTFPNYGMGWFRQAPGKEREFLAV
IYWSGGTVFYAESVKGRFTISRDNAKNTVYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 129)
CDR2: VIYWSGGTVF
                                              (SEQ ID NO: 130)
CDR3: AVTIRGAATQTWKYDYW
hz1F5v5
                                              (SEQ ID NO: 87)
EVQLLESGGGEVQPGGSLRLSCAASGLTFPNYGMGWFRQAPGKEREFVSA
IYWSGGTVYYAESVKGRFTISRDNAKNTLYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 131)
CDR2: AIYWSGGTVY
                                              (SEQ ID NO: 130)
CDR3: AVTIRGAATQTWKYDYW
hz1F5v6
                                              (SEQ ID NO: 88)
EVQLLESGGGEVQPGGSLRLSCAASGLTFPNYGMGWFRQAPGKEREFLAV
IYWSGGTVYYAESVKGRFTISRDNAKNTLYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 133)
CDR2: VIYWSGGTVY
                                              (SEQ ID NO: 130)
CDR3: AVTIRGAATQTWKYDYW
hz1F5v7
                                              (SEQ ID NO: 89)
EVQLLESGGGEVQPGGSLRLSCAASGLTFPNYGMGWFRQAPGKEREFVSA
IYWSGGTVYYAESVKGRFTISRDNAKNTVYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 131)
CDR2: AIYWSGGTVY
                                              (SEQ ID NO: 130)
CDR3: AVTIRGAATQTWKYDYW
hz1F5v8
                                              (SEQ ID NO: 90)
EVQLLESGGGEVQPGGSLRLSCAASGLTFPNYGMGWFRQAPGKEREFLAV
IYWSGGTVYYAESVKGRFTISRDNAKNTVYLQMSSLRAEDTAVYYCAVTI
RGAATQTWKYDYWGQGTLVTVKP
                                              (SEQ ID NO: 128)
CDR1: SGLTFPNYGM
                                              (SEQ ID NO: 133)
CDR2: VIYWSGGTVY
                                              (SEQ ID NO: 130)
CDR3: AVTIRGAATQTWKYDYW
2C6
                                              (SEQ ID NO: 21)
QVQLVQSGGGLVQAGGSLRLTCTASGRTVSNYAMGWFRQTPGKDREFVAA
LNWSGDTTSYADSVRGRFTISRDNTRNTVYLQMDSLKREDTAVYYCAAAQ
SFRRGGAPYGDNYWGQGTQVTVSS
                                              (SEQ ID NO: 134)
CDR1: SGRTVSNYAM
                                              (SEQ ID NO: 135)
CDR2: ALNWGGDTTS
                                              (SEQ ID NO: 136)
CDR3: AAAQSFRRGGAPYGDNYW
hz2C6v1
                                              (SEQ ID NO: 22)
EVQLLESGGGLVQPGGSLRLSCAASGRTVSNYAMSWFRQAPGKGLEFVSA
LNWGGDTTYYADSVKGRFTISRDNSKNTLYLQMNSLRAEDTAVYYCAAAQ
SFRRGGAPYGDNYWWGQGTLVTVSS
                                              (SEQ ID NO: 134)
CDR1: SGRTVSNYAM
                                              (SEQ ID NO: 137)
CDR2: ALNWGGDTTY
                                              (SEQ ID NO: 136)
CDR3: AAAQSFRRGGAPYGDNYW
hz2C6v1opt
                                              (SEQ ID NO: 23)
EVQLLESGGGEVQPGGSLRLSCAASGRTVSNYAMSWFRQAPGKGLEFVSA
LNWGGDTTYYAESVKGRFTISRDNAKNTLYLQMSSLRAEDTAVYYCAAAQ
SFRRGGAPYGDNYWGQGTLVTVKPGG
```

CDR1: SGRTVSNYAM (SEQ ID NO: 134)

CDR2: ALNWGGDTTY (SEQ ID NO: 137)

CDR3: AAAQSFRRGGAPYGDNYW (SEQ ID NO: 136)

hzC06v2
(SEQ ID NO: 91)
EVQLLESGGGEVQPGGSLRLSCAASGRTVSNYAMGWFRQAPGKDREFVSA
LNWGGDTTYYAESVKGRFTISRDNAKNTLYLQMSSLRAEDTAVYYCAAAQ
SFRRGGAPYGDNYWGQGTLVTVKP

CDR1: SGRTVSNYAM (SEQ ID NO: 134)

CDR2: ALNWGGDTTY (SEQ ID NO: 137)

CDR3: AAAQSFRRGGAPYGDNYW (SEQ ID NO: 136)

C12
(SEQ ID NO: 24)
EVQLVQSGGGLVQAGDSLRLSCAASGRALTGYHMAWFRQAPGKEREFVTY
GIWDRAGAAYADSVKGRFTMSRDNAKNTVYLQMNNLKTEDTAVYYCAASM
AVRTYYSPRSYDSWGQGTQVTVSS

CDR1: SGRALTGYHMAW (SEQ ID NO: 138)

CDR2: YGIWDRAGAA (SEQ ID NO: 139)

CDR3: ASMAVRTYYSPRSYDSW (SEQ ID NO: 140)

hzC12v2
(SEQ ID NO: 25)
EVQLLESGGGLVQPGGSLRLSCAASGRALTGYHMSWFRQAPGKGREFVSY
GIWDRAGAAYADSVKGRFTISRDNSKNTLYLQMNSLRAEDTAVYYCAASM
AVRTYYSPRSYDSWGQGTLVTVSS

CDR1: SGRALTGYHMSW (SEQ ID NO: 141)

CDR2: YGIWDRAGAA (SEQ ID NO: 139)

CDR3: ASMAVRTYYSPRSYDSW (SEQ ID NO: 140)

hzC12v3
(SEQ ID NO: 26)
EVQLLESGGGLVQPGGSLRLSCAASGRALTGYHMSWFRQAPGKGLEFVSY
GIWDRAGAAYADSVKGRFTISRDNSKNTLYLQMNSLRAEDTAVYYCAASM
AVRTYYSPRSYDSWGQGTLVTVSS

CDR1: SGRALTGYHMSW (SEQ ID NO: 141)

CDR2: YGIWDRAGAA (SEQ ID NO: 139)

CDR3: ASMAVRTYYSPRSYDSW (SEQ ID NO: 140)

1F2
(SEQ ID NO: 27)
EVQLVQSGGGLVQAGGSLRLSCAASGSTFSSLDMGWFRQAPGKERAFVAA
ISRSGDNIYYAESVKGRFTISRDNAENTTYLQMNSLKPEDSAVYYCAVDS
QPTYSGGVYYPRYGMDVWGQGTQVTVSS

CDR1: SGSTFSSLDMGW (SEQ ID NO: 142)

CDR2: AISRSGDNIY (SEQ ID NO: 143)

CDR3: AVDSQPTYSGGVYYPRYGMDVW (SEQ ID NO: 144)

hz1F2v2
(SEQ ID NO: 29)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVDS
QPTYSGGVYYPRYGMDVWGQGTLVTVSS

CDR1: SGSTFSSLDMGW (SEQ ID NO: 142)

CDR2: AISRSGDNIY (SEQ ID NO: 143)

CDR3: AVDSQPTYSGGVYYPRYGMDVW (SEQ ID NO: 144)

hz1F2v1
(SEQ ID NO: 30)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDS
QPTYSGGVYYPRYGMDVWGQGTLVTVKP

CDR1: SGSTFSSLDMGW (SEQ ID NO: 142)

CDR2: AISRSGDNIY (SEQ ID NO: 143)

CDR3: AVDSQPTYSGGVYYPRYGMDVW (SEQ ID NO: 144)

hz1F2v2
(SEQ ID NO: 32)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDT
QPTYSGGVYYPRYGMDVWGQGTLVTVKP

CDR1: SGSTFSSLDMGW (SEQ ID NO: 142)

CDR2: AISRSGDNIY (SEQ ID NO: 143)

CDR3: AVDTQPTYSGGVYYPRYGMDVW (SEQ ID NO: 145)

hz1F2v3
(SEQ ID NO: 33)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGMDVWGQGTLVTVKP

CDR1: SGSTFSSLDMGW (SEQ ID NO: 142)

```
CDR2: AISRSGDNIY                  (SEQ ID NO: 143)

CDR3: AVDAQPTYSGGVYYPRYGMDVW      (SEQ ID NO: 146)

hz1F2v4                           (SEQ ID NO: 34)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVES
QPTYSGGVYYPRYGMDVWGQGTLVTVKP

CDR1: SGSTFSSLDMGW                (SEQ ID NO: 142)

CDR2: AISRSGDNIY                  (SEQ ID NO: 143)

CDR3: AVESQPTYSGGVYYPRYGMDVW      (SEQ ID NO: 147)

hz1F2v5                           (SEQ ID NO: 35)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDS
QPTYSGGVYYPRYGYDVWGQGTLVTVKPGG

CDR1: SGSTFSSLDMGW                (SEQ ID NO: 142)

CDR2: AISRSGDNIY                  (SEQ ID NO: 143)

CDR3: AVDSQPTYSGGVYYPRYGYDVW      (SEQ ID NO: 148)

hz1F2v6                           (SEQ ID NO: 36)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDS
QPTYSGGVYYPRYGDDVWGQGTLVTVKPGG

CDR1: SGSTFSSLDMGW                (SEQ ID NO: 142)

CDR2: AISRSGDNIY                  (SEQ ID NO: 143)

CDR3: AVDSQPTYSGGVYYPRYGDDVW      (SEQ ID NO: 148)

hz1F2v7                           (SEQ ID NO: 37)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDS
QPTYSGGVYYPRYGLDVWGQGTLVTVKPGG

CDR1: SGSTFSSLDMGW                (SEQ ID NO: 142)

CDR2: AISRSGDNIY                  (SEQ ID NO: 143)

CDR3: AVDSQPTYSGGVYYPRYGLDVW      (SEQ ID NO: 149)

hz1F2-DS                          (SEQ ID NO: 38)
EVQLLESGGGEVQPGGSLRLSCAASGSTFSSLDMGWFRQAPGKGREFVCA
ISRSGDNIYYAESVKGRFTCSRDNAKNTLYLQMSSLRAEDTAVYYCAVES
QPTYSGGVYYPRYGMDVWGQGTLVTVKPGG

CDR1: SGSTFSSLDMGW                (SEQ ID NO: 142)

CDR2: AISRSGDNIY                  (SEQ ID NO: 143)

CDR3: AVESQPTYSGGVYYPRYGMDVW      (SEQ ID NO: 147)

hz1F2-MA                          (SEQ ID NO: 39)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGADVWGQGTLVTVKPGG

CDR1: SGSTFSSLDMGW                (SEQ ID NO: 142)

CDR2: AISRSGDNIY                  (SEQ ID NO: 143)

CDR3: AVDAQPTYSGGVYYPRYGADVW      (SEQ ID NO: 150)

hz1F2-ME                          (SEQ ID NO: 40)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGEDVWGQGTLVTVKPGG

CDR1: SGSTFSSLDMGW                (SEQ ID NO: 142)

CDR2: AISRSGDNIY                  (SEQ ID NO: 143)

CDR3: AVDAQPTYSGGVYYPRYGEDVW      (SEQ ID NO: 150)

hz1F2-MH                          (SEQ ID NO: 41)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGHDVWGQGTLVTVKPGG

CDR1: SGSTFSSLDMGW                (SEQ ID NO: 142)

CDR2: AISRSGDNIY                  (SEQ ID NO: 143)

CDR3: AVDAQPTYSGGVYYPRYGHDVW      (SEQ ID NO: 151)

hz1F2-MN                          (SEQ ID NO: 42)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGNDVWGQGTLVTVKPGG

CDR1: SGSTFSSLDMGW                (SEQ ID NO: 142)
```

CDR2: AISRSGDNIY (SEQ ID NO: 143)

CDR3: AVDAQPTYSGGVYYPRYGNDVW (SEQ ID NO: 152)

hz1F2-MP (SEQ ID NO: 43)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGPDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGPDVW (SEQ ID NO: 153)

hz1F2-MQ (SEQ ID NO: 44)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGQDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGQDVW (SEQ ID NO: 154)

hz1F2-MR (SEQ ID NO: 45)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGRDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGRDVW (SEQ ID NO: 155)

hz1F2-MS (SEQ ID NO: 46)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGSDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGSDVW (SEQ ID NO: 156)

hz1F2-MT (SEQ ID NO: 47)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGTDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGTDVW (SEQ ID NO: 157)

hz1F2-MV (SEQ ID NO: 48)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVDA
QPTYSGGVYYPRYGVDVWGQGTLVTVKPGG

CDR1: SGSTFSSLDMGW (SEQ ID NO: 142)

CDR2: AISRSGDNIY (SEQ ID NO: 143)

CDR3: AVDAQPTYSGGVYYPRYGVDVW (SEQ ID NO: 158)

B04 (SEQ ID NO: 49)
EVQLVQSGGGLVQAGGSLRLSCAASGRAFSNYALGWFRQAPGKEREFIAA
INWNGENRYGDSVKGRFTISRDNAQNMGYLQMNNLKPEDTAVYRCAAAL
SFRLGGEPYGDAYWGQGTQVTVSS

CDR1: SGRAFSNYALGW (SEQ ID NO: 159)

CDR2: AINWNGENRY (SEQ ID NO: 160)

CDR3: AAALSFRLGGEPYGDAYW (SEQ ID NO: 161)

hzB04v1 (SEQ ID NO: 50)
EVQLLESGGGLVQPGGSLRLSCAASGRAFSNYAMSWFRQAPGKGLEFVSA
INWNGENRYYADSVKGRFTISRDNSKNTLYLQMNSLRAEDTAVYYCAAAL
SFRLGGEPYGDAYWGQGTLVTVSS

CDR1: SGRAFSNYAMSW (SEQ ID NO: 162)

CDR2: AINWNGENRY (SEQ ID NO: 160)

CDR3: AAALSFRLGGEPYGDAYW (SEQ ID NO: 161)

5A04 (SEQ ID NO: 51)
QVQLQESGGGLVQAGGSLRLSCVASGSIFTNNAMGWYRQAPGKQRDLVAQ
ITMGGGITNYAPSMEGRFAISRDNAKSTVYLQMNNLKPEDTAVYYCNAEV
KSADWGAYANYWGQGTQVTVSS

CDR1: SGSIFTNNAM (SEQ ID NO: 163)

```
CDR2: QITMGGGITN                          (SEQ ID NO: 164)

CDR3: NAEVKSADWGAYANYW                    (SEQ ID NO: 165)

hz5A04v1
                                          (SEQ ID NO: 52)
EVQLLESGGGLVQPGGSLRLSCAASGSIFTNNAMSWYRQAPGKGLELVSA
ITMGGGITYYADSVKGRFTISRDNSKNTLYLQMNSLRAEDTAVYYCNAEV
KSADWGAYANYWGQGTLVTVSS

CDR1: SGSIFTNNAM                          (SEQ ID NO: 163)

CDR2: AITMGGGITY                          (SEQ ID NO: 166)

CDR3: NAEVKSADWGAYANYW                    (SEQ ID NO: 165)

hz5A04v2
                                          (SEQ ID NO: 53)
EVQLLESGGGLVQPGGSLRLSCAASGSIFTNNAMSWYRQAPGKGRELVSQ
ITMGGGITYYADSVKGRFTISRDNSKNTLYLQMNSLRAEDTAVYYCNAEV
KSADWGAYANYWGQGTLVTVSS

CDR1: SGSIFTNNAM                          (SEQ ID NO: 163)

CDR2: QITMGGGITY                          (SEQ ID NO: 167)

CDR3: NAEVKSADWGAYANYW                    (SEQ ID NO: 165)

F03
                                          (SEQ ID NO: 54)
QVQLQESGGGLVQAGGSLRLSCAASGRSISNYAMGWFRQAPGKEREFLAA
SVWNNGGNYYADSVKGRFTASRDDAKSTAYLQMSRLRPEDTGIYYCVVAR
TPETPITSARGANYWGQGTQVTVSS

CDR1: SGRSISNYAM                          (SEQ ID NO: 168)

CDR2: ASVWNNGGNY                          (SEQ ID NO: 169)

CDR3: VVARTPETPITSARGANYW                 (SEQ ID NO: 170)

hzF03v2
                                          (SEQ ID NO: 55)
EVQLLESGGGLVQPGGSLRLSCAASGRSISNYAMGWFRQAPGKEREFVSA
SVWNNGGNYYADSVKGRFTISRDNSKNTLYLQMNSLRAEDTAVYYCVVAR
TPETPITSARGANYWGQGTLVTVSS

CDR1: SGRSISNYAM                          (SEQ ID NO: 168)

CDR2: ASVWNNGGNY                          (SEQ ID NO: 169)

CDR3: VVARTPETPITSARGANYW                 (SEQ ID NO: 170)

hzF03v1opt
                                          (SEQ ID NO: 56)
EVQLLESGGGEVQPGGSLRLSCAASGRSISNYAMGWFRQAPGKEREFVSA
SVWNNGGNYYAESVKGRFTISRDNAKNTLYLQMSSLRAEDTAVYYCVVAR
TPETPITSARGANYWGQGTLVTVKPGG

CDR1: SGRSISNYAM                          (SEQ ID NO: 168)

CDR2: ASVWNNGGNY                          (SEQ ID NO: 169)

CDR3: VVARTPETPITSARGANYW                 (SEQ ID NO: 170)

hzF03v2opt
                                          (SEQ ID NO: 57)
EVQLLESGGGEVQPGGSLRLSCAASGRSISNYAMGWFRQAPGKEREFVSA
SVWNNGGNYYAESVKGRFTISRDDAKSTLYLQMSSLRAEDTAVYYCVVAR
TPETPITSARGANYWGQGTLVTVKPGG

CDR1: SGRSISNYAM                          (SEQ ID NO: 168)

CDR2: ASVWNNGGNY                          (SEQ ID NO: 169)

CDR3: VVARTPETPITSARGANYW                 (SEQ ID NO: 170)

hzF03v3opt
                                          (SEQ ID NO: 58)
EVQLLESGGGEVQPGGSLRLSCAASGRSISNYAMGWFRQAPGKEREFVSA
SVWNQGGNYYAESVKGRFTISRDNAKNTLYLQMSSLRAEDTAVYYCVVAR
TPETPITSARGANYWGQGTLVTVKPGG

CDR1: SGRSISNYAM                          (SEQ ID NO: 168)

CDR2: ASVWNQGGNY                          (SEQ ID NO: 171)

CDR3: VVARTPETPITSARGANYW                 (SEQ ID NO: 170)

hzF03v4opt
                                          (SEQ ID NO: 59)
EVQLLESGGGEVQPGGSLRLSCAASGRSISNYAMGWFRQAPGKEREFVSA
SVWNNAGNYYAESVKGRFTISRDNAKNTLYLQMSSLRAEDTAVYYCVVAR
TPETPITSARGANYWGQGTLVTVKPGG

CDR1: SGRSISNYAM                          (SEQ ID NO: 168)

CDR2: ASVWNNAGNY                          (SEQ ID NO: 172)

CDR3: VVARTPETPITSARGANYW                 (SEQ ID NO: 170)

hzF03v5opt
                                          (SEQ ID NO: 60)
EVQLLESGGGEVQPGGSLRLSCAASGRSISNYAMGWFRQAPGKEREFVSA
SVWNQGGNYYAESVKGRFTISRDDAKSTLYLQMSSLRAEDTAVYYCVVAR
TPETPITSARGANYWGQGTLVTVKPGG

CDR1: SGRSISNYAM                          (SEQ ID NO: 168)
```

CDR2: ASVWNQGGNY (SEQ ID NO: 171)

CDR3: VVARTPETPITSARGANYW (SEQ ID NO: 170)

hzF03v6opt
EVQLLESGGGEVQPGGSLRLSCAASGRSISNYAMGWFRQAPGKEREFVSA
SVWNNAGNYYAESVKGRFTISRDDAKSTLYLQMSSLRAEDTAVYYCVVAR
TPETPITSARGANYWGQGTLVTVKPGG (SEQ ID NO: 61)

CDR1: SGRSISNYAM (SEQ ID NO: 168)

CDR2: ASVWNNAGNY (SEQ ID NO: 172)

CDR3: VVARTPETPITSARGANYW (SEQ ID NO: 170)

3B7
QVQLQESGGGSVQAGGSLTLSCAASGRAASDYAVGWFRQAPGKEREFVAA
CNWSGEDTVYAYIVKGRFTISRDNAGNTVSLRMSSLEPEDTAVYYCAAAP
SFSRSVLDGNLSQIDYWGQGTQVTVSS (SEQ ID NO: 62)

CDR1: SGRAASDYAV (SEQ ID NO: 173)

CDR2: ACNWSGEDTV (SEQ ID NO: 174)

CDR3: AAAPSFSRSVLDGNLSQIDYW (SEQ ID NO: 175)

hz3B7v2
EVQLLESGGGLVQPGGSLRLSCAASGRAASDYAMSWFRQAPGKGLEFVSA
INWGGEDTVYADSVKGRFTISRDNSKNTLYLQMNSLRAEDTAVYYCAAAP
SFSRSVLDGNLSQIDYWGQGTLVTVSS (SEQ ID NO: 63)

CDR1: SGRAASDYAM (SEQ ID NO: 176)

CDR2: INWGGEDTV (SEQ ID NO: 177)

CDR3: AAAPSFSRSVLDGNLSQIDYW (SEQ ID NO: 175)

6G01
QVQLVQSGGGLAQAGGSLRLSCVASGRTFTNYAMGWFRQAPGKEREFVAA
INWSGDSTYHADSVKGRFTISRDNAKDSVYLQMTKLKPEDTADYYCASAE
SFSRGGLPYGMNYWGQGTQVTVSS (SEQ ID NO: 64)

CDR1: SGRTFTNYAM (SEQ ID NO: 178)

CDR2: AINWSGDSTY (SEQ ID NO: 179)

CDR3: ASAESFSRGGLPYGMNYW (SEQ ID NO: 180)

hz6G01v1
EVQLLESGGGLVQPGGSLRLSCAASGRTFTNYAMSWFRQAPGKGLEFVSA
INWSGDSTYYADSVKGRFTISRDNSKNTLYLQMNSLRAEDTAVYYCASAE
SFSRGGLPYGMNYWGQGTLVTVSS (SEQ ID NO: 65)

CDR1: SGRTFTNYAM (SEQ ID NO: 178)

CDR2: AINWSGDSTY (SEQ ID NO: 179)

CDR3: ASAESFSRGGLPYGMNYW (SEQ ID NO: 180)

hz6G01v1opt
EVQLLESGGGEVQPGGSLRLSCAASGRTFTNYAMSWFRQAPGKGLEFVSA
INWSGDSTYYAESVKGRFTISRDNAKNTLYLQMSSLRAEDTAVYYCASAE
SFSRGGLPYGMNYWGQGTLVTVKPGG (SEQ ID NO: 66)

CDR1: SGRTFTNYAM (SEQ ID NO: 178)

CDR2: AINWSGDSTY (SEQ ID NO: 179)

CDR3: ASAESFSRGGLPYGMNYW (SEQ ID NO: 180)

H10
QVQLVQSGGGLVQAGGSLTLSCAASVSTFGTSPVGWFRQAPGKEREFVSA
IRWDGVGAYYADSVRGRFKNSKDNAKRTAYLQMNRLKPEDTAVYYCALPR
RGDSELPSTVKEYGYWGQGTQVTVSS (SEQ ID NO: 67)

CDR1: SVSTFGTSPV (SEQ ID NO: 181)

CDR2: AIRWDGVGAY (SEQ ID NO: 182)

CDR3: ALPRRGDSELPSTVKEYGYW (SEQ ID NO: 183)

hzH10v3
EVQLLESGGGEVQPGGSLRLSCAASVSTFGTSPVGWFRQAPGKEREFVSA
IRWEGVGAYYAESVKGRFTISRDNAKNTLYLQMSSLRAEDTAVYYCALPR
RGDSELPSTVKEYGYWGQGTLVTVKP (SEQ ID NO: 68)

CDR1: SVSTFGTSPV (SEQ ID NO: 181)

CDR2: AIRWEGVGAY (SEQ ID NO: 184)

CDR3: ALPRRGDSELPSTVKEYGYW (SEQ ID NO: 183)

hzH10v2
EVQLLESGGGLVQPGGSLRLSCAASVSTFGTSPVGWFRQAPGKEREFVSA
IRWDGVGAYYADSVKGRFTISRDNSKNTLYLQMNSLRAEDTAVYYCALPR
RGDSELPSTVKEYGYWGQGTLVTVSS (SEQ ID NO: 69)

CDR1: SVSTFGTSPV (SEQ ID NO: 181)

CDR2: AIRWDGVGAY (SEQ ID NO: 182)

CDR3: ALPRRGDSELPSTVKEYGYW (SEQ ID NO: 183)

hzH10v1opt
(SEQ ID NO: 70)
EVQLLESGGGEVQPGGSLRLSCAASVSTFGTSPVGWFRQAPGKEREFVSA
IRWDGVGAYYAESVKGRFTISRDNAKNTLYLQMSSLRAEDTAVYYCALPR
RGDSELPSTVKEYGYWGQGTLVTVKPGG

CDR1: SVSTFGTSPV (SEQ ID NO: 181)

CDR2: AIRWDGVGAY (SEQ ID NO: 182)

CDR3: ALPRRGDSELPSTVKEYGYW (SEQ ID NO: 183)

hzH10-DS
(SEQ ID NO: 71)
EVQLLESGGGEVQPGGSLRLSCAASVSTFGTSPVGWFRQAPGKEREFVCA
IRWEGVGAYYAESVKGRFTCSRDNAKNTLYLQMSSLRAEDTAVYYCALPR
RGDSELPSTVKEYGYWGQGTLVTVKPGG

CDR1: SVSTFGTSPV (SEQ ID NO: 181)

CDR2: AIRWEGVGAY (SEQ ID NO: 184)

CDR3: ALPRRGDSELPSTVKEYGYW (SEQ ID NO: 183)

hzH10v4opt
(SEQ ID NO: 72)
EVQLLESGGGEVQPGGSLRLSCAASVSTFGTSPVGWFRQAPGKEREFVSA
IRWDAVGAYYAESVKGRFTISKDNAKRTLYLQMSSLRAEDTAVYYCALPR
RGDSELPSTVKEYGYWGQGTLVTVKPGG

CDR1: SVSTFGTSPV (SEQ ID NO: 181)

CDR2: AIRWDAVGAY (SEQ ID NO: 185)

CDR3: ALPRRGDSELPSTVKEYGYW (SEQ ID NO: 183)

hzH10v5opt
(SEQ ID NO: 73)
EVQLLESGGGEVQPGGSLRLSCAASVSTFGTSPVGWFRQAPGKEREFVSA
IRWDGVGAYYAESVKGRFTISKDNAKRTLYLQMSSLRAEDTAVYYCALPR
RGESELPSTVKEYGYWGQGTLVTVKPGG

CDR1: SVSTFGTSPV (SEQ ID NO: 181)

CDR2: AIRWDGVGAY (SEQ ID NO: 182)

CDR3: ALPRRGESELPSTVKEYGYW (SEQ ID NO: 186)

hzH10v6opt
(SEQ ID NO: 74)
EVQLLESGGGEVQPGGSLRLSCAASVSTFGTSPVGWFRQAPGKEREFVSA
IRWDGVGAYYAESVKGRFTISKDNAKRTLYLQMSSLRAEDTAVYYCALPR
RGDAELPSTVKEYGYWGQGTLVTVKPGG

CDR1: SVSTFGTSPV (SEQ ID NO: 181)

CDR2: AIRWDGVGAY (SEQ ID NO: 182)

CDR3: ALPRRGDAELPSTVKEYGYW (SEQ ID NO: 187)

hzH10v7opt
(SEQ ID NO: 75)
EVQLLESGGGEVQPGGSLRLSCAASVSTFGTSPVGWFRQAPGKEREFVSA
IRWDGVGAYYAESVKGRFTISRDNAKNTLYLQMSSLRAEDTAVYYCALPR
RGDSELPSTVKEYGYWGQGTLVTVKPGG

CDR1: SVSTFGTSPV (SEQ ID NO: 181)

CDR2: AIRWDGVGAY (SEQ ID NO: 182)

CDR3: ALPRRGDSELPSTVKEYGYW (SEQ ID NO: 183)

hzH10v8opt
(SEQ ID NO: 76)
EVQLLESGGGEVQPGGSLRLSCAASVSTFGTSPVGWFRQAPGKEREFVSA
IRWEGVGAYYAESVKGRFTISKDNAKRTLYLQMSSLRAEDTAVYYCALPR
RGESELPSTVKEYGYWGQGTLVTVKPGG

CDR1: SVSTFGTSPV (SEQ ID NO: 181)

CDR2: AIRWEGVGAY (SEQ ID NO: 184)

CDR3: ALPRRGESELPSTVKEYGYW (SEQ ID NO: 186)

hzH10opt
(SEQ ID NO: 77)
EVQLLESGGGEVQPGGSLRLSCAASVSTFGTSPVGWFRQAPGKEREFVSA
IRWEGVGAYYAESVKGRFTISKDNAKRTLYLQMSSLRAEDTAVYYCALPR
RGDAELPSTVKEYGYWGQGTLVTVKPGG

CDR1: SVSTFGTSPV (SEQ ID NO: 181)

CDR2: AIRWEGVGAY (SEQ ID NO: 184)

CDR3: ALPRRGDAELPSTVKEYGYW (SEQ ID NO: 187)

hzH10v10opt
(SEQ ID NO: 78)
EVQLLESGGGEVQPGGSLRLSCAASVSTFGTSPVGWFRQAPGKEREFVSA
IRWDAVGAYYAESVKGRFTISKDNAKRTLYLQMSSLRAEDTAVYYCALPR
RGESELPSTVKEYGYWGQGTLVTVKPGG

CDR1: SVSTFGTSPV (SEQ ID NO: 181)

CDR2: AIRWDAVGAY (SEQ ID NO: 185)

CDR3: ALPRRGESELPSTVKEYGYW (SEQ ID NO: 186)

-continued

H11
(SEQ ID NO: 79)
QLQLQESGGGLVQAGDSLRLSCQVSGRTLSAYLMAWFRQAPNKVREYLGR
IRWNEGDTYYPDSVKGRFTISKDDAKNTVYLRMNSLKPEDTAVYYCAARS
IFNPSDQYVYWGQGTQVTVSS

CDR1: SGRTLSAYLM (SEQ ID NO: 188)

CDR2: RIRWNEGDTY (SEQ ID NO: 189)

CDR3: AARSIFNPSDQYVYW (SEQ ID NO: 190)

hzH11v1
(SEQ ID NO: 80)
EVQLLESGGGLVQPGGSLRLSCAASGRTLSAYLMSWFRQAPGKGLEYVSA
IRWNEGDTYYADSVKGRFTISRDNSKNTLYLQMNSLRAEDTAVYYCAARS
IFNPSDQYVYWGQGTLVTVSS

CDR1: SGRTLSAYLM (SEQ ID NO: 188)

CDR2: AIRWNEGDTY (SEQ ID NO: 28)

CDR3: AARSIFNPSDQYVYW (SEQ ID NO: 190)

hzH11v2
(SEQ ID NO: 81)
EVQLLESGGGLVQPGGSLRLSCAVSGRTLSAYLMSWFRQAPGKGREYVSR
IRWNEGDTYYADSVKGRFTISRDNSKNTLYLQMNSLKAEDTAVYYCAARS
IFNPSDQYVYWGQGTLVTVSS

CDR1: SGRTLSAYLM (SEQ ID NO: 188)

CDR2: RIRWNEGDTY (SEQ ID NO: 189)

CDR3: AARSIFNPSDQYVYW (SEQ ID NO: 190)

1F10
(SEQ ID NO: 82)
EVQLVQSGGGLVQAGGSLRLSCAASGSTFSSLDMGWFRQAPGKERAFVAA
ISRSGDNIYYAESVKGRFTISRDNAENTMYLQMNSLKPEDSAVYYCAVES
QPTYSGGVYYPRYGMDVWGQGTQVTVSS

CDR1: SGSTFSSLDMGW (SEQ ID NO: 142)

CDR2: AISRSGDNIY (SEQ ID NO: 143)

CDR3: AVESQPTYSGGVYYPRYGMDVW (SEQ ID NO: 147)

hz1F10
(SEQ ID NO: 83)
EVQLLESGGGLVQPGGSLRLSCAASGSTFSSLDMSWFRQAPGKGLEFVSA
ISRSGDNIYYADSVKGRFTISRDNSKNTLYLQMNSLRAEDTAVYYCAVES
QPTYSGGVYYPRYGMDVWGQGTLVTVSS

CDR1: SGSTFSSLDMSW (SEQ ID NO: 31)

CDR2: AISRSGDNIY (SEQ ID NO: 143)

CDR3: AVESQPTYSGGVYYPRYGMDVW (SEQ ID NO: 147)

hz1F10v2
(SEQ ID NO: 84)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVES
QPTYSGGVYYPRYGMDVWGQGTLVTVSS

CDR1: SGSTFSSLDMGW (SEQ ID NO: 142)

CDR2: AISRSGDNIY (SEQ ID NO: 143)

CDR3: AVESQPTYSGGVYYPRYGMDVW (SEQ ID NO: 147)

2x_1F5-DS
(SEQ ID NO: 92)
EVQLLESGGGEVQPGGSLRLSCAASGLTFPNYGMSWFRQAPGKGLEFVCA
IYWSGGTVYYAESVKGRFTCSRDNAKNTLYLQMSSLRAEDTAVYYCAVTI
RGAATQTWKYDYWGQGTLVTVKPGGSGGSEVQLLESGGGEVQPGGSLRLS
CAASGLTFPNYGMSWFRQAPGKGLEFVCAIYWSGGTVYYAESVKGRFTCS
RDNAKNTLYLQMSSLRAEDTAVYYCAVTIRGAATQTWKYDYWGQGTLVTV
KPGGGG

2x_1F5
(SEQ ID NO: 93)
EVQLLESGGGEVQPGGSLRLSCAASGLTFPNYGMSWFRQAPGKGLEFVSA
IYWSGGTVYYAESVKGRFTISRDNAKNTLYLQMSSLRAEDTAVYYCAVTI
RGAATQTWKYDYWGQGTLVTVKPGGSGGSEVQLLESGGGEVQPGGSLRLS
CAASGLTFPNYGMSWFRQAPGKGLEFVSAIYWSGGTVYYAESVKGRFTIS
RDNAKNTLYLQMSSLRAEDTAVYYCAVTIRGAATQTWKYDYWGQGTLVTV
KPGGGG

2x_1F5_gs6
(SEQ ID NO: 94)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVDS
QPTYSGGVYYPRYGMDVWGQGTLVTVSGSGGGGSEVQLLESGGGLVQPGG
SLRLSCAASGSTFSSLDMGWFRQAPGKGREFVSAISRSGDNIYYADSVKG
RFTISRDNSKNTLYLQMNSLRAEDTAVYYCAVDSQPTYSGGVYYPRYGMD
VWGQGTLVTVSSAGGGG

2x_1F5_gs12
(SEQ ID NO: 95)
EVQLLESGGGLVQPGGSLRLSCAASGLTFPNYGMSWFRQAPGKGLEFVSA
IYWSGGTVYYADSVKGRFTISRDNSKNTLYLQMNSLRAEDTAVYYCAVTI
RGAATQTWKYDYWGQGTLVTVSSGGGSGGSGGGGSEVQLLESGGGLVQPG
GSLRLSCAASGLTFPNYGMSWFRQAPGKGLEFVSAIYWSGGTVYYADSVK
GRFTISRDNSKNTLYLQMNSLRAEDTAVYYCAVTIRGAATQTWKYDYWGQ
GTLVTVSSAGGGG

2x_1F5_gs15

(SEQ ID NO: 96)
EVQLLESGGGLVQPGGSLRLSCAASGLTFPNYGMSWFRQAPGKGLEFVSA
IYWSGGTVYYADSVKGRFTISRDNSKNTLYLQMNSLRAEDTAVYYCAVTI
RGAATQTWKYDYWGQGTLVTVSSGGGGSGGGGSGGGGSEVQLLESGGGLV
QPGGSLRLSCAASGLTFPNYGMSWFRQAPGKGLEFVSAIYWSGGTVYYAD
SVKGRFTISRDNSKNTLYLQMNSLRAEDTAVYYCAVTIRGAATQTWKYDY
WGQGTLVTVSSAGGGG

2x_hz1F2v2-gs6

(SEQ ID NO: 97)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVDS
QPTYSGGVYYPRYGMDVWGQGTLVTVSGSGGGGSEVQLLESGGGLVQPGG
SLRLSCAASGSTFSSLDMGWFRQAPGKGREFVSAISRSGDNIYYADSVKG
RFTISRDNSKNTLYLQMNSLRAEDTAVYYCAVDSQPTYSGGVYYPRYGMD
VWGQGTLVTVSSAGGGG

2x_hz1F2v2-gs9

(SEQ ID NO: 98)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVDS
QPTYSGGVYYPRYGMDVWGQGTLVTVSSGGGSGGGGSEVQLLESGGGLVQ
PGGSLRLSCAASGSTFSSLDMGWFRQAPGKGREFVSAISRSGDNIYYADS
VKGRFTISRDNSKNTLYLQMNSLRAEDTAVYYCAVDSQPTYSGGVYYPRY
GMDVWGQGTLVTVSSAGGGG

2x_hz1F2v2-gs12

(SEQ ID NO: 99)
EVQLLESGGGLVQPGGSLRLSCAASGSTFSSLDMGWFRQAPGKGREFVSA
ISRSGDNIYYADSVKGRFTISRDNSKNTLYLQMNSLRAEDTAVYYCAVDS
QPTYSGGVYYPRYGMDVWGQGTLVTVSSGGGSGGSGGGGSEVQLLESGGG
LVQPGGSLRLSCAASGSTFSSLDMGWFRQAPGKGREFVSAISRSGDNIYY
ADSVKGRFTISRDNSKNTLYLQMNSLRAEDTAVYYCAVDSQPTYSGGVYY
PRYGMDVWGQGTLVTVSSAGGGG

2x_hz1F2v2-gs15

(SEQ ID NO: 100)
EVQLLESGGGLVQPGGSLRLSCAASGSTFSSLDMSWFRQAPGKGLEFVSA
ISRSGDNIYYADSVKGRFTISRDNSKNTLYLQMNSLRAEDTAVYYCAVDS
QPTYSGGVYYPRYGMDVWGQGTLVTVSSGGGGSGGGGSGGGGSEVQLLES
GGGLVQPGGSLRLSCAASGSTFSSLDMSWFRQAPGKGLEFVSAISRSGDN
IYYADSVKGRFTISRDNSKNTLYLQMNSLRAEDTAVYYCAVDSQPTYSGG
VYYPRYGMDVWGQGTLVTVSSAGGGG

2x_hzB04v1-gs6

(SEQ ID NO: 101)
EVQLLESGGGLVQPGGSLRLSCAASGRAFSNYAMSWFRQAPGKGLEFVSA
INWNGENRYYADSVKGRFTISRDNSKNTLYLQMNSLRAEDTAVYYCAAAL
SFRLGGEPYGDAYWGQGTLVTVSGSGGGGSEVQLLESGGGLVQPGGSLRL
SCAASGRAFSNYAMSWFRQAPGKGLEFVSAINWNGENRYYADSVKGRFTI
SRDNSKNTLYLQMNSLRAEDTAVYYCAAALSFRLGGEPYGDAYWGQGTLV
TVSSAGGGG

2x_hzB04v1-gs12

(SEQ ID NO: 102)
EVQLLESGGGLVQPGGSLRLSCAASGRAFSNYAMSWFRQAPGKGLEFVSA
INWNGENRYYADSVKGRFTISRDNSKNTLYLQMNSLRAEDTAVYYCAAAL
SFRLGGEPYGDAYWGQGTLVTVSSGGGSGGSGGGGSEVQLLESGGGLVQP
GGSLRLSCAASGRAFSNYAMSWFRQAPGKGLEFVSAINWNGENRYYADSV
KGRFTISRDNSKNTLYLQMNSLRAEDTAVYYCAAALSFRLGGEPYGDAYW
GQGTLVTVSSAGGGG

2x_hzB04v1-gs15

(SEQ ID NO: 103)
EVQLLESGGGLVQPGGSLRLSCAASGRAFSNYAMSWFRQAPGKGLEFVSA
INWNGENRYYADSVKGRFTISRDNSKNTLYLQMNSLRAEDTAVYYCAAAL
SFRLGGEPYGDAYWGQGTLVTVSSGGGGSGGGGSGGGGSEVQLLESGGGL
VQPGGSLRLSCAASGRAFSNYAMSWFRQAPGKGLEFVSAINWNGENRYYA
DSVKGRFTISRDNSKNTLYLQMNSLRAEDTAVYYCAAALSFRLGGEPYGD
AYWGQGTLVTVSSAGGGG

2x_F03v2-gs6

(SEQ ID NO: 104)
EVQLLESGGGLVQPGGSLRLSCAASGRSISNYAMGWFRQAPGKEREFVSA
SVWNNGGNYYADSVKGRFTISRDNSKNTLYLQMNSLRAEDTAVYYCVVAR
TPETPITSARGANYWGQGTLVTVSGSGGGGSEVQLLESGGGLVQPGGSLR
LSCAASGRSISNYAMGWFRQAPGKEREFVSASVWNNGGNYYADSVKGRFT
ISRDNSKNTLYLQMNSLRAEDTAVYYCVVARTPETPITSARGANYWGQGT
LVTVSSAGGGG

2x_F03v1-gs6

(SEQ ID NO: 105)
EVQLLESGGGKVQPGGSLRLSCAASGRSISNYAMSWFRQAPGKGLEFVSA
SVWNNGGNYYADSVKGRFTISRDNSKNTLYLQMNSLRAEDTAVYYCVVAR
TPETPITSARGANYWGQGTLVTVSGSGGGGSEVQLLESGGGLVQPGGSLR
LSCAASGRSISNYAMSWFRQAPGKGLEFVSASVWNNGGNYYADSVKGRFT
ISRDNSKNTLYLQMNSLRAEDTAVYYCVVARTPETPITSARGANYWGQGT
LVTVSSAGGGG

2x_F03v1-gs9

(SEQ ID NO: 106)
EVQLLESGGGLVQPGGSLRLSCAASGRSISNYAMSWFRQAPGKGLEFVSA
SVWNNGGNYYADSVKGRFTISRDNSKNTLYLQMNSLRAEDTAVYYCVVAR
TPETPITSARGANYWGQGTLVTVSSGGGSGGGGSEVQLLESGGGLVQPGG
SLRLSCAASGRSISNYAMSWFRQAPGKGLEFVSASVWNNGGNYYADSVKG
RFTISRDNSKNTLYLQMNSLRAEDTAVYYCVVARTPETPITSARGANYWG
QGTLVTVSSAGGGG

2x_F03v1-gs12

(SEQ ID NO: 107)
EVQLLESGGGLVQPGGSLRLSCAASGRSISNYAMSWFRQAPGKGLEFVSA
SVWNNGGNYYADSVKGRFTISRDNSKNTLYLQMNSLRAEDTAVYYCVVAR
TPETPITSARGANYWGQGTLVTVSSGGGSGGSGGGGSEVQLLESGGGLVQ

```
PGGSLRLSCAASGRSISNYAMSWFRQAPGKGLEFVSASVWNNGGNYYADS
VKGRFTISRDNSKNTLYLQMNSLRAEDTAVYYCVVARTPETPITSARGAN
YWGQGTLVTVSSAGGGG
```

2x_F03v1-gs15
(SEQ ID NO: 108)
```
EVQLLESGGGKVQPGGSLRLSCAASGRSISNYAMSWFRQAPGKGLEFVSA
SVWNNGGNYYADSVKGRFTISRDNSKNTLYLQMNSLRAEDTAVYYCVVAR
TPETPITSARGANYWGQGTLVTVSGSGGGGSEVQLLESGGGLVQPGGSLR
LSCAASGRSISNYAMSWFRQAPGKGLEFVSASVWNNGGNYYADSVKGRFT
ISRDNSKNTLYLQMNSLRAEDTAVYYCVVARTPETPITSARGANYWGQGT
LVTVSSAGGGG
```

2x_hzH10v2-gs6
(SEQ ID NO: 109)
```
EVQLLESGGGLVQPGGSLRLSCAASVSTFGTSPVGWFRQAPGKEREFVSA
IRWDGVGAYYADSVKGRFTISRDNSKNTLYLQMNSLRAEDTAVYYCALPR
RGDSELPSTVKEYGYWGQGTLVTVSGSGGGSEVQLLESGGGLVQPGGSL
RLSCAASVSTFGTSPVGWFRQAPGKEREFVSAIRWDGVGAYYADSVKGRF
TISRDNSKNTLYLQMNSLRAEDTAVYYCALPRRGDSELPSTVKEYGYWGQ
GTLVTVSSAGGGG
```

2x_hzH10v2-gs15
(SEQ ID NO: 110)
```
EVQLLESGGGLVQPGGSLRLSCAASVSTFGTSPVGWFRQAPGKEREFVSA
IRWDGVGAYYADSVKGRFTISRDNSKNTLYLQMNSLRAEDTAVYYCALPR
RGDSELPSTVKEYGYWGQGTLVTVSSGGGGSGGGGSGGGGSEVQLLESGG
GLVQPGGSLRLSCAASVSTFGTSPVGWFRQAPGKEREFVSAIRWDGVGAY
YADSVKGRFTISRDNSKNTLYLQMNSLRAEDTAVYYCALPRRGDSELPST
VKEYGYWGQGTLVTVSSAGGGG
```

2x_hz1F5v3_gs6
(SEQ ID NO: 111)
```
EVQLLESGGGEVQPGGSLRLSCAASGLTFPNYGMGWFRQAPGKEREFVSA
IYWSGGTVFYAESVKGRFTISRDNAKNTVYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFVSAIYWSGGTVFYAESVKGRFTIS
RDNAKNTVYLQMSSLRAEDTAVYYCAVTIRGAATQTWKYDYWGQGTLVTV
KPGGGGDKTHTCPPC
```

2x_hz1F5v4_gs6
(SEQ ID NO: 112)
```
EVQLLESGGGEVQPGGSLRLSCAASGLTFPNYGMGWFRQAPGKEREFLAV
IYWSGGTVFYAESVKGRFTISRDNAKNTVYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFLAVIYWSGGTVFYAESVKGRFTIS
RDNAKNTVYLQMSSLRAEDTAVYYCAVTIRGAATQTWKYDYWGQGTLVTV
KPGGGGDKTHTCPPC
```

2x_hz1F5v5_gs6
(SEQ ID NO: 113)
```
EVQLLESGGGEVQPGGSLRLSCAASGLTFPNYGMGWFRQAPGKEREFVSA
IYWSGGTVYYAESVKGRFTISRDNAKNTLYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFVSAIYWSGGTVYYAESVKGRFTIS
RDNAKNTLYLQMSSLRAEDTAVYYCAVTIRGAATQTWKYDYWGQGTLVTV
KPGGGGDKTHTCPPC
```

2x_hz1F5v6_gs6
(SEQ ID NO: 114)
```
EVQLLESGGGEVQPGGSLRLSCAASGLTFPNYGMGWFRQAPGKEREFLAV
IYWSGGTVYYAESVKGRFTISRDNAKNTLYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFLAVIYWSGGTVYYAESVKGRFTIS
RDNAKNTLYLQMSSLRAEDTAVYYCAVTIRGAATQTWKYDYWGQGTLVTV
KPGGGGDKTHTCPPC
```

2x_hz1F5v7_gs6
(SEQ ID NO: 115)
```
EVQLLESGGGEVQPGGSLRLSCAASGLTFPNYGMGWFRQAPGKEREFVSA
IYWSGGTVYYAESVKGRFTISRDNAKNTVYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFVSAIYWSGGTVYYAESVKGRFTIS
RDNAKNTLYLQMSSLRAEDTAVYYCAVTIRGAATQTWKYDYWGQGTLVTV
KPGGGGDKTHTCPPC
```

2x_hz1F5v8_gs6
(SEQ ID NO: 116)
```
EVQLLESGGGEVQPGGSLRLSCAASGLTFPNYGMGWFRQAPGKEREFLAV
IYWSGGTVYYAESVKGRFTISRDNAKNTVYLQMSSLRAEDTAVYYCAVTI
RGAATQTWKYDYWGQGTLVTVKPGGSGGSEVQLLESGGGEVQPGGSLRLS
CAASGLTFPNYGMGWFRQAPGKEREFLAVIYWSGGTVYYAESVKGRFTIS
RDNAKNTVYLQMSSLRAEDTAVYYCAVTIRGAATQTWKYDYWGQGTLVTV
KPGGGGDKTHTCPPC
```

2x_hzC06v2_gs6
(SEQ ID NO: 117)
```
EVQLLESGGGEVQPGGSLRLSCAASGRTVSNYAMGWFRQAPGKDREFVSA
LNWGGDTTYYAESVKGRFTISRDNAKNTLYLQMSSLRAEDTAVYYCAAAQ
SFRRGGAPYGDNYWGQGTLVTVKPGGSGGSEVQLLESGGGEVQPGGSLRL
SCAASGRTVSNYAMGWFRQAPGKDREFVSALNWGGDTTYYAESVKGRFTI
SRDNAKNTLYLQMSSLRAEDTAVYYCAAAQSFRRGGAPYGDNYWGQGTLV
TVKPGGGGDKTHTCPPC
```

2x_hzC06v2_gs9
(SEQ ID NO: 118)
```
EVQLLESGGGEVQPGGSLRLSCAASGRTVSNYAMGWFRQAPGKDREFVSA
LNWGGDTTYYAESVKGRFTISRDNAKNTLYLQMSSLRAEDTAVYYCAAAQ
SFRRGGAPYGDNYWGQGTLVTVKPGGSGGSGGSEVQLLESGGGEVQPGGS
LRLSCAASGRTVSNYAMGWFRQAPGKDREFVSALNWGGDTTYYAESVKGR
```

FTISRDNAKNTLYLQMSSLRAEDTAVYYCAAAQSFRRGGAPYGDNYWGQG
TLVTVKPGGGGDKTHTCPPC

3x_hzF03
(SEQ ID NO: 119)
EVQLLESGGGLVQPGGSLRLSCAASGRSISNYAMSWFRQAPGKGLEFVSA
SVWNNGGNYYADSVKGRFTISRDNSKNTLYLQMNSLRAEDTAVYYCVVAR
TPETPITSARGANYWGQGTLVTVSSGGGGSGGGGSGGGGSEVQLLESGGG
LVQPGGSLRLSCAASGRSISNYAMSWFRQAPGKGLEFVSASVWNNGGNYY
ADSVKGRFTISRDNSKNTLYLQMNSLRAEDTAVYYCVVARTPETPITSAR
GANYWGQGTLVTVSSGGGGSGGGGSGGGGSEVQLLESGGGLVQPGGSLRL
SCAASGRSISNYAMSWFRQAPGKGLEFVSASVWNNGGNYYADSVKGRFTI
SRDNSKNTLYLQMNSLRAEDTAVYYCVVARTPETPITSARGANYWGQGTL
VTVSSAGGGG

3x_H10-DS
(SEQ ID NO: 120)
EVQLLESGGGEVQPGGSLRLSCAASVSTFGTSPVGWFRQAPGKEREFVCA
IRWEGVGAYYAESVKGRFTCSRDNAKNTLYLQMSSLRAEDTAVYYCALPR
RGDSELPSTVKEYGYWGQGTLVTVKPGGSGGSEVQLLESGGGEVQPGGSL
RLSCAASVSTFGTSPVGWFRQAPGKEREFVCAIRWEGVGAYYAESVKGRF
TCSRDNAKNTLYLQMSSLRAEDTAVYYCALPRRGDSELPSTVKEYGYWGQ
GTLVTVKPGGSGGSEVQLLESGGGEVQPGGSLRLSCAASVSTFGTSPVGW
FRQAPGKEREFVCAIRWEGVGAYYAESVKGRFTCSRDNAKNTLYLQMSSL
RAEDTAVYYCALPRRGDSELPSTVKEYGYWGQGTLVTVKPGGGG

3x_H10
(SEQ ID NO: 121)
EVQLLESGGGEVQPGGSLRLSCAASVSTFGTSPVGWFRQAPGKEREFVSA
IRWEGVGAYYAESVKGRFTISRDNAKNTLYLQMSSLRAEDTAVYYCALPR
RGDSELPSTVKEYGYWGQGTLVTVKPGGSGGSEVQLLESGGGEVQPGGSL
RLSCAASVSTFGTSPVGWFRQAPGKEREFVSAIRWEGVGAYYAESVKGRF
TISRDNAKNTLYLQMSSLRAEDTAVYYCALPRRGDSELPSTVKEYGYWGQ
GTLVTVKPGGSGGSEVQLLESGGGEVQPGGSLRLSCAASVSTFGTSPVGW
FRQAPGKEREFVSAIRWEGVGAYYAESVKGRFTISRDNAKNTLYLQMSSL
RAEDTAVYYCALPRRGDSELPSTVKEYGYWGQGTLVTVKPGGGG

3x_1F2-DS
(SEQ ID NO: 122)
EVQLLESGGGEVQPGGSLRLSCAASGSTFSSLDMGWFRQAPGKGREFVCA
ISRSGDNIYYAESVKGRFTCSRDNAKNTLYLQMSSLRAEDTAVYYCAVES
QPTYSGGVYYPRYGMDVWGQGTLVTVKPGGSGGSEVQLLESGGGEVQPGG
SLRLSCAASGSTFSSLDMGWFRQAPGKGREFVCAISRSGDNIYYAESVKG
RFTCSRDNAKNTLYLQMSSLRAEDTAVYYCAVESQPTYSGGVYYPRYGMD
VWGQGTLVTVKPGGSGGSEVQLLESGGGEVQPGGSLRLSCAASGSTFSSL
DMGWFRQAPGKGREFVCAISRSGDNIYYAESVKGRFTCSRDNAKNTLYLQ
MSSLRAEDTAVYYCAVESQPTYSGGVYYPRYGMDVWGQGTLVTVKPGGGG

3x_1F2
(SEQ ID NO: 123)
EVQLLESGGGEVQPGGSLRLSCAASGSTFSSLDMGWFRQAPGKGREFVSA
ISRSGDNIYYAESVKGRFTISRDNAKNTLYLQMSSLRAEDTAVYYCAVES
QPTYSGGVYYPRYGMDVWGQGTLVTVKPGGSGGSEVQLLESGGGEVQPGG
SLRLSCAASGSTFSSLDMGWFRQAPGKGREFVSAISRSGDNIYYAESVKG
RFTISRDNAKNTLYLQMSSLRAEDTAVYYCAVESQPTYSGGVYYPRYGMD
VWGQGTLVTVKPGGSGGSEVQLLESGGGEVQPGGSLRLSCAASGSTFSSL
DMGWFRQAPGKGREFVSAISRSGDNIYYAESVKGRFTISRDNAKNTLYLQ
MSSLRAEDTAVYYCAVESQPTYSGGVYYPRYGMDVWGQGTLVTVKPGGGG

3x_H10-gs15
(SEQ ID NO: 124)
QVQLVQSGGGLVQAGGSLTLSCAASVSTFGTSPVGWFRQAPGKEREFVSA
IRWDGVGAYYADSVRGRFKNSKDNAKRTAYLQMNRLKPEDTAVYYCALPR
RGDSELPSTVKEYGYWGQGTQVTVSSGGGGSGGGGSGGGGSQVQLVQSGG
GLVQAGGSLTLSCAASVSTFGTSPVGWFRQAPGKEREFVSAIRWDGVGAY
YADSVRGRFKNSKDNAKRTAYLQMNRLKPEDTAVYYCALPRRGDSELPST
VKEYGYWGQGTQVTVSSGGGGSGGGGSGGGGSQVQLVQSGGGLVQAGGSL
TLSCAASVSTFGTSPVGWFRQAPGKEREFVSAIRWDGVGAYYADSVRGRF
KNSKDNAKRTAYLQMNRLKPEDTAVYYCALPRRGDSELPSTVKEYGYWGQ
GTQVTVSSAGGGG

TAS266/11H6_hu_tetramer
(SEQ ID NO: 125)
EVQLLESGGGLVQPGGSLRLSCAASGTFDKINNMGWYRQAPGKQRDLVAQ
ITPGGITDYADSVKGRFTISRDNSKNTLYLQMNSLRPEDTAVYYCNAEIL
KRAYIDVYVNYWGQGTLVTVSSGGGGSGGGGSGGGGSGGGGSGGGGSGGG
GSGGGGSEVQLLESGGGLVQPGGSLRLSCAASGTFDKINNMGWYRQAPGK
QRDLVAQITPGGITDYADSVKGRFTISRDNSKNTLYLQMNSLRPEDTAVY
YCNAEILKRAYIDVYVNYWGQGTLVTVSSGGGGSGGGGSGGGGSGGGGSG
GGGSGGGGSGGGGSEVQLLESGGGLVQPGGSLRLSCAASGTFDKINNMGW
YRQAPGKQRDLVAQITPGGITDYADSVKGRFTISRDNSKNTLYLQMNSLR
PEDTAVYYCNAEILKRAYIDVYVNYWGQGTLVTVSSGGGGSGGGGSGGGG
SGGGGSGGGGSGGGGSGGGGSEVQLLESGGGLVQPGGSLRLSCAASGTFD
KINNMGWYRQAPGKQRDLVAQITPGGITDYADSVKGRFTISRDNSKNTLY
LQMNSLRPEDTAVYYCNAEILKRAYIDVYVNYWGQGTLVTVSS FIX-TAS266
(SEQ ID NO: 126)
EVQLLESGGGEVQPGGSLRLSCAASGTFDKINNMGWYRQAPGKQRDLVAQ
ITPGGITDYADSVKGRFTISRDNSKNTLYLQMNSLRPEDTAVYYCNAEIL
KRAYIDVYVNYWGQGTLVTVKPGGGSGGGGSGGGGSGGGGSGGGGSGGGG
GSGGGGSEVQLLESGGGEVQPGGSLRLSCAASGTFDKINNMGWYRQAPGK
QRDLVAQITPGGITDYADSVKGRFTISRDNSKNTLYLQMNSLRPEDTAVY
YCNAEILKRAYIDVYVNYWGQGTLVTVKPGGGSGGGGSGGGGSGGGGSG
GGGSGGGGSGGGGSEVQLLESGGGEVQPGGSLRLSCAASGTFDKINNMGW -continued

```
YRQAPGKQRDLVAQITPGGITDYADSVKGRFTISRDNSKNTLYLQMNSLR

PEDTAVYYCNAEILKRAYIDVYVNYWGQGTLVTVKPGGGGSGGGGSGGGG

SGGGGSGGGGSGGGGSGGGGSEVQLLESGGGEVQPGGSLRLSCAASGTFD

KINNMGWYRQAPGKQRDLVAQITPGGITDYADSVKGRFTISRDNSKNTLY

LQMNSLRPEDTAVYYCNAEILKRAYIDVYVNYWGQGTLVTVKPGG
```

The DR5-targeting proteins described herein are useful in a variety of therapeutic, diagnostic and prophylactic indications. For example, the DR5-targeting proteins are useful in treating a variety of diseases and disorders in a subject. In some embodiments, the DR5-targeting proteins are useful in treating, alleviating a symptom of, ameliorating and/or delaying the progression of a disease or disorder in a subject suffering from or identified as being at risk for an inflammatory disease or disorder. In some embodiments, the DR5-targeting proteins are useful in treating, alleviating a symptom of, ameliorating and/or delaying the progression of a cancer or other neoplastic condition. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, mesothelioma, leukemia, lymphoma, myeloma, and virus-related cancer. In certain embodiments, the cancer is a metastatic cancer, refractory cancer, or recurrent cancer. In some embodiments, the DR5-targeting proteins are useful in reducing or depleting the number of T regulatory cells in a tumor of a subject in need thereof. In some embodiments, the DR5-targeting proteins are useful in stimulating an immune response in a subject. In some embodiments, the DR5-targeting proteins are useful in treating, alleviating a symptom of, ameliorating and/or delaying the progression of an autoimmune disease or disorder. In some embodiments, the DR5-targeting proteins are useful in treating, alleviating a symptom of, ameliorating and/or delaying the progression of viral, bacterial and parasitic infections.

Therapeutic formulations of the disclosure, which include a DR5-targeting molecule of the disclosure, are used to treat or alleviate a symptom associated with a disease or disorder associated with aberrant activity and/or expression of DR5 in a subject. A therapeutic regimen is carried out by identifying a subject, e.g., a human patient suffering from (or at risk of developing) a disease or disorder associated with aberrant activity and/or expression of DR5 using standard methods, including any of a variety of clinical and/or laboratory procedures. The term patient includes human and veterinary subjects. The term subject includes humans and other mammals.

Efficaciousness of treatment is determined in association with any known method for diagnosing or treating the particular disease or disorder associated with aberrant activity and/or expression of DR5. Alleviation of one or more symptoms of the disease or disorder associated with aberrant activity and/or expression of DR5 indicates that the DR5-targeting molecule confers a clinical benefit.

Therapeutic uses of the DR5-targeting molecules of the disclosure can also include the administration of one or more additional agents.

In some embodiments, the DR5-targeting molecule is administered during and/or after treatment in combination with one or more additional agents. In some embodiments, the DR5-targeting molecule and the additional agent are formulated into a single therapeutic composition, and the DR5-targeting molecule and additional agent are administered simultaneously. Alternatively, the DR5-targeting molecule and additional agent are separate from each other, e.g., each is formulated into a separate therapeutic composition, and the DR5-targeting molecule and the additional agent are administered simultaneously, or the DR5-targeting molecule and the additional agent are administered at different times during a treatment regimen. For example, the DR5-targeting molecule is administered prior to the administration of the additional agent, the DR5-targeting molecule is administered subsequent to the administration of the additional agent, or the DR5-targeting molecule and the additional agent are administered in an alternating fashion. As described herein, the DR5-targeting molecule and additional agent are administered in single doses or in multiple doses.

In some embodiments, the DR5-targeting molecule and the additional agent(s) are administered simultaneously. For example, the DR5-targeting molecule and the additional agent(s) can be formulated in a single composition or administered as two or more separate compositions. In some embodiments, the DR5-targeting molecule and the additional agent(s) are administered sequentially, or the DR5-targeting molecule and the additional agent are administered at different times during a treatment regimen.

Methods for the screening of DR5 targeting molecules that possess the desired specificity include, but are not limited to, enzyme linked immunosorbent assay (ELISA), enzymatic assays, flow cytometry, and other immunologically mediated techniques known within the art.

The disclosure further provides nucleic acid sequences and particularly DNA sequences that encode the present fusion proteins. Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate the methods of preparing the DR5-targeting molecules described herein and to obtain significant quantities of the fusion protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used.

The disclosure also provides methods of producing a DR5-targeting molecule by culturing a cell under conditions that lead to expression of the polypeptide, wherein the cell comprises an isolated nucleic acid molecule encoding a DR5-targeting molecule described herein, and/or vectors that include these isolated nucleic acid sequences. The disclosure provides methods of producing a DR5-targeting molecule by culturing a cell under conditions that lead to expression of the DR5-targeting molecule, wherein the cell comprises an isolated nucleic acid molecule encoding a DR5-targeting molecule described herein, and/or vectors that include these isolated nucleic acid sequences.

The fusion proteins of the disclosure (also referred to herein as "active compounds"), and derivatives, fragments, analogs and homologs thereof, can be incorporated into pharmaceutical compositions suitable for administration. Such compositions typically comprise the fusion protein and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. The term patient includes human and veterinary subjects.

As utilized in accordance with the present disclosure, the following terms, unless otherwise indicated, shall be understood to have the following meanings:

As used herein, the terms "targeting fusion protein" and "antibody" can be synonyms. As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, dAb (domain antibody), single chain, Fab, Fab, and F(ab')$_2$ fragments, F$_v$, scFvs, an Fab expression library, and single domain antibody (sdAb) fragments, for example V$_H$H, V$_{NAR}$, engineered V$_H$ or V$_K$.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses (also known as isotypes) as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The single domain antibody (sdAb) fragments portions of the fusion proteins of the present disclosure are referred to interchangeably herein as targeting polypeptides herein.

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding" and "immunological binding properties" and "specific binding" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to an antigen, when the equilibrium binding constant ($K_d$) is ≤1 µM, preferably ≤100 nM, more preferably ≤10 nM, and most preferably ≤100 pM to about 1 pM, as measured by assays such as radioligand binding assays, surface plasmon resonance (SPR), flow cytometry binding assay, or similar assays known to those skilled in the art.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to DR5, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p.392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, and/or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, the terms "treat," "treating," "treatment," and the like refer to reducing and/or ameliorating a disorder and/or symptoms associated therewith. By "alleviate" and/or "alleviating" is meant decrease, suppress, attenuate, diminish, arrest, and/or stabilize the development or progression of a disease such as, for example, a cancer. It will be appreciated that, although not precluded, treating a disorder or condition does not require that the disorder, condition or symptoms associated therewith be completely eliminated.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "subject" is meant a mammal, including, but not limited to, a human or non-human mammal, such as a bovine, equine, canine, rodent, ovine, primate, camelid, or feline.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The invention will be further described in the following examples, which do not limit the scope of the disclosure described in the claims.

EXAMPLES

Example 1: Binding Assays

Binding of DR5-targeting fusion proteins was assessed by flow cytometry, using a CHO cell line stably transfected with cDNA encoding full length DR5 or cancer cell lines that endogenously express DR5. A titration series of the fusion protein was incubated with the DR5-expressing cell lines (approx. $2.5-5\times10^4$ cells/well) for 30 minutes at 4° C. in FACS Buffer (PBS 1% BSA, 0.1% $NaN_3$ pH 7.4) in 96 well plates. Following 3 wash steps in FACS buffer, an APC-conjugated anti-human Fcγ specific secondary antibody (Jackson ImmunoResearch) was added and incubated for 30 minutes at 4° C. Following three additional wash steps in FACS buffer bound antibody was detected via flow cytometry (IQue Intellicyte). Binding of fusion proteins to cynomologus monkey DR5 (cynoDR5) was determined by ELISA wherein a recombinant protein corresponding to the extracellular domain (ECD) of cynoDR5 fused to a murine Fc region (mFc) was immobilized on Medisorp 96 well plates (Nunc). Following sufficient blocking and washing steps, bound fusion proteins were detected using an HRP-conjugated anti-human Fcγ specific secondary antibody (Jackson ImmunoResearch) and TMB reagent and absorbance read at $A_{650nm}$.

Example 2: Apoptosis Assays

Antibody-mediated direct killing of cells was determined by measuring the amount of ATP present following a 16-48 h treatment period using CellTiter-Glo® (Promega G7572). Cancer cells were seeded at $1.5-3\times10^4$ cells/well at $7\times10^4$ cells/well in 96-well flat-bottom tissue culture treated plates. An alternative method for measuring cell death is to fluorescently stain cells using IncuCyte™ Caspase-3/7 Reagent for Apoptosis (Essen BioScience 4440) during antibody treatment and quantify fluorescent cells using an IncuCyte® ZOOM System some embodiments, the fusion protein contains a polypeptide. Cell lines used include Colo-205 (ATCC® CCL-222™), Panc-1 (ATCC® CRL-1469™), HCT-116 (ATCC® CCL-247™), JL-1 (DSMZ ACC 596), NCI-H28 (ATCC® CRL-5820™), NCI-H460 (ATCC® HTB-177™), HT-29 (ATCC® HTB-38™). MSTO-211H (ATCC® CRL-2081™). In some experiments, an anti-human IgG Fcγ-specific secondary (Jackson ImmunoResearch) antibody was used to crosslink and further cluster the DR5 targeting fusion proteins of the present disclosure. In other experiments 6 µM doxycycline was used to sensitize cells to DR5-mediated apoptosis.

Example 3: Pre-Existing Autoantibodies Recognizing sdAbs

Pre-existing human anti-VH (HAVH) in human plasma or IVIG (purified IgG from pooled human plasma, trade name Gamunex®-C) were measured by ELISA. Test articles (TAS266, fusion proteins or therapeutic antibodies) were coated on an ELISA plate in PBS, the plate was blocked by 3% BSA in PBS, then human plasma or IVIG (as a source of naturally occurring HAVH) was diluted in PBS+0.1% polysorbate-20 (PBST) and allowed to bind to the plate. After washing the plate with PBST, bound plasma antibodies (HAVH) were detected by anti-light chain secondary antibodies (anti-human IgKappa or anti-IgLambda) conjugated to HRP, and developed with TMB substrate. This strategy of detecting HAVH by anti-light chain secondary antibody is compatible with test articles lacking light chains, which includes TAS266 as well as the described multivalent sdAbs, and facilitates detection of HAVH of any isotype. Control therapeutic antibodies with kappa or lambda light chains were coated and used as 100% binding reference data points to normalize the data to, and served as control IgG for the opposite secondary antibody.

Example 4: Hepatotoxicity Assays

Primary human hepatocytes or HepRG™ (Thermo Fisher Scientific) the terminally differentiated hepatic cells derived from a hepatic progenitor cell line were used to assess DR5 agonist mediated apoptosis of hepatocytes. All assays were conducted in a similar manner to the apoptosis assays using cancer cell lines (Example 2). Pooled human IgG from multiple donors, IVIG (Gamunex®-C, Grifols), was used as source of natural sdAb-directed autoantibodies, also termed human anti-VH (HAVH) autoantibodies. In some experiments, IVIG was titrated or used at a fixed concentration. In some assays, FIX-TAS266, which is a modified version of TAS266 that is engineered to avoid recognition by HAVH autoantibodies, was included. FIX-2TAS66 includes modifications a Leu11 and the C-terminal region of each of the four DR5 sdAbs of TAS266.

What is claimed is:

1. An isolated polypeptide that binds death receptor 5 (DR5) and comprises a plurality of DR5 binding domains (DR5BDs), wherein each DR5BD is a VHH comprising a CDR1 comprising the amino acid sequence of SEQ ID NO: 128, a CDR2 comprising the amino acid sequence of SEQ ID NO: 131, and a CDR3 comprising the amino acid sequence of SEQ ID NO: 130, and wherein adjacent DR5BDs are operably linked by an amino acid linker.

2. The isolated polypeptide of claim 1, wherein the plurality of DR5BDs is two DR5BDs.

3. The isolated polypeptide of claim 1, wherein the plurality of DR5BDs is four DR5BDs.

4. The isolated polypeptide of claim 1, wherein the plurality of DR5BDs is six DR5BDs.

5. The isolated polypeptide of claim 1, wherein each DR5BD comprises the amino acid sequence of SEQ ID NO: 87.

6. The isolated polypeptide of claim 2, wherein each DR5BD comprises the amino acid sequence of SEQ ID NO: 87.

7. The isolated polypeptide of claim 3, wherein each DR5BD comprises the amino acid sequence of SEQ ID NO: 87.

8. The isolated polypeptide of claim 4, wherein each DR5BD comprises the amino acid sequence of SEQ ID NO: 87.

9. The isolated polypeptide of claim 3, wherein the polypeptide is a homodimer of the structure: DR5BD-Linker-DR5BD-Linker-Hinge-Fc, where each DR5BD is a humanized VHH sequence.

10. The isolated polypeptide of claim 9, wherein each DR5BD comprises the amino acid sequence of SEQ ID NO: 87.

11. The isolated polypeptide of claim 1, wherein the isolated polypeptide comprises an immunoglobulin hinge region and an immunoglobulin Fc region.

12. The isolated polypeptide of claim 11, wherein the immunoglobulin hinge region comprises an amino acid sequence selected from EPKSSDKTHTCPPC (SEQ ID NO: 6), DKTHTCPPC (SEQ ID NO: 7), ESKYGPPCPPC (SEQ ID NO: 8).

13. The isolated polypeptide of claim 11, wherein the immunoglobulin Fc region is an IgG1 Fc region, an IgG2 Fc region, an IgG3 Fc region, or an IgG1 Fc region.

14. The isolated polypeptide of claim 11, wherein the immunoglobulin Fc region comprises an amino acid sequence selected from SEQ ID NOs: 1-5 or 127.

15. The isolated polypeptide of claim 1, wherein the polypeptide comprises the amino acid sequence of SEQ ID NO: 113.

16. The isolated polypeptide of claim 15, wherein the polypeptide is a homodimer of the amino acid sequence of SEQ ID NO: 113 fused to an Fc region polypeptide.

17. The isolated polypeptide of claim 1, wherein each amino acid linker consists of 5-20 amino acids.

18. The isolated polypeptide of claim 17, wherein each amino acid linker is composed predominantly of glycine and serine.

19. The isolated polypeptide of claim 18, wherein each amino acid linker comprises an amino acid sequence selected from GGSGGS (SEQ ID NO: 11); GGSGGSGGS (SEQ ID NO: 12); GGSGGSGGSGGS (SEQ ID NO: 13); and GGSGGSGGSGGSGGS (SEQ ID NO: 14).

20. The isolated polypeptide of claim 10, wherein each amino acid linker consists of 5-20 amino acids.

21. The isolated polypeptide of claim 20, wherein each amino acid linker is composed predominantly of glycine and serine.

22. The isolated polypeptide of claim 21, wherein each amino acid linker comprises an amino acid sequence selected from GGSGGS (SEQ ID NO: 11); GGSGGSGGS (SEQ ID NO: 12); GGSGGSGGSGGS (SEQ ID NO: 13); and GGSGGSGGSGGSGGS (SEQ ID NO: 14).

23. The isolated polypeptide of claim 1, wherein each VHH is a humanized VHH.

24. An isolated polypeptide that binds death receptor 5 (DR5), wherein the polypeptide is a homodimer of the amino acid sequence of SEQ ID NO: 113 fused to an Fc region polypeptide of SEQ ID NO: 2.

* * * * *

UNITED STATES PATENT AND TRADEMARK OFFICE
CERTIFICATE OF CORRECTION

PATENT NO. : 10,308,720 B2  
APPLICATION NO. : 15/213296  
DATED : June 4, 2019  
INVENTOR(S) : John C. Timmer et al.

Page 1 of 1

It is certified that error appears in the above-identified patent and that said Letters Patent is hereby corrected as shown below:

In the Claims

In Claim 13, Column 216, Line 12, "IgG1" should read --IgG4--.

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*